(12) United States Patent
Sorge

(10) Patent No.: US 7,381,532 B2
(45) Date of Patent: Jun. 3, 2008

(54) COMPOSITIONS AND METHODS FOR THE DETECTION OF A NUCLEIC ACID USING A CLEAVAGE REACTION

(75) Inventor: Joseph A. Sorge, Del Mar, CA (US)

(73) Assignee: Stratagene California, La Jolla, CA (US)

( * ) Notice: Subject to any disclaimer, the term of this patent is extended or adjusted under 35 U.S.C. 154(b) by 99 days.

(21) Appl. No.: 11/286,573

(22) Filed: Nov. 23, 2005

(65) Prior Publication Data

US 2006/0246469 A1    Nov. 2, 2006

Related U.S. Application Data

(63) Continuation-in-part of application No. 11/249,059, filed on Oct. 11, 2005, now abandoned, which is a continuation-in-part of application No. 09/728,574, filed on Nov. 30, 2000, now Pat. No. 7,118,860, which is a continuation-in-part of application No. 09/650,888, filed on Aug. 30, 2000, now Pat. No. 6,548,250, which is a continuation-in-part of application No. 09/430,692, filed on Oct. 29, 1999, now Pat. No. 6,528,254.

(51) Int. Cl.
*C12Q 1/68* (2006.01)
*C07H 21/02* (2006.01)
*C07H 21/04* (2006.01)

(52) U.S. Cl. .......................... 435/6; 536/23.1; 536/24.3
(58) Field of Classification Search .................... 435/6; 536/23.1, 24.3
See application file for complete search history.

(56) References Cited

U.S. PATENT DOCUMENTS

| | | | | |
|---|---|---|---|---|
| 4,683,195 A | * | 7/1987 | Mullis et al. | 435/6 |
| 4,683,202 A | * | 7/1987 | Mullis | 435/91.2 |
| 4,800,159 A | * | 1/1989 | Mullis et al. | 435/91.2 |
| 5,210,015 A | * | 5/1993 | Gelfand et al. | 435/6 |
| 5,270,184 A | * | 12/1993 | Walker et al. | 435/91.2 |
| 5,424,413 A | * | 6/1995 | Hogan et al. | 536/24.31 |
| 5,487,972 A | * | 1/1996 | Gelfand et al. | 435/6 |
| 5,538,848 A | * | 7/1996 | Livak et al. | 435/6 |
| 5,719,028 A | * | 2/1998 | Dahlberg et al. | 435/6 |
| 5,804,375 A | * | 9/1998 | Gelfand et al. | 435/6 |
| 5,837,450 A | * | 11/1998 | Dahlberg et al. | 435/6 |
| 5,843,669 A | * | 12/1998 | Kaiser et al. | 435/6 |
| 5,846,717 A | * | 12/1998 | Brow et al. | 435/6 |
| 5,888,780 A | * | 3/1999 | Dahlberg et al. | 435/91.53 |
| 6,150,097 A | * | 11/2000 | Tyagi et al. | 435/6 |
| 6,194,149 B1 | * | 2/2001 | Neri et al. | 435/6 |
| 6,350,580 B1 | * | 2/2002 | Sorge | 435/6 |
| 6,528,254 B1 | * | 3/2003 | Sorge | 435/6 |
| 6,548,250 B1 | * | 4/2003 | Sorge | 435/6 |
| 6,589,743 B2 | * | 7/2003 | Sorge | 435/6 |
| 6,893,819 B1 | * | 5/2005 | Sorge | 435/6 |
| 7,118,860 B2 | * | 10/2006 | Sorge et al. | 435/6 |
| 7,276,597 B2 | * | 10/2007 | Sorge | 536/24.3 |
| 2005/0147996 A1 | * | 7/2005 | Sorge | 435/6 |
| 2005/0255512 A1 | * | 11/2005 | Sorge et al. | 435/6 |
| 2006/0094036 A1 | * | 5/2006 | Sorge et al. | 435/6 |
| 2006/0110748 A1 | * | 5/2006 | Sorge | 435/6 |
| 2007/0015180 A1 | * | 1/2007 | Sorge | 435/6 |
| 2007/0099205 A1 | * | 5/2007 | Sorge | 435/6 |
| 2007/0099206 A1 | * | 5/2007 | Sorge | 435/6 |
| 2007/0105138 A1 | * | 5/2007 | Sorge | 435/6 |

OTHER PUBLICATIONS

Ugozzoli et al. Detection of specific alleles by using allele—specific primer extension followed by capture on solid support. GATA 9(4) :107-112 (1992).*
Hosfield et al. Structure of ther DNA repair and replication endonuclease and exonuclease FEN-1: coupling DNA and PCNA binding to FEN-1 activity. Cell 95 : 135-146 (1998).*
Saiki et al. , Analysis of enzymatically amplified β-globin and HLA-DQa DNA with allele-specific oligonucleotide probes. Nature 324: 163-166 (1986).*
Lyamichev et al., Polymorphism identification and quantitative detection of genomic DNA by invasive cleavage of oligonucleotide probes. Nature Biotechnology 17 : 292-296 (1999).*
Mein et al., Evaluation of single nucleotide polymorphism typing with invader on PCR amplicons and its automation. Genome Research 10 :330-343 (2000).*
Hsu et al., Genotyping Single-Nucleotide polymorphisms by the invader assay with dual-color fluorescence polarization detection. Clinical Chemisty 47(8) :1373-1377 (2001).*
Latif et al., Fluorescence polarization in homogeneous nucleic acid analysis II : 5'-nuclease assay. Genome Research 11:436-440 (2001).*
Till et al. Mismatch cleavage by single-strand specific nucleases. Nucleic Acids Research 32(8) : 2632-2641 (2004).*

* cited by examiner

*Primary Examiner*—Ethan Whisenant

(57) ABSTRACT

The invention relates to a method of generating a signal indicative of the presence of a target nucleic acid sequence in a sample, where the method includes forming a cleavage structure by incubating a sample containing a target nucleic acid sequence with a nucleic acid polymerase and cleaving the cleavage structure with a nuclease to generate a cleaved nucleic acid fragment. The invention also relates to methods of detecting or measuring a target nucleic acid sequence, where the method includes forming a cleavage structure by incubating a target nucleic acid sequence with a nucleic acid polymerase, cleaving the cleavage structure with a nuclease and detecting or measuring the release of a fragment.

34 Claims, 23 Drawing Sheets

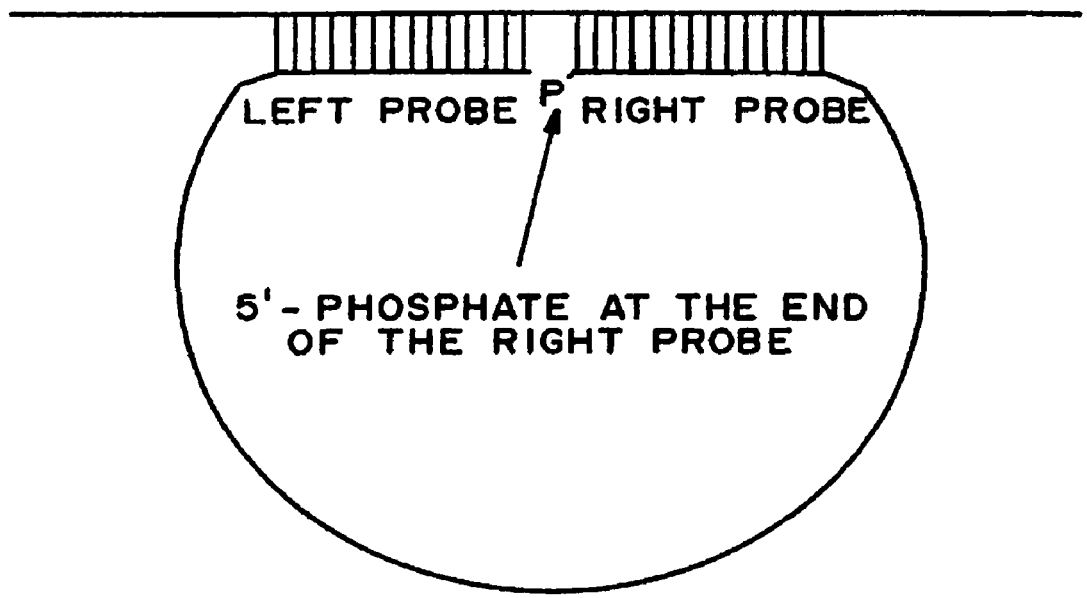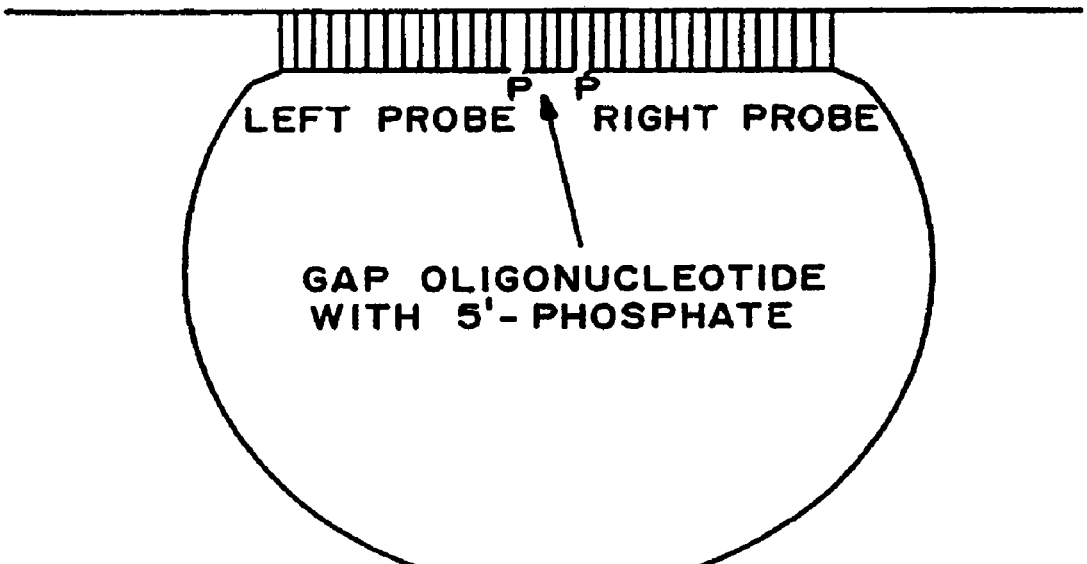
FIG. 9A

"3'B" represents some type of 3' end that cannot be extended by a polymerase. The cleaved molecule is shown to have a "3'B", as a preferred embodiment, but could also have a normal 3' hydroxyl end.

"3'B" represents some type of 3' end that cannot be extended by a polymerase. The cleaved molecule is shown to have a "3'B", as a preferred embodiment, but could also have a normal 3' hydroxyl end.

"3'B" represents some type of 3' end that cannot be extended by a polymerase. The cleaved molecule is shown to have a "3'B", as a preferred embodiment, but could also have a normal 3' hydroxyl end.

"3'B" represents some type of 3' end that cannot be extended by a polymerase. The cleaved molecule is shown to have a "3'B", as a preferred embodiment, but could also have a normal 3' hydroxyl end.

COMPOSITIONS AND METHODS FOR THE DETECTION OF A NUCLEIC ACID USING A CLEAVAGE REACTION

CROSS-REFERENCES TO RELATED APPLICATIONS

This application is a Continuation-in-Part of U.S. application Ser. No. 11/249,059, which was filed on Oct. 11, 2005 now abandoned; which is a Continuation-in-Part of U.S. application Ser. No. 09/728,574, which was filed on Nov. 30, 2000 now U.S. Pat. No. 7,118,860; which is a continuation-in-part of U.S. application Ser. No. 09/650,888, filed Aug. 30 2000, now U.S. Pat. No. 6,548,250 which is a continuation-in-part of U.S. application Ser. No. 09/430,692, filed Oct. 29, 1999, now U.S. Pat. No. 6,528,254, the entire disclosures of all are incorporated herein by reference in their entireties.

BACKGROUND OF THE INVENTION

The fidelity of DNA replication, recombination, and repair is essential for maintaining genome stability, and all of these processes depend on 5' to 3' exonuclease enzymes which are present in all organisms. For DNA repair, these enzymes are required for damaged fragment excision and recombinational mismatch correction. For replication, these nucleases are critical for the efficient processing of Okazaki fragments during lagging strand DNA synthesis. In *Escherichia coli*, this latter activity is provided by DNA polymerase I (PolI); *E. coli* strains with inactivating mutations in the PolI 5' to 3' exonuclease domain are not viable due to an inability to process Okazaki fragments. Eukaryotic DNA polymerases, however, lack an intrinsic 5' to 3' exonuclease domain, and this critical activity is provided by the multifunctional, structure-specific metallonuclease FEN-1(five' exonuclease-1 or flap endonuclease-1), which also acts as an endonuclease for 5' DNA flaps (Reviewed in Hosfield et al., 1998a, *Cell*, 95:135).

Methods of detecting and/or measuring a nucleic acid wherein an enzyme produces a labeled nucleic acid fragment are known in the art.

U.S. Pat. Nos. 5,843,669, 5,719,028, 5,837,450, 5,846,717 and 5,888,780 disclose a method of cleaving a target DNA molecule by incubating a 5' labeled target DNA with a DNA polymerase isolated from *Thermus aquaticus* (Taq polymerase) and a partially complementary oligonucleotide capable of hybridizing to sequences at the desired point of cleavage. The partially complementary oligonucleotide directs the Taq polymerase to the target DNA through formation of a substrate structure containing a duplex with a 3' extension opposite the desired site of cleavage wherein the non-complementary region of the oligonucleotide provides a 3' arm and the unannealed 5' region of the substrate molecule provides a 5' arm. The partially complementary oligonucleotide includes a 3' nucleotide extension capable of forming a short hairpin. The release of labeled fragment is detected following cleavage by Taq polymerase.

U.S. Pat. Nos. 5,843,669, 5,719,028, 5,837,450, 5,846,717 and 5,888,780 disclose the generation of mutant, thermostable DNA polymerases that have very little or no detectable synthetic activity, and wild type thermostable nuclease activity. The mutant polymerases are said to be useful because they lack 5' to 3' synthetic activity; thus synthetic activity is an undesirable side reaction in combination with a DNA cleavage step in a detection assay.

U.S. Pat. Nos. 5,843,669, 5,719,028, 5,837,450, 5,846,717 and 5,888,780 disclose that wild type Taq polymerase or mutant Taq polymerases that lack synthetic activity can release a labeled fragment by cleaving a 5' end labeled hairpin structure formed by heat denaturation followed by cooling, in the presence of a primer that binds to the 3' arm of the hairpin structure. Further, U.S. Pat. Nos. 5,843,669, 5,719,028, 5,837,450, 5,846,717 and 5,888,780 teach that the mutant Taq polymerases lacking synthetic activity can also cleave this hairpin structure in the absence of a primer that binds to the 3' arm of the hairpin structure.

U.S. Pat. Nos. 5,843,669, 5,719,028, 5,837,450, 5,846,717 and 5,888,780 also disclose that cleavage of this hairpin structure in the presence of a primer that binds to the 3' arm of the hairpin structure by mutant Taq polymerases lacking synthetic activity yields a single species of labeled cleaved product, while wild type Taq polymerase produces multiple cleavage products and converts the hairpin structure to a double stranded form in the presence of dNTPs, due to the high level of synthetic activity of the wild type Taq enzyme.

The 5' to 3' exonuclease activity of a nucleic acid polymerase can impair the amplification of certain nucleic acids. There is also a need in the art for a method of generating a signal using a nucleic acid cleavage reaction in the absence of a 5' to 3' exonuclease activity of a nucleic acid polymerase.

U.S. Pat. Nos. 5,843,669, 5,719,028, 5,837,450, 5,846,717 and 5,888,780 also disclose that mutant Taq polymerases exhibiting reduced synthetic activity, but not wild type Taq polymerase, can release a single labeled fragment by cleaving a linear nucleic acid substrate comprising a 5' end labeled target nucleic acid and a complementary oligonucleotide wherein the complementary oligonucleotide hybridizes to a portion of the target nucleic acid such that 5' and 3' regions of the target nucleic acid are not annealed to the oligonucleotide and remain single stranded.

There is a need in the art for a method of generating a signal of a discrete size that can be easily distinguished from oligonucleotide fragments that may arise from nuclease contaminants, using a nucleic acid cleavage reaction in the absence of 5' to 3' exonuclease activity of a nucleic acid polymerase.

U.S. Pat. Nos. 5,843,669, 5,719,028, 5,837,450, 5,846,717 and 5,888,780 also disclose a method of cleaving a labeled nucleic acid substrate at naturally occurring areas of secondary structure. According to this method, biotin labeled DNA substrates are prepared by PCR, mixed with wild type Taq polymerase or CleavaseBN (a mutant Taq polymerase with reduced synthetic activity and wild type 5' to 3' nuclease activity), incubated at 95° C. for 5 seconds to denature the substrate and then quickly cooled to 65° C. to allow the DNA to assume its unique secondary structure by allowing the formation of intra-strand hydrogen bonds between the complementary bases. The reaction mixture is incubated at 65° C. to allow cleavage to occur and biotinylated cleavage products are detected.

There is a need in the art for a method of generating a signal using a nucleic acid cleavage reaction in the absence of a 5' to 3' exonuclease activity of a nucleic acid polymerase wherein the cleavage structure is not required to contain areas of secondary structure.

Methods of detecting and/or measuring a nucleic acid wherein a FEN-1 enzyme is used to generate a labeled nucleic acid fragment are known in the art.

U.S. Pat. No. 5,843,669 discloses a method of detecting polymorphisms by cleavase fragment length polymorphism analysis using a thermostable FEN-1 nuclease in the presence or absence of a mutant Taq polymerase exhibiting reduced synthetic activity. According to this method, double stranded Hepatitis C virus (HCV) DNA fragments are labeled by using 5' end labeled primers (labeled with TMR fluorescent dye) in a PCR reaction. The TMR labeled PCR products are denatured by heating to 95° C. and cooled to 55° C. to generate a cleavage structure. U.S. Pat. No. 5,843,669 discloses that a cleavage structure comprises a region of a single stranded nucleic acid substrate containing secondary structure. Cleavage is carried out in the presence of CleavaseBN nuclease, FEN-1 nuclease derived from the archaebacteria *Methanococcus jannaschii* or both enzymes. Labeled reaction products are visualized by gel electrophoresis followed by fluoroimaging. U.S. Pat. No. 5,843,669 discloses that CleavaseBN nuclease and *Methanococcus jannaschii* FEN-1 nuclease produce cleavage patterns that are easily distinguished from each other, and that the cleavage patterns from a reaction containing both enzymes include elements of the patterns produced by cleavage with each individual enzyme but are not merely a composite of the cleavage patterns produced by each individual enzyme. This indicates that some of the fragments that are not cleaved by one enzyme (and which appear as a band in that enzyme's pattern) can be cleaved by a second enzyme in the same reaction mixture.

Lyamichev et al. disclose a method for detecting DNAs wherein overlapping pairs of oligonucleotide probes that are partially complementary to a region of target DNA are mixed with the target DNA to form a 5' flap region, and wherein cleavage of the labeled downstream probe by a thermostable FEN-1 nuclease produces a labeled cleavage product. Lyamichev et al. also disclose reaction conditions wherein multiple copies of the downstream oligonucleotide probe can be cleaved for a single target sequence in the absence of temperature cycling, so as to amplify the cleavage signal and allow quantitative detection of target DNA at sub-attomole levels (Lyamichev et al., 1999, *Nat. Biotechnol.*, 17:292).

The polymerase chain reaction (PCR) technique, is disclosed in U.S. Pat. Nos. 4,683,202, 4,683,195 and 4,800,159. In its simplest form, PCR is an in vitro method for the enzymatic synthesis of specific DNA sequences, using two oligonucleotide primers that hybridize to opposite strands and flank the region of interest in the target DNA. A repetitive series of reaction steps involving template denaturation, primer annealing and the extension of the annealed primers by DNA polymerase results in the exponential accumulation of a specific fragment whose termini are defined by the 5' ends of the primers. PCR is reported to be capable of producing a selective enrichment of a specific DNA sequence by a factor of $10^9$. The PCR method is also described in Saiki et al., 1985, *Science*, 230:1350.

While the PCR technique is an extremely powerful method for amplifying nucleic acid sequences, the detection of the amplified material requires additional manipulation and subsequent handling of the PCR products to determine whether the target DNA is present. It is desirable to decrease the number of subsequent handling steps currently required for the detection of amplified material. An assay system, wherein a signal is generated while the target sequence is amplified, requires fewer handling steps for the detection of amplified material, as compared to a PCR method that does not generate a signal during the amplification step.

U.S. Pat. Nos. 5,210,015 and 5,487,972 disclose a PCR based assay for releasing labeled probe comprising generating a signal during the amplification step of a PCR reaction in the presence of a nucleic acid to be amplified, Taq polymerase that has 5' to 3' exonuclease activity and a 5', 3' or 5' and 3' end-labeled probe comprising a region complementary to the amplified region and an additional non-complementary 5' tail region. U.S. Pat. Nos. 5,210,015 and 5,487,972 disclose further that this PCR based assay can liberate the 5' labeled end of a hybridized probe when the Taq polymerase is positioned near the labeled probe by an upstream probe in a polymerization independent manner, e.g. in the absence of dNTPs.

SUMMARY OF THE INVENTION

The invention provides a method of generating a signal indicative of the presence of a target nucleic acid sequence in a sample comprising forming a cleavage structure by incubating a sample comprising a target nucleic acid sequence with a nucleic acid polymerase, and cleaving the cleavage structure with a FEN nuclease to generate a signal, wherein generation of the signal is indicative of the presence of a target nucleic acid sequence in the sample.

In one aspect, the present invention provides a method for detecting the presence of a target nucleic acid, wherein the method comprises:

a) providing:
  a target nucleic acid, which comprises in the 3' to 5' order a first hybridization site and a second hybridization site;
  an upstream oligonucleotide that is complementary to the first hybridization site and wherein the upstream oligonucleotide has a blocked 3' end, and
  a downstream probe comprising a 5' region and a 3' region, wherein the 3' region is complementary to the second hybridization site and the 5' forms a non-complementary 5' flap when the downstream probe is annealed to the target;

b) annealing the upstream oligonucleotide and the downstream probe to the target nucleic acid to form a cleavage structure;

c) cleaving the cleavage structure with a nuclease to release the non-complementary 5' flap; and d) detecting the released non-complementary 5' flap, wherein the released non-complementary 5' flap is indicative of the presence of the target nucleic acid in the sample.

In another aspect, the present invention provides a method for forming a cleavage structure and cleaving the cleavage structure, wherein the method comprises:

a) providing:
  a target nucleic acid, which comprises in the 3' to 5' order a first hybridization site and a second hybridization site;
  an upstream oligonucleotide that is complementary to the first hybridization site and wherein the upstream oligonucleotide has a blocked 3' end, and
  a downstream probe comprising a 5' region and a 3' region, wherein the 3' region is complementary to the second hybridization site and the 5' forms a non-complementary 5' flap when the downstream probe is annealed to the target;

b) annealing the upstream oligonucleotide and the downstream probe to the target nucleic acid to form a cleavage structure; and c) cleaving the cleavage structure with a FEN nuclease enzyme derived from *Pyrococcus furiosus* to release the non-complementary 5' flap.

In yet another aspect, the present invention provides a method for forming a cleavage structure in a sample, cleaving the cleavage structure, and transcribing a nucleic acid complementary to the target nucleic acid, wherein the method comprises:

a) providing:
- a target nucleic acid, which comprises in the 3' to 5' order a first hybridization site, a second hybridization site and a third hybridization site,
- an upstream extension primer that is complementary to the first hybridization site;
- a clamping oligonucleotide that is complementary to the second hybridization site and wherein the clamping oligonucleotide comprises a blocked 3' end and a 5' end with a clamp, wherein the clamp inhibits the displacement of the clamping oligonucleotide by a nucleic acid polymerase, and
- a downstream probe comprising a 5' region and a 3' region, wherein the 3' region is complementary to the third hybridization site and the 5' region forms a non-complementary 5' flap when the downstream probe is hybridized to the target nucleic acid;

b) annealing the upstream extension primer, the clamping oligonucleotide, and the downstream probe to the target nucleic acid, wherein the clamping oligonucleotide and downstream probe form a cleavage structure;

c) cleaving the cleavage structure with a nuclease to release the non-complementary 5' flap;

d) extending a complementary strand from the upstream extension primer to the clamp of the clamping oligonucleotide;

e) dissociating the clamping oligonucleotide and the downstream probe from the target nucleic acid to allow the nucleic acid polymerase access to the target nucleic acid previously covered by the clamping oligonucleotide and the downstream probe;

f) further extending the strand complementary to the target nucleic acid; and g) detecting the released non-complementary 5' flap, wherein the released non-complementary 5' flap is indicative of the presence of the target nucleic acid in the sample.

In yet another aspect, the present invention provides a method for forming a cleavage structure in a sample, cleaving the cleavage, and transcribing a nucleic acid complementary to the target nucleic acid, wherein the method comprises:

a) providing:
- a target nucleic acid, which comprises in the 3' to 5' order a first hybridization site, a second hybridization site and a third hybridization site,
- an upstream extension primer that is complementary to the first hybridization site;
- a clamping oligonucleotide that is complementary to the second hybridization site and wherein the clamping oligonucleotide comprises a blocked 3' end and a 5' end with a clamp, wherein the clamp inhibits the displacement of the clamping oligonucleotide by a nucleic acid polymerase, and
- a downstream probe comprising a 5' region and a 3' region, wherein the 3' region is complementary to the third hybridization site and the 5' region forms a non-complementary 5' flap when the downstream probe is hybridized to the target nucleic acid;

b) annealing the upstream extension primer, the clamping oligonucleotide, and the downstream probe to the target nucleic acid, wherein the clamping oligonucleotide and downstream probe form a cleavage structure;

c) cleaving the cleavage structure with a FEN nuclease enzyme derived from *Pyrococcus furiosus* to release the non-complementary 5' flap;

d) extending the complementary strand from the upstream extension primer to the clamp of the clamping oligonucleotide;

e) dissociating the clamping oligonucleotide and the downstream probe from the target nucleic acid to allow the nucleic acid polymerase access to the target nucleic acid-previously covered by the clamping oligonucleotide and the downstream probe;

f) further extending the strand complementary to the target nucleic acid; and g) detecting the released non-complementary 5' flap, wherein the released non-complementary 5' flap is indicative of the presence of the target nucleic acid in the sample.

In still another aspect, the present invention provides a method for forming a cleavage structure in a sample, cleaving the cleavage, and transcribing a nucleic acid complementary to the target nucleic acid, wherein the method comprises:

a) providing:
- a target nucleic acid, which comprises in the 3' to 5' order a first hybridization site, a second hybridization site and a third hybridization site,
- an upstream oligonucleotide extension primer that is complementary to the first hybridization site,
- an upstream oligonucleotide that is complementary to the second hybridization site and wherein the upstream oligonucleotide comprises a blocked 3' end, and
- a downstream probe comprising a 5' region and a 3' region, wherein the 3' region is complementary to the third hybridization site and the 5' region forms a non-complementary 5' flap when the downstream probe is annealed to the target;

b) annealing the upstream oligonucleotide and the downstream probe to the target nucleic acid to form a cleavage structure;

c) cleaving the cleavage structure with a nuclease to release the non-complementary 5' flap;

d) annealing the upstream extension primer to the target nucleic acid;

e) extending the upstream oligonucleotide extension primer to synthesize a strand complementary to the target nucleic acid; and f) detecting the released non-complementary 5' flap, wherein the released non-complementary 5' flap is indicative of the presence of the target nucleic acid in the sample.

In another aspect, the present invention provides a method for forming a cleavage structure in a sample, cleaving the cleavage structure, and transcribing a nucleic acid complementary to the target nucleic acid, wherein the method comprises:

a) providing:
- a target nucleic acid, which comprises in the 3' to 5' order a first hybridization site, a second hybridization site and a third hybridization site,
- an upstream oligonucleotide extension primer that is complementary to the first hybridization site,
- an upstream oligonucleotide that is complementary to the second hybridization site and wherein the upstream oligonucleotide comprises a blocked 3' end, and a downstream probe comprising a 5' region and a 3' region, wherein the 3' region is complementary to the third hybridization site and the 5' region forms a non-complementary 5' flap when the downstream probe is annealed to the target;
b) annealing the upstream oligonucleotide and the downstream probe to the target nucleic acid to form a cleavage structure;
c) cleaving the cleavage structure with a FEN nuclease enzyme derived from *Pyrococcus furiosus* to release the non-complementary 5' flap; and
d) annealing the upstream extension primer to the target nucleic acid;
e) extending the upstream extension primer to synthesize a strand complementary to the target nucleic acid; and
f) detecting the released non-complementary 5' flap, wherein the released non-complementary 5' flap is indicative of the presence of the target nucleic acid in the sample.

In yet another aspect, the present invention provides a method for forming a cleavage structure in a sample, cleaving the cleavage, transcribing a nucleic acid complementary to the target nucleic acid, and amplifying the target nucleic acid, wherein the method comprises:
a) providing:
   a target nucleic acid, which comprises region A',
   a forward extension primer comprises a non-complementary 5' tag region (X) and a 3' priming region (A), wherein the 5' tag region is not complementary to the target prior to amplification and the 3' priming region (A) is complementary to region (A') in the target nucleic acid,
   an upstream oligonucleotide comprising at least a portion of region X and wherein the upstream oligonucleotide has a blocked 3' end,
   a downstream probe comprising a 5' region and a 3' region, wherein the 3' region comprises at least a portion of region A and the 5' region forms a non-complementary 5' flap when the downstream probe is annealed to the A' portion of the target nucleic acid, and
   a reverse extension primer that primes a second strand comprising at least a portion of the target nucleic acid;
b) annealing region A of the forward extension primer to the target nucleic acid;
c) extending the forward extension primer to produce a complementary strand of the target nucleic acid, wherein the complementary strand includes region A and region X;
d) denaturing the target nucleic acid and the complementary strand;
e) annealing the reverse extension primer to a region of the complementary strand downstream of region A;
f) extending the strand from the reverse extension primer to produce a second strand comprising at least a portion of the target nucleic acid sequence, region A', and a region (X') complementary to the 5' tag;
g) denaturing the complementary strand from the second strand;
h) annealing the upstream oligonucleotide and the downstream probe to the second strand to form a cleavage structure;
i) cleaving the cleavage structure with a nuclease to release the non-complementary 5' flap of the downstream oligonucleotide; and
j) detecting the released non-complementary 5' flap, wherein the released non-complementary 5' flap is indicative of the presence of the target nucleic acid in the sample.

In yet another aspect, the present invention provides a method for forming a cleavage structure in a sample, cleaving the cleavage structure, transcribing a nucleic acid complementary to the target nucleic acid, and amplifying the target nucleic acid, wherein the method comprises:
a) providing:
   a target nucleic acid, which comprises region A',
   a forward extension primer comprises a non-complementary 5' tag region (X) and a 3' priming region (A), wherein the 5' tag region is not complementary to the target prior to amplification and the 3' priming region (A) is complementary to region (A') in the target nucleic acid,
   an upstream oligonucleotide comprising at least a portion of region X and wherein the upstream oligonucleotide has a blocked 3' end,
   a downstream probe comprising a 5' region and a 3' region, wherein the 3' region comprises at least a portion of region A and the 5' region forms a non-complementary 5' flap when the downstream probe is annealed to the A' portion of the target nucleic acid, and
   a reverse extension primer that primes a second strand comprising at least a portion of the target nucleic acid;
b) annealing region A of the forward extension primer to the target nucleic acid;
c) extending the forward extension primer to produce a complementary strand of the target nucleic acid, wherein the complementary strand includes region A and region X;
d) denaturing the target nucleic acid and the complementary strand;
e) annealing the reverse extension primer to a region of the complementary strand downstream of region A;
f) extending the strand from the reverse extension primer to produce a second strand comprising at least a portion of the target nucleic acid sequence, region A', and a region (X') complementary to the 5' tag;
g) denaturing the complementary strand from the second strand;
h) annealing the upstream oligonucleotide and the downstream probe to the second strand to form a cleavage structure;
i) cleaving the cleavage structure with a FEN nuclease enzyme derived from *Pyrococcus furiosus* to release the non-complementary 5' flap of the downstream oligonucleotide; and
j) detecting the released non-complementary 5' flap, wherein the released non-complementary 5' flap is indicative of the presence of the target nucleic acid in the sample.

In yet another aspect, the present invention provides a method for forming a cleavage structure in a sample, cleaving the cleavage structure, transcribing a nucleic acid complementary to the target nucleic acid, and amplifying the target nucleic acid, wherein the method comprises:
a) providing:
   a target nucleic acid, which comprises from 3' to 5' an A' region and a T' region, wherein said A' and T' regions are non-contiguous,
   a forward extension primer comprises a 5' tag region comprising two subregions (X1 and X2), wherein X1 is upstream of X2 and a 3' priming region (A), wherein the 5' tag region is not complementary to the target prior to amplification and the 3' priming region (A) is complementary to region A' of the target nucleic acid, an upstream oligonucleotide comprising at least a portion of region X1 and wherein the upstream oligonucleotide has a blocked 3' end, a downstream probe comprising a 5' region and a 3' region, wherein the 3' region comprises at least a portion of region X2, and a region T which is downstream of region X2 and is complementary to T' of the target nucleic acid, and wherein the 5' region forms a non-complementary 5' flap when the downstream probe is annealed to the A' region of the target nucleic acid, and a reverse extension primer that primes a second strand comprising at least a portion of the target nucleic acid;

b) annealing complementary region A of the forward extension primer to the A' region and T' region of the target nucleic acid;

c) extending the forward extension primer to produce a complementary strand of the target nucleic acid, wherein the complementary strand includes region A and regions X1 and X2;

d) denaturing the target nucleic acid and the complementary strand;

e) annealing the reverse extension primer to a region of the complementary strand downstream of region T;

f) extending the strand from the reverse extension primer to produce a second strand comprising at least a portion of the target nucleic acid sequence, region A', region T' and a region (X1', X2') complementary to the 5' tag;

g) denaturing the complementary strand from the second strand;

h) annealing the upstream oligonucleotide and the downstream probe to the second strand to form a cleavage structure i) cleaving the cleavage structure with a nuclease to release the non-complementary 5' flap of the downstream oligonucleotide; and j) detecting the released non-complementary 5' flap, wherein the released non-complementary 5' flap is indicative of the presence of the target nucleic acid in the sample.

In another aspect, the present invention provides a method for forming a cleavage structure in a sample, cleaving the cleavage structure, transcribing a nucleic acid complementary to the target nucleic acid, and amplifying the target nucleic acid, wherein the method comprises:

a) providing:

a target nucleic acid, which comprises from 3' to 5' a A' region and a T' region, wherein said A' and T' regions are non-contiguous, a forward extension primer comprises a 5' tag region comprising two subregions (X1 and X2), wherein X1 is upstream of X2 and a 3' priming region (A), wherein the 5' tag region is not complementary to the target prior to amplification and the 3' priming region (A) is complementary to region (A') of the target nucleic acid, an upstream oligonucleotide comprising at least a portion of region X1 and wherein the upstream oligonucleotide has a blocked 3' end, a downstream probe comprising a 5' region and a 3' region, wherein the 3' region comprises at least a portion of region X2, and a region T which is downstream of region X2 and is complementary to T' of the target nucleic acid, and wherein the 5' region forms a non-complementary 5' flap when the downstream probe is annealed to the A' region of the target nucleic acid, and a reverse extension primer that primes a second strand comprising at least a portion of the target nucleic acid;

b) annealing complementary region A of the forward extension primer to the A' region and T' region of the target nucleic acid;

c) extending the forward extension primer to produce a complementary strand of the target nucleic acid, wherein the complementary strand includes region A and regions X1 and X2;

d) denaturing the target nucleic acid and the complementary strand;

e) annealing the reverse extension primer to a region of the complementary strand downstream of region T;

f) extending the strand from the reverse extension primer to produce a second strand comprising at least a portion of the target nucleic acid sequence, region A', region T' and a region (X1', X2') complementary to the 5' tag;

g) denaturing the complementary strand from the second strand;

h) annealing the upstream oligonucleotide and the downstream probe to the second strand to form a cleavage structure i) cleaving the cleavage structure with a FEN nuclease derived from *Pyrococcus furiosus* to release the non-complementary 5' flap of the downstream oligonucleotide; and j) detecting the released non-complementary 5' flap, wherein the released non-complementary 5' flap is indicative of the presence of the target nucleic acid in the sample.

As used herein a "nuclease" or a "cleavage agent" refers to an enzyme that is specific for, that is, cleaves a cleavage structure according to the invention and is not specific for, that is, does not substantially cleave either a probe or a primer that is not hybridized to a target nucleic acid, or a target nucleic acid that is not hybridized to a probe or a primer. The term "nuclease" includes an enzyme that possesses 5' endonucleolytic activity for example a DNA polymerase, e.g. DNA polymerase I from *E. coli*, and DNA polymerase from *Thermus aquaticus* (Taq), *Thermus thermophilus* (Tth), and *Thermus flavus* (Tfl). A nuclease according to the invention also includes *Saccharomyces cerevisiae* RAD27, and *Schizosaccharomyces pombe* RAD2, Pol I DNA polymerase associated 5' to 3' exonuclease domain, (e.g. *E. coli, Thermus aquaticus* (Taq), *Thermus flavus* (Tfl), *Bacillus caldotenax* (Bca), *Streptococcus pneumoniae*) and phage functional homologs of FEN including but not limited to T5 5' to 3' exonuclease, T7 gene 6 exonuclease and T3 gene 6 exonuclease. Preferably, only the 5' to 3' exonuclease domains of Taq, Tfl and Bca FEN nuclease are used. The term "nuclease" does not include RNAse H.

As used herein a "FEN nuclease" refers to an enzyme that cleaves a cleavage structure according to the invention. The term "FEN nuclease" encompasses an enzyme that consists essentially of a 5' exonuclease and/or an endonuclease activity. As used herein, "consists essentially of" refers to an enzyme wherein the predominant activity of the enzyme is a 5' exonucleolytic and/or endonucleolytic activity, such that one or both of 5' to 3' synthetic activity and 3' single-stranded flap cleavage activity (i.e., 3' endonucleolytic and/ or 3' exonucleolytic activity) are substantially lacking. "Substantially lacks" means that the FEN nuclease possesses no more than 5% or 10% and preferably less than 0.1%, 0.5%, or 1% of the activity of a wild type enzyme (e.g. for 5' to 3' synthetic activity and the 3' endonucleolytic and/or '3 exonucleolytic activities, the enzyme may be a wild type DNA polymerase having these activities). 5' to 3' synthetic activity can be measured, for example, in a nick translation assay or an enzymatic sequencing reaction which involve the formation of a phosphodiester bridge between the 3'-hydroxyl group at the growing end of an oligonucleotide primer and the 5'-phosphate group of an incoming deoxynucleotide, such that the overall direction of synthesis is in the 5' to 3' direction. 3' flap cleavage may be measured in a DNA synthesis reaction in which, because the (labeled) 3' end of a DNA duplex is unpaired, it is cleaved from the duplex. A FEN nuclease that "consists of" a 5' exonuclease and/or endonuclease activity refers to an enzyme that "lacks" 5' to 3' synthetic activity and/or 3' single-stranded flap cleavage activity. "Lacks" means that the Fen nuclease has no detectable activity or has only "minor" activity, i.e., less than 1.0%, 0.5%, 0.1% or 0.01% of the activity of a wild type enzyme. As used herein, "FEN nuclease" encompasses a 5' flap-specific nuclease.

The term "FEN nuclease" also embodies a 5' flap-specific nuclease. A nuclease or cleavage agent according to the invention includes but is not limited to a FEN nuclease enzyme derived from *Archaeglobus fulgidus, Methanococcus jannaschii, Pyrococcus furiosus*, human, mouse or *Xenopus laevis*.

As used herein, "wild type" refers to a gene or gene product which has the characteristics of (i.e., either has the sequence of or encodes, for the gene, or possesses the sequence or activity of, for an enzyme) that gene or gene product when isolated from a naturally occurring source.

A "5' flap-specific nuclease" (also referred to herein as a "flap-specific nuclease") according to the invention is an endonuclease which can remove a single stranded flap that protrudes as a 5' single strand. A flap-specific nuclease according to the invention can also cleave a pseudo-Y structure. A substrate of a flap-specific nuclease according to the invention, comprises a target nucleic acid, a second nucleic acid, a portion of which specifically hybridizes with a target nucleic acid, and a primer extension product from a third nucleic acid that specifically hybridizes with a target nucleic acid sequence.

As used herein, a "cleavage structure" refers to a polynucleotide structure (for example as illustrated in FIG. 1) comprising at least a duplex nucleic acid having a single stranded region comprising a flap, a loop, a single-stranded bubble, a D-loop, a nick or a gap. A cleavage structure according to the invention thus includes a polynucleotide structure comprising a flap strand of a branched DNA wherein a 5' single-stranded polynucleotide flap extends from a position near its junction to the double stranded portion of the structure. In some embodiments, the flap is labeled with a detectable label. A flap of a cleavage structure according to the invention is preferably about 1-10,000 nucleotides, more preferably about 5-25 nucleotides and most preferably about 10-20 nucleotides and is preferably cleaved at a position located at the phosphate positioned at the "elbow" of the branched structure or at any of one to ten phosphates located proximal and/or distal from the elbow of the flap strand. As used herein, "elbow" refers to the phosphate bond between the first single stranded nucleotide of the 5' flap and the first double stranded (e.g., hybridized to the target nucleic acid) nucleotide. In one embodiment, a flap of a cleavage structure cannot hybridize to a target nucleic acid.

A cleavage structure according to the invention preferably comprises a target nucleic acid sequence, and also may include an oligonucleotide that specifically hybridizes with the target nucleic acid sequence, and a flap extending from the hybridizing oligonucleotide. For example, a cleavage structure according to the invention may comprise a target nucleic acid sequence (for example B in FIG. 3), an upstream oligonucleotide that is complementary to the target sequence (for example A in FIG. 3), and a downstream oligonucleotide that is complementary to the target sequence (for example C in FIG. 3). In such a cleavage structure, the downstream oligonucleotide may be blocked at the 3' terminus to prevent extension of the 3' end of the downstream oligonucleotide. In such a cleavage structure the upstream oligonucleotide may be blocked (for example X in FIG. 13).

A cleavage structure according to the invention may be a polynucleotide structure comprising a flap extending from the downstream oligonucleotide, wherein the flap is formed by extension of the upstream oligonucleotide by the synthetic activity of a nucleic acid polymerase, and subsequent, partial, displacement of the 5' end of the downstream oligonucleotide. In yet another embodiment, the cleavage structure according to the invention comprises a pre-formed flap extending from the downstream oligonucleotide, wherein the flap is fumed by a 5' portion of the downstream oligonucleotide which is non-complementary to the target.

A cleavage structure according to the invention may be formed by hybridizing a target nucleic acid sequence with an oligonucleotide wherein the oligonucleotide comprises a complementary region that anneals to the target nucleic acid sequence, and a non-complementary region that does not anneal to the target nucleic acid sequence and forms a 5' flap.

In another embodiment of the invention, a cleavage structure according to the invention can be prepared by incubating a target nucleic acid with a downstream oligonucleotide probe having a secondary structure that changes upon binding of the probe to the target nucleic acid, and further comprising a binding moiety and a non-complementary 5' region that does not anneal to the target nucleic acid and forms a 5' flap and a complementary 3' region that anneals to the target nucleic acid, and an upstream oligonucleotide. In one embodiment, the upstream oligonucleotide and the downstream probe hybridize to non-overlapping regions of the target nucleic acid. In another embodiment, the upstream oligonucleotide and the downstream probe hybridize to adjacent regions of the target nucleic acid.

A cleavage structure also may be a pseudo-Y structure wherein a pseudo Y-structure is formed if the strand upstream of a flap (referred to herein as a flap adjacent strand or primer strand) is removed, and double stranded DNA substrates containing a gap or nick. A "cleavage structure", as used herein, does not include a double stranded nucleic acid structure with only a 3' single-stranded flap. As used herein, a "cleavage structure" comprises ribonucleotides or deoxyribonucleotides and thus can be RNA or DNA.

A cleavage structure according to the invention may be an overlapping flap wherein the 3' end of an upstream oligonucleotide capable of hybridizing to a target nucleic acid sequence (for example A in FIG. 3) is complementary to 1 base pair of the downstream oligonucleotide (for example C in FIG. 3) that is annealed to a target nucleic acid sequence and wherein the overlap is directly downstream of the point of extension of the single stranded flap.

A cleavage structure according to the invention is formed by the steps of 1: incubating a) an upstream extendable 3' end, preferably an oligonucleotide primer, b) an oligonucleotide primer probe located not more than 5000 nucleotides downstream of the upstream primer and c) an appropriate target nucleic acid sequence wherein the target sequence is complementary to both the upstream primer and downstream probe and d) a suitable buffer, under conditions that allow the nucleic acid sequence to hybridize to the oligonucleotide primers, and 2: extending the 3' end of the upstream oligonucleotide primer by the synthetic activity of a polymerase such that the newly synthesized 3' end of the upstream oligonucleotide primer becomes adjacent to and/or displaces at least a portion of (i.e., at least 5-10 nucleotides of) the 5' end of the downstream oligonucleotide probe. According to the method of the invention, buffers and extension temperatures are favorable for strand displacement by a particular nucleic acid polymerase according to the invention. Preferably, the downstream oligonucleotide is blocked at the 3' terminus to prevent extension of the 3' end of the downstream oligonucleotide. In another embodiment of the invention, a cleavage structure according to the invention can be prepared by incubating a target nucleic acid sequence with an oligonucleotide primer comprising a non-complementary 5' region that does not anneal to the target nucleic acid sequence and forms a 5' flap, and a complementary 3' region that anneals to the target nucleic acid sequence.

In a preferred embodiment of the invention a cleavage structure is labeled. A labeled cleavage structure according to the invention is formed by the steps of 1: incubating a) an upstream extendable 3' end, preferably an oligonucleotide primer, b) a labeled probe preferably located not more than 5000 and more preferably located not more than 500 nucleotides downstream of the upstream primer and c) an appropriate target nucleic acid sequence wherein the target sequence is complementary to both the primer and the labeled probe and d) a suitable buffer, under conditions that allow the nucleic acid sequence to hybridize to the primers, and 2: extending the 3' end of the upstream primer by the synthetic activity of a polymerase such that the newly synthesized 3' end of the upstream primer partially displaces the 5' end of the downstream probe. According to the method of the invention, buffers and extension temperatures are favorable for strand displacement by a particular nucleic acid polymerase according to the invention. Preferably, the downstream oligonucleotide is blocked at the 3' terminus to prevent extension of the 3' end of the downstream oligonucleotide. In another embodiment, a cleavage structure according to the invention can be prepared by incubating a target nucleic acid sequence with a probe comprising a non-complementary, labeled, 5' region that does not anneal to the target nucleic acid sequence and forms a 5' flap, and a complementary 3' region that anneals to the target nucleic acid sequence.

In another embodiment, the cleavage structure is formed as depicted in FIG. 13 and described in Example 7. The cleavage structure comprises an upstream oligonucleotide (X) with a "blocked 3' end", shown as "3'B", a target nucleic acid and a downstream probe (A) with a 5' flap. In some embodiments, the 3' nucleotide of the upstream oligonucleotide is between 0-20 bases from the 5' terminal hybridized nucleotide of the downstream oligonucleotide. In other embodiments, the 3' nucleotide of the upstream oligonucleotide is between 0-10 bases from the 5' terminal hybridized nucleotide of the downstream oligonucleotide. In yet other embodiments, the 3' nucleotide of the upstream oligonucleotide is between 0-5 bases from the 5' terminal hybridized nucleotide of the downstream oligonucleotide. In a further embodiment, a nick separates the upstream and downstream oligonucleotides.

In other embodiments, the blocked 3' end of the upstream oligonucleotide can either be upstream of, at, or downstream of the 5' terminal hybridized nucleotide of the downstream oligonucleotide.

As used herein, "label" or "labeled moiety capable of providing a signal" refers to any atom or molecule which can be used to provide a detectable (preferably quantifiable) signal, and which can be operatively linked to a nucleic acid. Labels may provide signals detectable by fluorescence, radioactivity, colorimetry, gravimetry, X-ray diffraction or absorption, magnetism, enzymatic activity, mass spectrometry, binding affinity, hybridization radiofrequency and the like.

As used herein, "generating a signal" refers to detecting and or measuring a released nucleic acid fragment as an indication of the presence of a target nucleic acid sequence in a sample.

As used herein, "sample" refers to any substance containing or presumed to contain a nucleic acid of interest (a target nucleic acid sequence) or which is itself a nucleic acid containing or presumed to contain a target nucleic acid sequence of interest. The term "sample" thus includes a sample of nucleic acid (genomic DNA, cDNA, RNA), cell, organism, tissue, fluid, or substance including but not limited to, for example, plasma, serum, spinal fluid, lymph fluid, synovial fluid, urine, tears, stool, external secretions of the skin, respiratory, intestinal and genitourinary tracts, saliva, blood cells, tumors, organs, tissue, samples of in vitro cell culture constituents, natural isolates (such as drinking water, seawater, solid materials), microbial specimens, and objects or specimens that have been "marked" with nucleic acid tracer molecules.

As used herein, "target nucleic acid sequence" or "template nucleic acid sequence" refers to a region of a nucleic acid that is to be either replicated, amplified, and/or detected. In one embodiment, the "target nucleic acid sequence" or "template nucleic acid sequence" resides between two primer sequences used for amplification.

As used herein, "nucleic acid polymerase" refers to an enzyme that catalyzes the polymerization of nucleoside triphosphates. Generally, the enzyme will initiate synthesis at the 3'-end of the primer annealed to the target sequence, and will proceed in the 5'-direction along the template, and if possessing a 5' to 3' nuclease activity, hydrolyzing intervening, annealed probe to release both labeled and unlabeled probe fragments, until synthesis terminates. Known DNA polymerases include, for example, E. coli DNA polymerase I, T7 DNA polymerase, *Thermus thermophilus* (Tth) DNA polymerase, *Bacillus stearothermophilus* DNA polymerase, *Thermococcus litoralis* DNA polymerase, *Thermus aquaticus* (Taq) DNA polymerase and *Pyrococcus furiosus* (Pfu) DNA polymerase.

As used herein, "5' to 3' exonuclease activity" or "5' to 3' exonuclease activity" refers to that activity of a template-specific nucleic acid polymerase e.g. a 5' to 3' exonuclease activity traditionally associated with some DNA polymerases whereby mononucleotides or oligonucleotides are removed from the 5' end of a polynucleotide in a sequential manner, (i.e., E. coli DNA polymerase I has this activity whereas the Klenow (Klenow et al., 1970, *Proc. Natl. Acad. Sci., USA,* 65:168) fragment does not, (Klenow et al., 1971, *Eur. J. Biochem.,* 22:371)), or polynucleotides are removed from the 5' end by an endonucleolytic activity that may be inherently present in a 5' to 3' exonuclease activity.

As used herein, the phrase "substantially lacks 5' to 3' exonuclease activity" or "substantially lacks 5' to 3' exonuclease activity" means having less than 10%, 5%, 1%, 0.5%, or 0.1% of the activity of a wild type enzyme. The phrase "lacking 5' to 3' exonuclease activity" or "lacking 5' to 3' exonuclease activity" means having undetectable 5' to 3' exonuclease activity or having less than about 1%, 0.5%, or 0.1% of the 5' to 3' exonuclease activity of a wild type enzyme. 5' to 3' exonuclease activity may be measured by an exonuclease assay which includes the steps of cleaving a nicked substrate in the presence of an appropriate buffer, for example 10 mM Tris-HCl (pH 8.0), 10 mM $MgCl_2$ and 50 µg/ml bovine serum albumin) for 30 minutes at 60° C., terminating the cleavage reaction by the addition of 95% formamide containing 10 mM EDTA and 1 mg/ml bromophenol blue, and detecting nicked or un-nicked product.

Nucleic acid polymerases useful according to the invention include but are not limited to Pfu, exo-Pfu (a mutant form of Pfu that lacks 3' to 5' exonuclease activity), the Stoffel fragment of Taq, N-truncated Bst, N-truncated Bca, Genta, JdF3 exo-, Vent, Vent exo- (a mutant form of Vent that lacks 3' to 5' exonuclease activity), Deep Vent, Deep Vent exo- (a mutant form of Deep Vent that lacks 3' to 5' exonuclease activity), U1Tma and Sequenase. Additional nucleic acid polymerases useful according to the invention are included below in the section entitled, "Nucleic Acid Polymerases".

As used herein, "cleaving" refers to enzymatically separating a cleavage structure into distinct (i.e. not physically linked to other fragments or nucleic acids by phosphodiester bonds) fragments or nucleotides and fragments that are released from the cleavage structure. For example, cleaving a labeled cleavage structure refers to separating a labeled cleavage structure according to the invention and defined below, into distinct fragments including fragments derived from an oligonucleotide that specifically hybridizes with a target nucleic acid sequence or wherein one of the distinct fragments is a labeled nucleic acid fragment derived from a target nucleic acid sequence and/or derived from an oligonucleotide that specifically hybridizes with a target nucleic acid sequence that can be detected and/or measured by methods well known in the art and described herein that are suitable for detecting the labeled moiety that is present on a labeled fragment.

As used herein, "endonuclease" refers to an enzyme that cleaves bonds, preferably phosphodiester bonds, within a nucleic acid molecule. An endonuclease according to the invention can be specific for single-stranded or double-stranded DNA or RNA.

As used herein, "exonuclease" refers to an enzyme that cleaves bonds, preferably phosphodiester bonds, between nucleotides one at a time from the end of a polynucleotide. An exonuclease according to the invention can be specific for the 5' or 3' end of a DNA or RNA molecule, and is referred to herein as a 5' exonuclease or a 3' exonuclease.

As used herein a "flap" refers to a region of single stranded DNA that extends from a double stranded nucleic acid molecule. A flap according to the invention is preferably between about 1-500 nucleotides, more preferably between about 5-25 nucleotides and most preferably between about 10-20 nucleotides.

In a preferred embodiment, the nucleic acid polymerase substantially -lacks 5' to 3' exonuclease activity.

In a preferred embodiment, the cleavage structure comprises at least one oligonucleotide primer.

The invention also provides a method of detecting or measuring a target nucleic acid sequence comprising forming a cleavage structure by incubating a sample comprising a target nucleic acid sequence with a nucleic acid polymerase, cleaving the cleavage structure with a FEN nuclease to release a nucleic acid fragment, and detecting and/or measuring the release of the fragment as an indication of the presence of the target sequence in the sample.

As used herein, "detecting a target nucleic acid sequence" or "measuring a target nucleic acid sequence" refers to determining the presence of a particular target nucleic acid sequence in a sample or determining the amount of a particular target nucleic acid sequence in a sample as an indication of the presence of a target nucleic acid sequence in a sample. The amount of a target nucleic acid sequence that can be measured or detected is preferably about 1 molecule to $10^{20}$ molecules, more preferably about 100 molecules to $10^{17}$ molecules and most preferably about 1000 molecules to $10^{14}$ molecules. According to the invention, the detected nucleic acid is derived from the labeled 5' end of a downstream probe of a cleavage structure according to the invention (for example C in FIG. 3), that is displaced from the target nucleic acid sequence by the 3' extension of an upstream probe of a cleavage structure according to the invention (for example A of FIG. 3). According to the present invention, a label is attached to the 5' end of the downstream probe (for example C in FIG. 3) comprising a cleavage structure according to the invention. Alternatively, a label is attached to the 3' end of the downstream probe and a quencher is attached to the 5' flap of the downstream probe. According to the invention, a label may be attached to the 3' end of the downstream probe (for example C in FIG. 3) comprising a cleavage structure according to the invention.

According to the invention, the downstream probe (for example C in FIG. 3) may be labeled internally. In a preferred embodiment, a cleavage structure according to the invention can be prepared by incubating a target nucleic acid sequence with a probe comprising a non-complementary, labeled, 5' region that does not anneal to the target nucleic acid sequence and forms a 5' flap, and a complementary 3' region that anneals to the target nucleic acid sequence. According to this embodiment of the invention, the detected nucleic acid is derived from the labeled 5' flap region of the probe. Preferably there is a direct correlation between the amount of the target nucleic acid sequence and the signal generated by the cleaved, detected nucleic acid.

As used herein, "detecting release of labeled fragments" or "measuring release of labeled fragments" refers to determining the presence of a labeled fragment in a sample or determining the amount of a labeled fragment in a sample. Methods well known in the art and described herein can be used to detect or measure release of labeled fragments. A method of detecting or measuring release of labeled fragments will be appropriate for measuring or detecting the labeled moiety that is present on the labeled fragments. The amount of a released labeled fragment that can be measured or detected is preferably about 25%, more preferably about 50% and most preferably about 95% of the total starting amount of labeled probe.

As used herein, "labeled fragments" refer to cleaved mononucleotides or small oligonucleotides or oligonucleotides derived from the labeled cleavage structure according to the invention wherein the cleaved oligonucleotides are preferably between about 2-1000 nucleotides, more preferably between about 5-50 nucleotides and most preferably between about 16-18 nucleotides, which are cleaved from a cleavage structure by a FEN nuclease and can be detected by methods well known in the art and described herein.

As used herein, "detecting the released non-complementary 5' flap" or "measuring the released non-complementary 5' flap" refers to determining the presence of a cleaved 5' flap in a sample or determining the amount of a cleaved 5' flap in a sample. Methods well known in the art and described herein can be used to detect or measure release of nucleic acid fragments. The cleaved 5' flap can be detected directly, e.g., fluorescent signal from a FRET pair, or indirectly, e.g., secondary cleavage or amplification reaction. (See other related patents, the disclosures of which are incorporated herein by reference for direct detection (U.S. patent application Ser. No. 10/981,942, filed Nov. 5, 2004; U.S. Pat. No. 6,528,254 B1, filed Oct. 29, 1999; U.S. Pat. No. 6,548,250, filed Aug. 30, 2000) and indirect detection (U.S. Pat. No. 6,893,819, filed Nov. 21, 2000; U.S. Application 60/725,916, filed Oct. 11, 2005.)

As used herein, "released 5' flaps" refer to cleaved small oligonucleotides or oligonucleotides derived from the cleavage structure according to the invention wherein the cleaved oligonucleotides are preferably between about 2-1000 nucleotides, more preferably between about 5-50 nucleotides and most preferably between about 16-18 nucleotides, which are cleaved from a cleavage structure by a nuclease and can be detected by methods well known in the art and described herein.

In a preferred embodiment, the nucleic acid polymerase substantially lacks 5' to 3' exonuclease activity.

In another preferred embodiment, the nucleic acid polymerase is a DNA polymerase.

In another preferred embodiment, the nucleic acid polymerase is thermostable.

As used herein, "thermostable" refers to an enzyme which is stable and active at temperatures as great as preferably between about 90-100° C. and more preferably between about 70-98° C. to heat as compared, for example, to a non-thermostable form of an enzyme with a similar activity. For example, a thermostable nucleic acid polymerase or FEN nuclease derived from thermophilic organisms such as *P. furiosus, M jannaschii, A. fulgidus* or *P. horikoshii* are more stable and active at elevated temperatures as compared to a nucleic acid polymerase from *E. coli* or a mammalian FEN enzyme. A representative thermostable nucleic acid polymerase isolated from *Thermus aquaticus* (Taq) is described in U.S. Pat. No. 4,889,818 and a method for using it in conventional PCR is described in Saiki et al., 1988, *Science* 239:487. Another representative thermostable nucleic acid polymerase isolated from *P. furiosus* (Pfu) is described in Lundberg et al., 1991, *Gene,* 108:1-6. Additional representative temperature stable polymerases include, e.g., polymerases extracted from the thermophilic bacteria *Thermus flavus, Thermus ruber, Thermus thermophilus, Bacillus stearothermophilus* (which has a somewhat lower temperature optimum than the others listed), *Thermus lacteus, Thermus rubens, Thermotoga maritima,* or from thermophilic archaea *Thermococcus litoralis,* and *Methanothermus fervidus.*

Temperature stable polymerases and FEN nucleases are preferred in a thermocycling process wherein double stranded nucleic acids are denatured by exposure to a high temperature (about 95° C.) during the PCR cycle.

In another preferred embodiment, the FEN nuclease is a flap-specific nuclease.

In another preferred embodiment, the FEN nuclease is thermostable.

In another preferred embodiment, the cleavage structure is formed comprising at least one labeled moiety capable of providing a signal.

In another preferred embodiment, the cleavage structure is formed comprising a pair of interactive signal generating labeled moieties effectively positioned to quench the generation of a detectable signal, wherein the labeled moieties are separated by a site susceptible to FEN nuclease cleavage, thereby allowing the nuclease activity of the FEN nuclease to separate the first interactive signal generating labeled moiety from the second interactive signal generating labeled moiety by cleaving at the site susceptible to FEN nuclease, thereby generating a detectable signal.

In yet another preferred embodiment, the cleavage structure is formed comprising a hairpin-forming oligonucleotide probe having secondary structure.

As used herein, "secondary structure" refers to the conformation (for example a hairpin, a stem-loop structure, an internal loop, a bulge loop, a branched structure, or a pseudoknot) of a nucleic acid molecule wherein a sequence comprising a first single stranded sequence of bases followed by a second complementary sequence in the same molecule folds back on itself to generate an antiparallel duplex structure wherein the single stranded sequence and the complementary sequence anneal by the formation of hydrogen bonds. A "secondary structure" also refers to the conformation of a nucleic acid molecule comprising an affinity pair, wherein the affinity pair reversibly associates as a result of attractive forces that exist between the moieties. As used herein, "secondary structure" refers to a nucleic acid conformation which prevents probe binding to a capture element. Probes utilizing secondary structures in cleavage reactions are described in related U.S. application Ser. No. 09/728,574, which was filed on Nov. 30, 2000 and is herein incorporated by reference in its entirety.

As used herein, a "hairpin structure" or a "stem" refers to a double-helical region formed by base pairing between adjacent, inverted, complementary sequences in a single strand of RNA of DNA.

As used herein, "stem loop" structure refers to a hairpin structure, further comprising a loop of unpaired bases at one end.

In another preferred embodiment, the pair of interactive signal generating moieties comprises a quencher moiety and a fluorescent moiety.

In another preferred embodiment, the cleavage structure comprises at least one oligonucleotide primer.

The invention also provides a polymerase chain reaction process for detecting a target nucleic acid sequence in a sample comprising providing a cleavage structure, providing a set of oligonucleotide primers wherein a first primer contains a sequence complementary to a region in one strand of the target nucleic acid sequence and primes the synthesis of a complementary DNA strand, and a second primer contains a sequence complementary to a region in a second strand of the target nucleic acid sequence and primes the synthesis of a complementary DNA strand, and amplifying the target nucleic acid sequence employing a nucleic acid polymerase as a template-dependent polymerizing agent under conditions which are permissive for PCR cycling steps of (i) annealing of primers required for amplification to a template nucleic acid sequence contained within the target sequence and annealing primers required for formation of a cleavage structure to a target nucleic acid sequence, (ii) extending the primers wherein the nucleic acid polymerase synthesizes a primer extension product, and (iii) cleaving the cleavage structure employing a FEN nuclease as a cleavage agent for release of labeled fragments from the cleavage structure thereby creating detectable labeled fragments; and (d) detecting and/or measuring the release of labeled fragments as an indication of the presence of the target nucleic acid sequence in the sample.

The invention provides for a polymerase chain reaction process wherein amplification and detection of a target nucleic acid sequence occur concurrently (i.e. real time detection). The invention also provides for a polymerase chain reaction process wherein amplification of a target nucleic acid sequence occurs prior to detection of the target nucleic acid sequence (i.e. end point detection).

As used herein, an "oligonucleotide primer" or "extension primer" refers to a single stranded DNA or RNA molecule that can hybridize to a nucleic acid template and primes enzymatic synthesis of a second nucleic acid strand. Oligonucleotide primers useful according to the invention are between about 10 to 100 nucleotides in length, preferably about 17-50 nucleotides in length and more preferably about 17-45 nucleotides in length.

As used herein, a "probe" refers to a single stranded nucleic acid comprising a region or regions that are complementary to a target nucleic acid (e.g., target nucleic acid binding sequences). A "probe" according to the invention binds to a target nucleic acid to form a cleavage structure that can be cleaved by a nuclease, wherein cleaving is performed at a cleaving temperature. A probe according to the invention cannot be cleaved to generate a signal by a "nuclease", as defined herein, prior to binding to a target nucleic acid. In some embodiments, a "probe" according to the invention has a secondary structure that changes upon binding of the probe to the target nucleic acid and may further comprises a binding moiety. In one embodiment of the invention, a probe may comprise a region that cannot bind or is not complementary to a target nucleic acid. In some embodiments, the probe has a blocked 3' end to prevent extension by a polymerase.

Oligonucleotide probes useful for the formation of a cleavage structure according to the invention are between about 17-40 nucleotides in length, preferably about 17-30 nucleotides in length and more preferably about 17-25 nucleotides in length.

Oligonucleotide probes, as used in the present invention include oligonucleotides comprising secondary structure, including, but not limited to molecular beacons, safety pins (FIG. 10), scorpions (FIG. 11), and sunrise/amplifluor probes (FIG. 12), the details and structures of which are described below and in the corresponding Figures.

As used herein, "template dependent polymerizing agent" refers to an enzyme capable of extending an oligonucleotide primer in the presence of adequate amounts of the four deoxyribonucleoside triphosphates (dATP, dGTP, dCTP and dTTP) or analogs as described herein, in a reaction medium comprising appropriate salts, metal cations, appropriate stabilizers and a pH buffering system. Template dependent polymerizing agents are enzymes known to catalyze primer- and template-dependent DNA synthesis, and possess 5' to 3' nuclease activity. Preferably, a template dependent polymerizing agent according to the invention lacks 5' to 3' nuclease activity.

As used herein, "amplifying" refers to producing additional copies of a nucleic acid sequence, including the method of the polymerase chain reaction.

In a preferred embodiment, the nucleic acid polymerase substantially lacks 5' to 3' exonuclease activity.

In a preferred embodiment, the oligonucleotide primers of step b of the polymerase chain reaction process described above are oriented such that the forward primer is located upstream of a cleavage structure according to the invention and the reverse primer is located downstream of a cleavage structure according to the invention. The reverse primer is complementary to the opposite strand of the forward primer which is complementary to a strand of the cleavage structure.

In another preferred embodiment, the nucleic acid polymerase is a DNA polymerase.

In another preferred embodiment, the nucleic acid polymerase is thermostable.

In another preferred embodiment, the nucleic acid polymerase is selected from the group consisting of Taq polymerase and Pfu polymerase.

In another preferred embodiment the FEN nuclease is thermostable.

In another preferred embodiment the FEN nuclease is a flap-specific nuclease.

In another preferred embodiment the FEN nuclease is selected from the group consisting of FEN nuclease enzyme derived from *Archaeglobus fulgidus, Methanococcus jannaschii, Pyrococcus furiosus*, human, mouse or *Xenopus laevis*. A nuclease according to the invention also includes *Saccharomyces cerevisiae* RAD27, and *Schizosaccharomyces pombe* RAD2, Pol I DNA polymerase associated 5' to 3' exonuclease domain, (e.g. *E. coli, Thermus aquaticus* (Taq), *Thermus flavus* (Tfl), *Bacillus caldotenax* (Bca), *Streptococcus pneumoniae*) and phage functional homologs of FEN including but not limited to T4 RNaseH, T5 5' to 3' exonuclease, T7 gene 6 exonuclease and T3 gene 6 exonuclease.

Preferably, only the 5' to 3' exonuclease domains of Taq, Tfl and Bca FEN nuclease are used.

In another preferred embodiment, the labeled cleavage structure is formed by the addition of at least one labeled moiety capable of providing a signal.

The invention also provides a polymerase chain reaction process for simultaneously forming a cleavage structure, amplifying a target nucleic acid sequence in a sample and cleaving the cleavage structure comprising: (a) providing an upstream oligonucleotide primer complementary to a region in one strand of the target nucleic acid sequence and a downstream labeled probe complementary to a region in the same strand of the target nucleic acid sequence, wherein the upstream primer contains a sequence complementary to a region in one strand of the target nucleic acid sequence and primes the synthesis of a complementary DNA strand, and the downstream probe contains a sequence complementary to a region in a second strand of the target nucleic acid sequence and primes the synthesis of a complementary DNA strand; and (b) detecting a nucleic acid which is produced in a reaction comprising amplification of the target nucleic acid sequence and cleavage thereof wherein a nucleic acid polymerase is a template-dependent polymerizing agent under conditions which are permissive for PCR cycling steps of (i) annealing of primers to a target nucleic acid sequence, (ii) extending the primers of step (a) wherein the nucleic acid polymerase synthesizes primer extension products, and wherein the primer extension product of the primer of step (a) partially displaces the downstream probe of step (a) to form a cleavage structure; and (iii) cleaving the cleavage structure employing a FEN nuclease as a cleavage agent for release of labeled fragments from the cleavage structure thereby creating detectable labeled fragments.

In a preferred embodiment, the nucleic acid polymerase substantially lacks 5' to 3' exonuclease activity.

The invention also provides a method of forming a cleavage structure comprising the steps of: (a) providing a target nucleic acid sequence, (b) providing an upstream primer complementary to said target nucleic acid sequence, (c) providing a downstream probe complementary to said target nucleic acid sequence, (d) extending the 3' end of the upstream primer with a nucleic acid polymerase; and (e) displacing the 5' end of the downstream probe.

Preferably the downstream probe is located not more than 500 nucleotides downstream of the upstream primer.

During the extension step, the 3' end of the upstream primer is extended by the synthetic activity of a polymerase such that the newly synthesized 3' end of the upstream primer partially displaces the 5' end of the downstream probe.

In a preferred embodiment, the nucleic acid polymerase substantially lacks 5' to 3' exonuclease activity.

In another embodiment of the invention, a cleavage structure according to the invention can be prepared by incubating a target nucleic acid sequence with a probe comprising a non-complementary 5' region that does not anneal to the target nucleic acid sequence and forms a 5' flap, and a complementary 3' region that anneals to the target nucleic acid sequence.

The invention also provides a method of forming a labeled cleavage structure comprising the steps of: (a) providing a target nucleic acid sequence, (b) providing an upstream primer complementary to said target nucleic acid sequence, (c) providing a downstream end labeled probe complementary to said target nucleic acid sequence, (d) extending the 3' end of the upstream primer with a nucleic acid polymerase; and (e) displacing the 5' end of the downstream probe.

Preferably the downstream end labeled probe is located not more than 500 nucleotides downstream of the upstream primer. Preferably, the downstream oligonucleotide is blocked at the 3' terminus to prevent extension of the 3' end of the downstream oligonucleotide. Such blockage can be achieved by placing a phosphate, or other moiety not readily removed, on the 3' terminal hydroxyl of the oligonucleotide.

During the extension step, the 3' end of the upstream primer is extended by the synthetic activity of a polymerase such that the newly synthesized 3' end of the upstream primer partially displaces the 5' end of the downstream probe. According to the method of the invention, buffers and extension temperatures are favorable for strand displacement by a particular nucleic acid polymerase according to the invention.

In one embodiment of the invention, a cleavage structure according to the invention can be prepared by incubating a target nucleic acid sequence with a probe comprising a non-complementary, labeled, 5' region that does not anneal to the target nucleic acid sequence and forms a 5' flap, and a complementary 3' region that anneals to the target nucleic acid sequence.

The invention also provides a kit for generating a signal indicative of the presence of a target nucleic acid sequence in a sample comprising a nucleic acid polymerase, a FEN nuclease and a suitable buffer. In a preferred embodiment, the invention also provides a kit for generating a signal indicative of the presence of a target nucleic acid sequence in a sample comprising one or more nucleic acid polymerases, a FEN nuclease and a suitable buffer.

In a preferred embodiment, the nucleic acid polymerase substantially lacks 5' to 3' exonuclease activity.

In a preferred embodiment the nucleic acid polymerase is thermostable.

In another preferred embodiment the FEN nuclease is thermostable.

In another preferred embodiment the kit further comprises a labeled nucleic acid complementary to the target nucleic acid sequence.

The invention also provides a composition comprising a nucleic acid polymerase and a FEN nuclease.

In a preferred embodiment, the nucleic acid polymerase substantially lacks a 5' to 3' exonuclease activity.

In another preferred embodiment the invention provides for a composition comprising one or more nucleic acid polymerases and a FEN nuclease.

Further features and advantages of the invention are as follows. The claimed invention provides a method of generating a signal to detect and/or measure a target nucleic acid wherein the generation of a signal is an indication of the presence of a target nucleic acid in a sample. The method of the claimed invention does not require multiple steps. The claimed invention also provides a PCR based method for detecting and/or measuring a target nucleic acid comprising generating a signal as an indication of the presence of a target nucleic acid. The claimed invention allows for simultaneous amplification and detection and/or measurement of a target nucleic acid sequence. The claimed invention also provides a PCR based method for detecting and/or measuring a target nucleic acid comprising generating a signal in the absence of a nucleic acid polymerase that demonstrates 5' to 3' exonuclease activity.

Further features and advantages of the invention will become more fully apparent in the following description of the embodiments and drawings thereof, and from the claims.

DETAILED DESCRIPTION OF THE INVENTION

Figure 1:
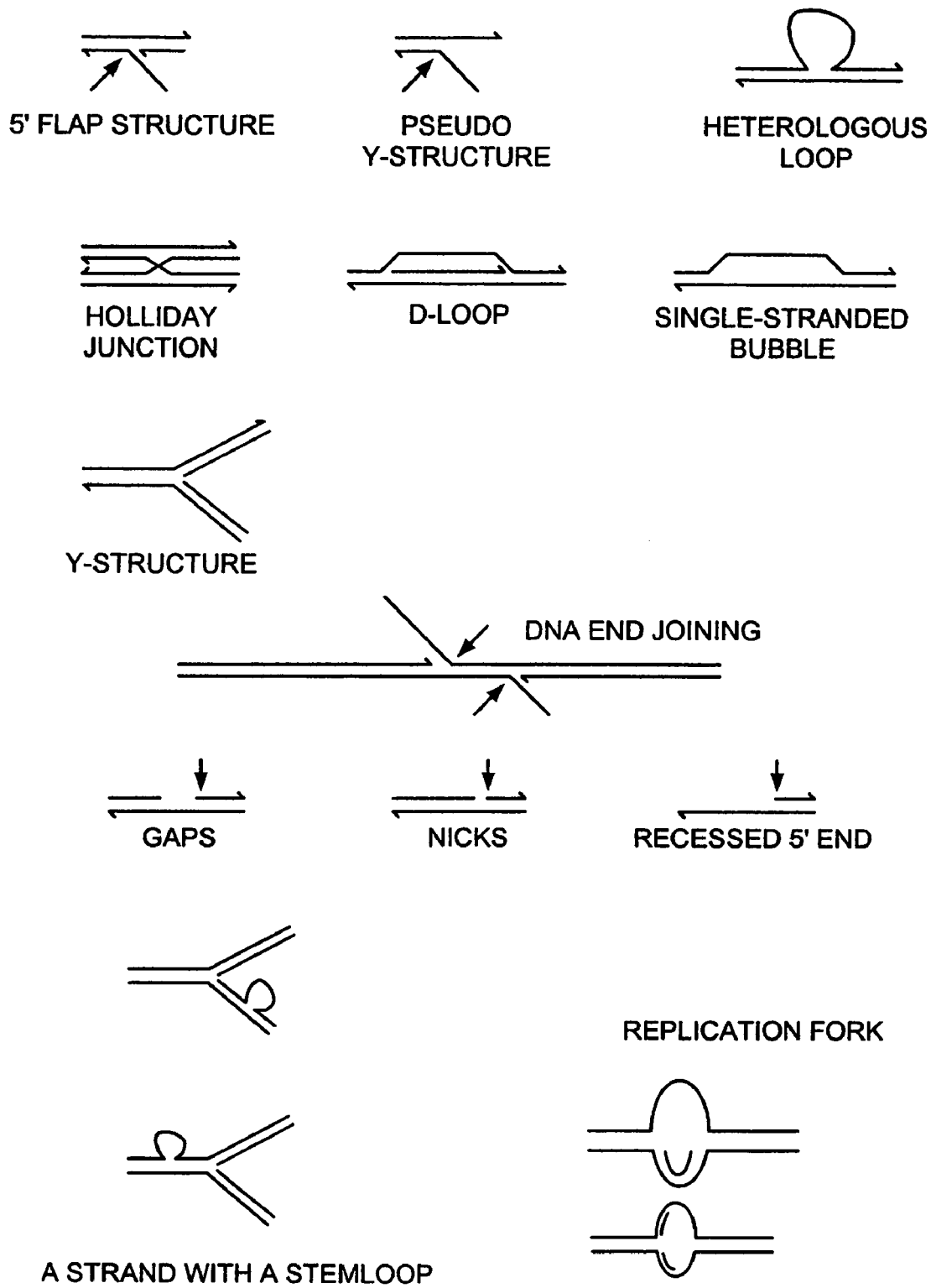
FIG. 1 demonstrates FEN nuclease cleavage structures.

The invention provides for a method of generating a signal to detect the presence of a target nucleic acid in a sample wherein a nucleic acid is treated with the combination of a nucleic acid polymerase and a FEN nuclease. The invention also provides for a process for detecting or measuring a nucleic acid that allows for concurrent amplification, cleavage and detection of a target nucleic acid sequence in a sample.

The practice of the present invention will employ, unless otherwise indicated, conventional techniques of molecular biology, microbiology and recombinant DNA techniques, which are within the skill of the art. Such techniques are explained fully in the literature. See, e.g., Sambrook, Fritsch & Maniatis, 1989, *Molecular Cloning: A Laboratory Manual*, Second Edition; *Oligonucleotide Synthesis* (M. J. Gait, ed., 1984); *Nucleic Acid Hybridization* (B. D. Harnes & S. J. Higgins, eds., 1984); *A Practical Guide to Molecular Cloning* (B. Perbal, 1984); and a series, *Methods in Enzymology* (Academic Press, Inc.). All patents, patent applications, and publications mentioned herein, both supra and infra, are hereby incorporated by reference.

The invention provides a method of generating a signal indicative of the presence of a target nucleic acid in a sample, which includes the steps of forming a cleavage structure by incubating a sample containing a target nucleic acid with a probe, forming a cleavage structure by incubating a sample comprising a target nucleic acid sequence with a nucleic acid polymerase, and cleaving the cleavage structure with a nuclease to release a nucleic acid fragment and thus generate a signal. Generation of the signal is indicative of the presence of a target nucleic acid in the sample, and the signal may be detected or measured by directly detecting and/or measuring the amount of a fragment or indirectly detecting and/or measuring the amount of the fragment.

The present invention provides a method for detecting the presence of a target nucleic acid, wherein the method comprises:

a) providing:
  a target nucleic acid, which comprises in the 3' to 5' order a first hybridization site and a second hybridization site;
  an upstream oligonucleotide that is complementary to the first hybridization site and wherein the upstream oligonucleotide has a blocked 3' end, and
  a downstream probe comprising a 5' region and a 3' region, wherein the 3' region is complementary to the second hybridization site and the 5' forms a non-complementary 5' flap when the downstream probe is annealed to the target;

b) annealing the upstream oligonucleotide and the downstream probe to the target nucleic acid to form a cleavage structure;

c) cleaving the cleavage structure with a nuclease to release the non-complementary 5' flap; and d) detecting the released non-complementary 5' flap, wherein the released non-complementary 5' flap is indicative of the presence of the target nucleic acid in the sample.

In one embodiment, the non-complementary 5' flap of the downstream probe consists of n nucleotides and the first hybridization site and the second hybridization site are separated by m-nucleotides, wherein n is an integer from 1 to 25 and m is an integer greater than n.

In another embodiment, a cleavage structure is formed comprising at least one labeled moiety capable of providing a signal.

In another embodiment, the nuclease comprises a FEN nuclease. Preferably, the FEN nuclease is a flap-specific nuclease and/or is thermostable. More preferably, it is selected from the group consisting of FEN nuclease enzyme derived from *Archaeglobus fulgidus*, *Methanococcus jannaschii*, and *Pyrococcus furiosus*. The nuclease may be derived from Taq, Tfl and Bca.

Preferably, the cleavage structure formed comprises a pair of interactive signal generating labeled moieties effectively positioned to quench the generation of a detectable signal, the labeled moieties being separated by a site susceptible to FEN nuclease cleavage, thereby allowing the nuclease activity of the FEN nuclease to separate the first interactive signal generating labeled moiety from the second interactive signal generating labeled moiety by cleaving at the site susceptible to FEN nuclease, thereby generating a detectable signal. More preferably, the pair of interactive signal generating moieties comprises a quencher moiety and a fluorescent moiety.

In another embodiment, the method further comprises the step of quantifying the released non-complementary 5' flap.

In another embodiment, the 3' end of the downstream probe is blocked to prevent 3' extension of the downstream probe.

In yet another embodiment, the 3' portion of the downstream probe is further complementary to a third hybridization site of the target nucleic acid, wherein the third hybridization site is 5' to the second hybridization site and the second hybridization site and third hybridization site are separated by an intervening region of the target nucleic acid. Preferably, the 3' portion of the downstream probe hybridizes to the second and third hybridization sites and wherein the intervening region of the target nucleic acid comprises a non-complementary region. Preferably, the 3' portion of the downstream probe is 1-25 nucleotides and the intervening region is 1-20 nucleotides.

In a preferred embodiment, one or both of the blocked 3' ends comprises a base that is non-complementary to the target nucleic acid or a modification that inhibits addition of a nucleotide triphosphate under conditions which permit nucleic acid synthesis or extension. Preferably, one or both of the blocked 3' end comprises:

a) a dideoxynucleotide;

b) a nucleotide wherein the 3' hydroxyl has been replaced with a phosphate group; or c) a nucleotide with a reporter moiety attached to the 3' carbon or to the 3' oxygen.

The invention also provides a method for forming a cleavage structure and cleaving the cleavage structure, wherein the method comprises:
  a) providing:
    a target nucleic acid, which comprises in the 3' to 5' order a first hybridization site and a second hybridization site;
    an upstream oligonucleotide that is complementary to the first hybridization site and wherein the upstream oligonucleotide has a blocked 3' end, and
    a downstream probe comprising a 5' region and a 3' region, wherein the 3' region is complementary to the second hybridization site and the 5' forms a non-complementary 5' flap when the downstream probe is annealed to the target;
  b) annealing the upstream oligonucleotide and the downstream probe to the target nucleic acid to form a cleavage structure; and
  c) cleaving the cleavage structure with a FEN nuclease enzyme derived from *Pyrococcus furiosus* to release the non-complementary 5' flap.

In one embodiment, the non-complementary 5' flap of the downstream probe consists of n nucleotides and the first hybridization site and the second hybridization site are separated by m-nucleotides, wherein n is an integer from 1 to 25 and m is an integer greater than n.

In another embodiment, a cleavage structure is formed comprising at least one labeled moiety capable of providing a signal.

In yet another embodiment, the cleavage structure formed comprises a pair of interactive signal generating labeled moieties effectively positioned to quench the generation of a detectable signal, the labeled moieties being separated by a site susceptible to FEN nuclease cleavage, thereby allowing the nuclease activity of the FEN nuclease to separate the first interactive signal generating labeled moiety from the second interactive signal generating labeled moiety by cleaving at the site susceptible to FEN nuclease, thereby generating a detectable signal. Preferably, the pair of interactive signal generating moieties comprises a quencher moiety and a fluorescent moiety.

In still another embodiment, the method further comprises the step of quantifying the released non-complementary 5' flap.

In another embodiment, the 3' end of the downstream probe is blocked to prevent 3' extension of the downstream probe.

In yet another embodiment, the 3' portion of the downstream probe is further complementary to a third hybridization site of the target nucleic acid, wherein the third hybridization site is 5' to the second hybridization site and the second hybridization site and third hybridization site are separated by an intervening region of the target nucleic acid. Preferably, the 3' portion of the downstream probe hybridizes to the second and third hybridization sites and wherein the intervening region of the target nucleic acid comprises a non-complementary region. Preferably, the 3' portion of the downstream probe is 1-25 nucleotides and the intervening region is 1-20 nucleotides.

In yet another aspect of the invention, one or both of the blocked 3' ends comprises a base that is non-complementary to the target nucleic acid or a modification that inhibits addition of a nucleotide troposphere under conditions which permit nucleic acid synthesis or extension. Preferably, one or both of the blocked 3' end comprises:

a) a dideoxynucleotide;
b) a nucleotide wherein the 3' hydroxyl has been replaced with a phosphate group; or
c) a nucleotide with a reporter moiety attached to the 3' carbon or to the 3' oxygen.

The invention also provides a method for forming a cleavage structure in a sample, cleaving the cleavage structure, and transcribing a nucleic acid complementary to the target nucleic acid, wherein the method comprises:
  a) providing:
    a target nucleic acid, which comprises in the 3' to 5' order a first hybridization site, a second hybridization site and a third hybridization site,
    an upstream extension primer that is complementary to the first hybridization site;
    a clamping oligonucleotide that is complementary to the second hybridization site and wherein the claming oligonucleotide comprises a blocked 3' end and a 5' end with a clamp, wherein the clamp inhibits the displacement of the clamping oligonucleotide by a nucleic acid polymerase, and
    a downstream probe comprising a 5' region and a 3' region, wherein the 3' region is complementary to the third hybridization site and the 5' region forms a non-complementary 5' flap when the downstream probe is hybridized to the target nucleic acid;
  b) annealing the upstream extension primer, the clamping oligonucleotide, and the downstream probe to the target nucleic acid, wherein the clamping oligonucleotide and downstream probe form a cleavage structure;
  c) cleaving the cleavage structure with a nuclease to release the non-complementary 5' flap;
  d) extending a complementary strand from the upstream extension primer to the clamp of the clamping oligonucleotide;
  e) dissociating the clamping oligonucleotide and the downstream probe from the target nucleic acid to allow the nucleic acid polymerase access to the target nucleic acid previously covered by the clamping oligonucleotide and the downstream probe;
  f) further extending the strand complementary to the target nucleic acid; and
  g) detecting the released non-complementary 5' flap, wherein the released non-complementary 5' flap is indicative of the presence of the target nucleic acid in the sample.

In one embodiment, the method further comprises providing an oligonucleotide reverse extension primer that primes a second strand comprising at least a portion of the target nucleic acid.

In another embodiment, the method is performed under conditions which are permissible for PCR.

In yet another embodiment, the method further comprises:
  h) providing an oligonucleotide reverse extension primer that primes a second strand comprising at least a portion of the target nucleic acid;
  i) annealing the reverse extension primer downstream from the sites on the complementary strand corresponding to the first, second, and third hybridization sites;
  j) extending the strand from the reverse extension primer to produce a second strand comprising at least a portion of the target nucleic acid and the first, second, and third hybridization sites;
  k) denaturing the complementary strand from the second strand; and
  l) repeating the denaturation, extension, and cleavage cycles to amplify the target sequence, form the cleavage structure, and cleave the cleavage structure under conditions which are permissive for PCR cycling steps.

In still another embodiment, the 5' flap of the downstream probe consists of n nucleotides and the second hybridization site and the third hybridization site are separated by an m-nucleotides, wherein n is an integer from 1 to 25 and m is an integer greater than n.

In a preferred embodiment, the upstream extension primer anneals to the target sequence under more stringent conditions than the clamping oligonucleotide and the downstream probe. More preferably,
   a) annealing step b) takes place at a temperature below the annealing temperatures of the upstream extension primer, the clamping oligonucleotide, and the downstream probe; and
   b) dissociating step f) takes place at a temperature that is below the annealing temperature of the upstream extension primer and above the annealing temperatures of the clamping oligonucleotide and the downstream probe.

More preferably, the upstream extension primer anneals to the target nucleic acid under more stringent conditions than the clamping oligonucleotide, and the clamping oligonucleotide anneals to the target nucleic acid under more stringent conditions than the downstream labeled probe.

More preferably, a) annealing step b) takes place at a temperature below the annealing temperatures of the upstream extension primer, the clamping oligonucleotide, and the downstream probe; and
   b) dissociating step f) further comprises:
      i) increasing the temperature so that the downstream probe is dissociated from the target nucleic acid while the upstream extension primer and the clamping oligonucleotide remain annealed; and
      ii) further increasing the temperature so that the clamping oligonucleotide is dissociated from the target nucleic acid while the upstream extension primer remains annealed.

In another embodiment, the clamp comprises a sequence or modification that allows the clamping primer to bind the target nucleic acid with sufficiently high affinity so as to prevent its displacement by the nucleic acid polymerase. Preferably, the clamp comprises a GC-rich sequence, a minor groove binder, an intercalating agent, or a LNA.

In another embodiment, the downstream oligonucleotide has a blocked 3' end. Preferably, one or both of the blocked 3' ends comprises a base that is non-complementary to the target nucleic acid or a modification that inhibits addition of a nucleotide triphosphate under conditions which permit nucleic acid synthesis or extension. Preferably, one or both of the blocked 3' end comprises:
   a) a dideoxynucleotide;
   b) a nucleotide wherein the 3' hydroxyl has been replaced with a phosphate group; or
   c) a nucleotide with a reporter moiety attached to the 3' carbon or to the 3' oxygen.

In another embodiment, in dissociating step f), the downstream probe is dissociated from the target nucleic acid prior to dissociating the clamping oligonucleotide from the nucleic acid.

Preferably, the nucleic acid polymerase substantially lacks 5' to 3' exonuclease activity. Preferably, the nucleic acid polymerase is a DNA polymerase. Preferably, the nucleic acid polymerase is thermostable. More preferably, the nucleic acid polymerase is selected from the group consisting of 5' to 3' exonuclease deficient Taq polymerase and Pfu polymerase.

In one embodiment, a cleavage structure is formed comprising at least one labeled moiety capable of providing a signal.

In a preferred embodiment, the nuclease comprising a FEN nuclease. Preferably, the FEN nuclease is a flap-specific nuclease and/or is thermostable. More preferably, it is selected from the group consisting of FEN nuclease enzyme derived from *Archaeglobus fulgidus*, *Methanococcus jannaschii*, and *Pyrococcus furiosus*. The nuclease may be derived from Taq, Tfl and Bca.

In a preferred embodiment, the cleavage structure formed comprises a pair of interactive signal generating labeled moieties effectively positioned to quench the generation of a detectable signal, the labeled moieties being separated by a site susceptible to FEN nuclease cleavage, thereby allowing the nuclease activity of the FEN nuclease to separate the first interactive signal generating labeled moiety from the second interactive signal generating labeled moiety by cleaving at the site susceptible to FEN nuclease, thereby generating a detectable signal. More preferably, the pair of interactive signal generating moieties comprises a quencher moiety and a fluorescent moiety.

In one embodiment, the method further comprises the step of quantifying the released non-complementary 5' flap.

The invention also provides a method for forming a cleavage structure in a sample, cleaving the cleavage, and transcribing a nucleic acid complementary to the target nucleic acid, wherein the method comprises:
   a) providing:
      a target nucleic acid, which comprises in the 3' to 5' order a first hybridization site, a second hybridization site and a third hybridization site,
      an upstream extension primer that is complementary to the first hybridization site;
      a clamping oligonucleotide that is complementary to the second hybridization site and wherein the clamping oligonucleotide comprises a blocked 3' end and a 5' end with a clamp, wherein the clamp inhibits the displacement of the clamping oligonucleotide by a nucleic acid polymerase, and
      a downstream probe comprising a 5' region and a 3' region, wherein the 3' region is complementary to the third hybridization site and the 5' region forms a non-complementary 5' flap when the downstream probe is hybridized to the target nucleic acid;
   b) annealing the upstream extension primer, the clamping oligonucleotide, and the downstream probe to the target nucleic acid, wherein the clamping oligonucleotide and downstream probe form a cleavage structure;
   c) cleaving the cleavage structure with a FEN nuclease enzyme derived from *Pyrococcus furiosus* to release the non-complementary 5' flap;
   d) extending the complementary strand from the upstream extension primer to the clamp of the clamping oligonucleotide;
   e) dissociating the clamping oligonucleotide and the downstream probe from the target nucleic acid to allow the nucleic acid polymerase access to the target nucleic acid previously covered by the clamping oligonucleotide and the downstream probe;
   f) further extending the strand complementary to the target nucleic acid; and
   g) detecting the released non-complementary 5' flap, wherein the released non-complementary 5' flap is indicative of the presence of the target nucleic acid in the sample.

In one embodiment, the method further comprises providing an oligonucleotide reverse extension primer that primes a second strand comprising at least a portion of the target nucleic acid.

In another embodiment, the method is performed under conditions which are permissible for PCR.

In yet another embodiment, the method further comprises:
h) providing an oligonucleotide reverse extension primer that primes a second strand comprising at least a portion of the target nucleic acid;
i) annealing the reverse extension primer downstream from the sites on the complementary strand corresponding to the first, second, and third hybridization sites;
j) extending the strand from the reverse extension primer to produce a second strand comprising at least a portion of the target nucleic acid and the first, second, and third hybridization sites;
k) denaturing the complementary strand from the second strand; and
l) repeating the denaturation, extension, and cleavage cycles to amplify the target sequence, form the cleavage structure, and cleave the cleavage structure under conditions which are permissive for PCR cycling steps.

In still another embodiment, the non-complementary 5' flap of the downstream probe consists of n nucleotides and the first hybridization site and the second hybridization site are separated by m-nucleotides , wherein n is an integer from 1 to 25 and m is an integer greater than n.

In still another embodiment, a cleavage structure is formed comprising at least one labeled moiety capable of providing a signal. Preferably, the cleavage structure formed comprises a pair of interactive signal generating labeled moieties effectively positioned to quench the generation of a detectable signal, the labeled moieties being separated by a site susceptible to FEN nuclease cleavage, thereby allowing the nuclease activity of the FEN nuclease to separate the first interactive signal generating labeled moiety from the second interactive signal generating labeled moiety by cleaving at the site susceptible to FEN nuclease, thereby generating a detectable signal. More preferably, the pair of interactive signal generating moieties comprises a quencher moiety and a fluorescent moiety.

In another embodiment, the method further comprises the step of quantifying the released non-complementary 5' flap.

In still another embodiment, the 3' end of the downstream probe is blocked to prevent 3' extension of the downstream probe. Preferably, one or both of the blocked 3' ends comprises a base that is non-complementary to the target nucleic acid or a modification that inhibits addition of a nucleotide triphosphate under conditions which permit nucleic acid synthesis or extension. Preferably, one or both of the blocked 3' end comprises:
a) a dideoxynucleotide;
b) a nucleotide wherein the 3' hydroxyl has been replaced with a phosphate group; or
c) a nucleotide with a reporter moiety attached to the 3' carbon or to the 3' oxygen.

The present invention also provides a method for forming a cleavage structure in a sample, cleaving the cleavage, and transcribing a nucleic acid complementary to the target nucleic acid, wherein the method comprises:
a) providing:
  a target nucleic acid, which comprises in the 3' to 5' order a first hybridization site, a second hybridization site and a third hybridization site,
  an upstream oligonucleotide extension primer that is complementary to the first hybridization site,
  an upstream oligonucleotide that is complementary to the second hybridization site and wherein the upstream oligonucleotide comprises a blocked 3' end, and
  a downstream probe comprising a 5' region and a 3' region, wherein the 3' region is complementary to the third hybridization site and the 5' region forms a non-complementary 5' flap when the downstream probe is annealed to the target;
b) annealing the upstream oligonucleotide and the downstream probe to the target nucleic acid to form a cleavage structure;
c) cleaving the cleavage structure with a nuclease to release the non-complementary 5' flap;
d) annealing the upstream extension primer to the target nucleic acid;
e) extending the upstream oligonucleotide extension primer to synthesize a strand complementary to the target nucleic acid; and
f) detecting the released non-complementary 5' flap, wherein the released non-complementary 5' flap is indicative of the presence of the target nucleic acid in the sample.

In one embodiment, the method further comprises providing an oligonucleotide reverse extension primer that primes a second strand comprising at least a portion of the target nucleic acid.

In another embodiment, said method is performed under conditions which are permissible for PCR.

In yet another embodiment, the method further comprises:
g) providing an oligonucleotide reverse extension primer that primes a second strand comprising at least a portion of the target nucleic acid;
h) annealing the reverse extension primer downstream from the sites on the complementary strand corresponding to the first, second, and third hybridization sites;
i) extending the strand from the reverse extension primer to produce a second strand comprising at least a portion of the target nucleic acid and the first, second, and third hybridization sites;
j) denaturing the complementary strand from the second strand; and
k) repeating the denaturation, extension, and cleavage cycles to amplify the target sequence, form the cleavage structure, and cleave the cleavage structure under conditions which are permissive for PCR cycling steps.

In another embodiment, the 5' flap of the downstream probe consists of n nucleotides and the second hybridization site and the third hybridization site are separated by m-nucleotides, wherein n is an integer from 1 to 25 and m is greater than n.

In another embodiment, the upstream signal oligonucleotide and the downstream probe anneal to the target sequence under more stringent conditions than the upstream extension primer.

In yet another embodiment, the nuclease comprises a FEN nuclease. More preferably, it is selected from the group consisting of FEN nuclease enzyme derived from *Archaeglobus fulgidus, Methanococcus jannaschii*, and *Pyrococcus furiosus*. The nuclease may be derived from Taq, Tfl and Bca.

The present invention also provides a method for forming a cleavage structure in a sample, cleaving the cleavage structure, and transcribing a nucleic acid complementary to the target nucleic acid, wherein the method comprises:

a) providing:
    a target nucleic acid, which comprises in the 3' to 5' order a first hybridization site, a second hybridization site and a third hybridization site,
    an upstream oligonucleotide extension primer that is complementary to the first hybridization site,
    an upstream oligonucleotide that is complementary to the second hybridization site and wherein the upstream oligonucleotide comprises a blocked 3' end, and
    a downstream probe comprising a 5' region and a 3' region, wherein the 3' region is complementary to the third hybridization site and the 5' region forms a non-complementary 5' flap when the downstream probe is annealed to the target;
b) annealing the upstream oligonucleotide and the downstream probe to the target nucleic acid to form a cleavage structure;
c) cleaving the cleavage structure with a FEN nuclease enzyme derived from *Pyrococcus furiosus* to release the non-complementary 5' flap; and
d) annealing the upstream extension primer to the target nucleic acid;
e) extending the upstream extension primer to synthesize a strand complementary to the target nucleic acid; and
f) detecting the released non-complementary 5' flap, wherein the released non-complementary 5' flap is indicative of the presence of the target nucleic acid in the sample.

In another embodiment, the method further comprises providing an oligonucleotide reverse extension primer that primes a second strand comprising at least a portion of the target nucleic acid.

In yet another embodiment, the method is performed under conditions which are permissible for PCR.

In still another embodiment, the method further comprises:
g) providing an oligonucleotide reverse extension primer that primes a second strand comprising at least a portion of the target nucleic acid;
h) annealing the reverse extension primer downstream from the sites on the complementary strand corresponding to the first, second, and third hybridization sites;
i) extending the strand from the reverse extension primer to produce a second strand comprising at least a portion of the target nucleic acid and the first, second, and third hybridization sites;
j) denaturing the complementary strand from the second strand; and
k) repeating the denaturation, extension, and cleavage cycles to amplify the target sequence, form the cleavage structure, and cleave the cleavage structure under conditions which are permissive for PCR cycling steps.

In yet another embodiment, the non-complementary 5' flap of the downstream probe consists of n nucleotides and the first hybridization site and the second hybridization site are separated by m-nucleotides, wherein n is an integer from 1 to 25 and m is an integer greater than n.

In still another embodiment, a cleavage structure is formed comprising at least one labeled moiety capable of providing a signal. Preferably, the cleavage structure formed comprises a pair of interactive signal generating labeled moieties effectively positioned to quench the generation of a detectable signal, the labeled moieties being separated by a site susceptible to FEN nuclease cleavage, thereby allowing the nuclease activity of the FEN nuclease to separate the first interactive signal generating labeled moiety from the second interactive signal generating labeled moiety by cleaving at the site susceptible to FEN nuclease, thereby generating a detectable signal. More preferably, the pair of interactive signal generating moieties comprises a quencher moiety and a fluorescent moiety.

In another embodiment, the method further comprises the step of quantifying the released non-complementary 5' flap.

In yet another embodiment, the 3' end of the downstream probe is blocked to prevent 3' extension of the downstream probe.

In still another embodiment, one or both of the blocked 3' ends comprises a base that is non-complementary to the target nucleic acid or a modification that inhibits addition of a nucleotide triphosphate under conditions which permit nucleic acid synthesis or extension. Preferably, one or both of the blocked 3' end comprises:
    a) a dideoxynucleotide;
    b) a nucleotide wherein the 3' hydroxyl has been replaced with a phosphate group; or
    c) a nucleotide with a reporter moiety attached to the 3' carbon or to the 3' oxygen.

The present invention also provides a method for forming a cleavage structure in a sample, cleaving the cleavage, transcribing a nucleic acid complementary to the target nucleic acid, and amplifying the target nucleic acid, wherein the method comprises:
a) providing:
    a target nucleic acid, which comprises region A',
    a forward extension primer comprises a non-complementary 5' tag region (X) and a 3' priming region (A), wherein the 5' tag region is not complementary to the target prior to amplification and the 3' priming region (A) is complementary to region (A') in the target nucleic acid,
    an upstream oligonucleotide comprising at least a portion of region X and wherein the upstream oligonucleotide has a blocked 3' end,
    a downstream probe comprising a 5' region and a 3' region, wherein the 3' region comprises at least a portion of region A and the 5' region forms a non-complementary 5' flap when the downstream probe is annealed to the A' portion of the target nucleic acid, and
    a reverse extension primer that primes a second strand comprising at least a portion of the target nucleic acid;
b) annealing region A of the forward extension primer to the target nucleic acid;
c) extending the forward extension primer to produce a complementary strand of the target nucleic acid, wherein the complementary strand includes region A and region X;
d) denaturing the target nucleic acid and the complementary strand;
e) annealing the reverse extension primer to a region of the complementary strand downstream of region A;
f) extending the strand from the reverse extension primer to produce a second strand comprising at least a portion of the target nucleic acid sequence, region A', and a region (X') complementary to the 5' tag;
g) denaturing the complementary strand from the second strand;
h) annealing the upstream oligonucleotide and the downstream probe to the second strand to form a cleavage structure;

i) cleaving the cleavage structure with a nuclease to release the non-complementary 5' flap of the downstream oligonucleotide; and j) detecting the released non-complementary 5' flap, wherein the released non-complementary 5' flap is indicative of the presence of the target nucleic acid in the sample.

In one embodiment, the method further comprises repeating the denaturation, extension, and cleavage cycles to amplify the target sequence, form the cleavage structure, and cleave the cleavage structure under conditions which are permissive for PCR cycling steps.

In one embodiment:
a) X is 5-25 nucleotides;
b) A is 5-25 nucleotides; and
c) the reverse primer is 5-25 nucleotides.

In another embodiment, the nucleic acid polymerase substantially lacks 5' to 3' exonuclease activity.

In yet another embodiment, the 5' flap of the downstream probe consists of n nucleotides and the hybridization sites of the upstream signal oligonucleotide and the downstream probe are separated by an m-nucleotides, wherein n is an integer from 1 to 25 and m is an integer greater than n.

In still another embodiment, the nuclease comprises a FEN nuclease. Preferably the FEN nuclease is selected from the group consisting of FEN nuclease enzyme derived from *Archaeglobus fulgidus, Methanococcus jannaschii*, and *Pyrococcus furiosus*. The nuclease may be derived from Taq, Tfl and Bca.

In yet another embodiment, a cleavage structure is formed comprising at least one labeled moiety capable of providing a signal. Preferably, the cleavage structure formed comprises a pair of interactive signal generating labeled moieties effectively positioned to quench the generation of a detectable signal, the labeled moieties being separated by a site susceptible to FEN nuclease cleavage, thereby allowing the nuclease activity of the FEN nuclease to separate the first interactive signal generating labeled moiety from the second interactive signal generating labeled moiety by cleaving at the site susceptible to FEN nuclease, thereby generating a detectable signal. More preferably, the pair of interactive signal generating moieties comprises a quencher moiety and a fluorescent moiety.

In another embodiment, the method further comprises the step of quantifying the released non-complementary 5' flap.

In yet another embodiment, the 3' end of the downstream probe is blocked to prevent 3' extension of the downstream probe. Preferably, one or both of the blocked 3' ends comprises a base that is non-complementary to the target nucleic acid or a modification that inhibits addition of a nucleotide triphosphate under conditions which permit nucleic acid synthesis or extension. Preferably, one or both of the blocked 3' end comprises:
a) a dideoxynucleotide;
b) a nucleotide wherein the 3' hydroxyl has been replaced with a phosphate group; or
c) a nucleotide with a reporter moiety attached to the 3' carbon or to the 3' oxygen.

The present invention also provides a method for forming a cleavage structure in a sample, cleaving the cleavage structure, transcribing a nucleic acid complementary to the target nucleic acid, and amplifying the target nucleic acid, wherein the method comprises:
a) providing:
   a target nucleic acid, which comprises region A',
   a forward extension primer comprises a non-complementary 5' tag region (X) and a 3' priming region (A), wherein the 5' tag region is not complementary to the target prior to amplification and the 3' priming region (A) is complementary to region (A') in the target nucleic acid,
   an upstream oligonucleotide comprising at least a portion of region X and wherein the upstream oligonucleotide has a blocked 3' end,
   a downstream probe comprising a 5' region and a 3' region, wherein the 3' region comprises at least a portion of region A and the 5' region forms a non-complementary 5' flap when the downstream probe is annealed to the A' portion of the target nucleic acid, and
   a reverse extension primer that primes a second strand comprising at least a portion of the target nucleic acid;
b) annealing region A of the forward extension primer to the target nucleic acid;
c) extending the forward extension primer to produce a complementary strand of the target nucleic acid, wherein the complementary strand includes region A and region X;
d) denaturing the target nucleic acid and the complementary strand;
e) annealing the reverse extension primer to a region of the complementary strand downstream of region A;
f) extending the strand from the reverse extension primer to produce a second strand comprising at least a portion of the target nucleic acid sequence, region A', and a region (X') complementary to the 5' tag;
g) denaturing the complementary strand from the second strand;
h) annealing the upstream oligonucleotide and the downstream probe to the second strand to form a cleavage structure;
i) cleaving the cleavage structure with a FEN nuclease enzyme derived from *Pyrococcus furiosus* to release the non-complementary 5' flap of the downstream oligonucleotide; and
j) detecting the released non-complementary 5' flap, wherein the released non-complementary 5' flap is indicative of the presence of the target nucleic acid in the sample.

In one embodiment, the method further comprises repeating the denaturation, extension, and cleavage cycles to amplify the target sequence, form the cleavage structure, and cleave the cleavage structure under conditions which are permissive for PCR cycling steps.

The present invention also provides a method for forming a cleavage structure in a sample, cleaving the cleavage structure, transcribing a nucleic acid complementary to the target nucleic acid, and amplifying the target nucleic acid, wherein the method comprises:
a) providing:
   a target nucleic acid, which comprises from 3' to 5' an A' region and a T' region, wherein said A' and T' regions are non-contiguous,
   a forward extension primer comprises a 5' tag region comprising two subregions (X1 and X2), wherein X1 is upstream of X2 and a 3' priming region (A), wherein the 5' tag region is not complementary to the target prior to amplification and the 3' priming region (A) is complementary to region A' of the target nucleic acid,
   an upstream oligonucleotide comprising at least a portion of region X1 and wherein the upstream oligonucleotide has a blocked 3' end, a downstream probe comprising a 5' region and a 3' region, wherein the 3' region comprises at least a portion of region X2, and a region T which is downstream of region X2 and is complementary to T' of the target nucleic acid, and wherein the 5' region forms a non-complementary 5' flap when the downstream probe is annealed to the A' region of the target nucleic acid, and a reverse extension primer that primes a second strand comprising at least a portion of the target nucleic acid;

b) annealing complementary region A of the forward extension primer to the A' region and T' region of the target nucleic acid;

c) extending the forward extension primer to produce a complementary strand of the target nucleic acid, wherein the complementary strand includes region A and regions X1 and X2;

d) denaturing the target nucleic acid and the complementary strand;

e) annealing the reverse extension primer to a region of the complementary strand downstream of region T;

f) extending the strand from the reverse extension primer to produce a second strand comprising at least a portion of the target nucleic acid sequence, region A', region T' and a region (X1', X2') complementary to the 5' tag;

g) denaturing the complementary strand from the second strand;

h) annealing the upstream oligonucleotide and the downstream probe to the second strand to form a cleavage structure i) cleaving the cleavage structure with a nuclease to release the non-complementary 5' flap of the downstream oligonucleotide; and j) detecting the released non-complementary 5' flap, wherein the released non-complementary 5' flap is indicative of the presence of the target nucleic acid in the sample.

In one embodiment, the method further comprises repeating the denaturation, extension, and cleavage cycles to amplify the target sequence, form the cleavage structure, and cleave the cleavage structure under conditions which are permissive for PCR cycling steps.

In another embodiment:
a) X1 is 5-25 nucleotides;
b) X2 is and T are each independently 1-25 nucleotides, and X2 and T together are 5-30 nucleotides;
c) A is 5-25 nucleotides; and
d) the reverse primer is 5-25 nucleotides.

In yet another embodiment, the nucleic acid polymerase substantially lacks 5' to 3' exonuclease activity.

In still another embodiment,
a. the 5' flap of the downstream probe consists of n nucleotides and the hybridization sites of the upstream signal oligonucleotide and the downstream probe are separated by an m-nucleotides, wherein n is an integer from 1 to 25 and m is an integer greater than n.

In still another embodiment, the nuclease comprises a FEN nuclease. Preferably the FEN nuclease is selected from the group consisting of FEN nuclease enzyme derived from *Archaeglobus fulgidus, Methanococcus jannaschii,* and *Pyrococcus furiosus.* The nuclease may be derived from Taq, Tfl and Bca.

In another embodiment, a cleavage structure is formed comprising at least one labeled moiety capable of providing a signal. Preferably, the cleavage structure formed comprises a pair of interactive signal generating labeled moieties effectively positioned to quench the generation of a detectable signal, the labeled moieties being separated by a site susceptible to FEN nuclease cleavage, thereby allowing the nuclease activity of the FEN nuclease to separate the first interactive signal generating labeled moiety from the second interactive signal generating labeled moiety by cleaving at the site susceptible to FEN nuclease, thereby generating a detectable signal. More preferably, the pair of interactive signal generating moieties comprises a quencher moiety and a fluorescent moiety.

In another embodiment, the method further comprises the step of quantifying the released non-complementary 5' flap.

In yet another embodiment, the 3' end of the downstream probe is blocked to prevent 3' extension of the downstream probe. Preferably, one or both of the blocked 3' ends comprises a base that is non-complementary to the target nucleic acid or a modification that inhibits addition of a nucleotide triphosphate under conditions which permit nucleic acid synthesis or extension. Preferably, one or both of the blocked 3' end comprises:

a) a dideoxynucleotide;
b) a nucleotide wherein the 3' hydroxyl has been replaced with a phosphate group; or
c) a nucleotide with a reporter moiety attached to the 3' carbon or to the 3' oxygen.

The present invention provides a method for forming a cleavage structure in a sample, cleaving the cleavage structure, transcribing a nucleic acid complementary to the target nucleic acid, and amplifying the target nucleic acid, wherein the method comprises:

a) providing:
a target nucleic acid, which comprises from 3' to 5' a A' region and a T' region, wherein said A' and T' regions are non-contiguous, a forward extension primer comprises a 5' tag region comprising two subregions (X1 and X2), wherein X1 is upstream of X2 and a 3' priming region (A), wherein the 5' tag region is not complementary to the target prior to amplification and the 3' priming region (A) is complementary to region (A') of the target nucleic acid, an upstream oligonucleotide comprising at least a portion of region X1 and wherein the upstream oligonucleotide has a blocked 3' end, a downstream probe comprising a 5' region and a 3' region, wherein the 3' region comprises at least a portion of region X2, and a region T which is downstream of region X2 and is complementary to T' of the target nucleic acid, and wherein the 5' region forms a non-complementary 5' flap when the downstream probe is annealed to the A' region of the target nucleic acid, and a reverse extension primer that primes a second strand comprising at least a portion of the target nucleic acid;

b) annealing complementary region A of the forward extension primer to the A' region and T' region of the target nucleic acid;

c) extending the forward extension primer to produce a complementary strand of the target nucleic acid, wherein the complementary strand includes region A and regions X1 and X2;

d) denaturing the target nucleic acid and the complementary strand;

e) annealing the reverse extension primer to a region of the complementary strand downstream of region T;

f) extending the strand from the reverse extension primer to produce a second strand comprising at least a portion of the target nucleic acid sequence, region A', region T' and a region (X1', X2') complementary to the 5' tag;

g) denaturing the complementary strand from the second strand;

h) annealing the upstream oligonucleotide and the downstream probe to the second strand to form a cleavage structure i) cleaving the cleavage structure with a FEN nuclease derived from *Pyrococcus furiosus* to release the non-complementary 5' flap of the downstream oligonucleotide; and j) detecting the released non-complementary 5' flap, wherein the released non-complementary 5' flap is indicative of the presence of the target nucleic acid in the sample.

In one embodiment, the method further comprises repeating the denaturation, extension, and cleavage cycles to amplify the target sequence, form the cleavage structure, and cleave the cleavage structure under conditions which are permissive for PCR cycling steps.

In another embodiment, the non-complementary 5' flap of the downstream probe consists of n nucleotides and the first hybridization site and the second hybridization site are separated by m-nucleotides, wherein n is an integer from 1 to 25 and m is an integer greater than n.

In yet another embodiment, a cleavage structure is formed comprising at least one labeled moiety capable of providing a signal. Preferably, the cleavage structure formed comprises a pair of interactive signal generating labeled moieties effectively positioned to quench the generation of a detectable signal, the labeled moieties being separated by a site susceptible to FEN nuclease cleavage, thereby allowing the nuclease activity of the FEN nuclease to separate the first interactive signal generating labeled moiety from the second interactive signal generating labeled moiety by cleaving at the site susceptible to FEN nuclease, thereby generating a detectable signal. More preferably, the pair of interactive signal generating moieties comprises a quencher moiety and a fluorescent moiety.

In another embodiment, the method further comprises the step of quantifying the released non-complementary 5' flap.

In yet another embodiment, the 3' end of the downstream probe is blocked to prevent 3' extension of the downstream probe. Preferably, one or both of the blocked 3' ends comprises a base that is non-complementary to the target nucleic acid or a modification that inhibits addition of a nucleotide triphosphate under conditions which permit nucleic acid synthesis or extension. Preferably, one or both of the blocked 3' end comprises:

a) a dideoxynucleotide;

b) a nucleotide wherein the 3' hydroxyl has been replaced with a phosphate group; or c) a nucleotide with a reporter moiety attached to the 3' carbon or to the 3' oxygen.

I. Nucleases

Nucleases useful according to the invention include any enzyme that possesses 5' endonucleolytic activity for example a DNA polymerase, e.g. DNA polymerase I from *E. coli*, and DNA polymerase from *Thermus aquaticus* (Taq), *Thermus thermophilus* (Tth), and *Thermus flavus* (Tfl). Nucleases useful according to the invention also include DNA polymerases with 5'-3' exonuclease activity, including but not limited to eubacterial DNA polymerase I, including enzymes derived from Thermus species (Taq, Tfl, Tth, Tca (caldophilus), Tbr (brockianus)), enzymes derived from Bacillus species (Bst, Bca, Magenta (full length polymerases, NOT N-truncated versions)), enzymes derived from Thermotoga species (Tma (maritima, Tne (neopolitana)) and *E. coli* DNA polymerase I. The term nuclease also embodies FEN nucleases. A nuclease useful according to the invention cannot cleave either a probe or primer that is not hybridized to a target nucleic acid or a target nucleic acid that is not hybridized to a probe or a primer.

FEN-1 is an ~40 kDa divalent metal ion-dependent exo- and endonuclease that specifically recognizes the backbone of a 5' single-stranded flap strand and tracks down this arm to the cleavage site, which is located at the junction wherein the two strands of duplex DNA adjoin the single-stranded arm. Both the endo- and exonucleolytic activities show little sensitivity to the base at the most 5' position at the flap or nick. Both FEN-1 endo- and exonucleolytic substrate binding and cutting are stimulated by an upstream oligonucleotide (flap adjacent strand or primer). This is also the case for *E. coli* pol I. The endonuclease activity of the enzyme is independent of the 5' flap length, cleaving a 5' flap as small as one nucleotide. The endonuclease and exonuclease activities are insensitive to the chemical nature of the substrate, cleaving both DNA and RNA.

Both the endo- and exonucleolytic activities are inhibited by concentrations of salts in the physiological range. The exonuclease activity is inhibited 50-fold at 50 mM NaCl as compared to 0 mM NaCl. The endonuclease activity is inhibited only sevenfold at 50 mM NaCl (Reviewed in Lieber 1997, supra).

Although a 5'-OH terminus is a good substrate for FEN-1 loading onto a 5' flap substrate, it serves as a very poor substrate when part of a nick in an otherwise double stranded DNA structure. The electrostatic repulsion by the terminal phosphate is likely to favor breathing of the substrate into a pseudo-flap configuration, providing the active form of the substrate for FEN-1. Such an explanation would indicate a single active site and a single mechanism of loading of FEN-1 onto the 5' ssDNA terminus of the flap or pseudo-flap configuration of the nick. Consistent with this model are observations that optimal activity at a nick requires very low $Mg^{+2}$ and monovalent salt concentrations, which destabilize base-pairing and would favor breathing of a nick to a flap. Higher $Mg^{+2}$ and monovalent salt concentrations would disfavor breathing and inhibit cutting of nicked or gapped structures that do require breathing to convert to a flap. Cleavage of stable flap structures is optimal at moderate $Mg^{+2}$ levels and does not decrease with increasing $Mg^{30\ 2}$ concentration. This is because a flap substrate does not have to melt out base pairs to achieve its structure; hence, it is entirely insensitive to $Mg^{+2}$. Though the endonucleolytic activity decreases with monovalent salt, the decline is not nearly as sharp as that seen for the exonucleolytic activity. Furthermore, it has previously been shown that one-nucleotide flaps are efficient substrates. All of these observations are consistent with the fact that when FEN-1 has been interpreted to be functioning as an exonuclease, the size of the degradation products vary from one to several nucleotides in length. Breathing of nicks into flaps of varying length would be expected to vary with local sequence, depending on the G/C content. In summary, a nick breathing to form a transient flap means that the exonucleolytic activity of FEN-1 is the same as the endonucleolytic activity (Reviewed in Lieber, 1997, supra).

The endonuclease and exonuclease activities of FEN-1 cleave both DNA and RNA without requiring accessory proteins. At the replication fork, however, FEN-1 does interact with other proteins, including a DNA helicase and the proliferating cell nuclear antigen (PCNA), the processivity factor for DNA polymerases ♭and ¶. PCNA significantly stimulates FEN-1 endo- and exonucleolytic activity.

The FEN-1 enzymes are functionally related to several smaller bacteriophage 5'3' exonucleases such as T5 5' exonuclease and T4 RNase H as well as to the larger eukaryotic nucleotide excision repair enzymes such as XPG, which also acts in the transcription-coupled repair of oxidative base damage. In eubacteria such as *Escherichia coli* and *Thermus aquaticus*, Okazaki processing is provided by the PolI 5' 3' exonuclease domain. These bacterial and phage enzymes share two areas of limited sequence homology with FEN-1, which are termed the N (N-terminal) and I (intermediate) regions, with the residue similarities concentrated around seven conserved acidic residues. Based on crystal structures of T4 RNase H and T5 exonuclease as well as mutagenesis data, it has been proposed that these residues bind to two $Mg^{+2}$ ions that are required for affecting DNA hydrolysis; however, the role each metal plays in the catalytic cycle, which is subtly different for each enzyme, is not well understood (Reviewed in Hosfield et al., 1998b, supra).

fen-1 genes encoding FEN-1 enzymes useful in the invention include murine fen-1, human fen-1, rat fen-1, Xenopus laevis fen-1, and fen-1 genes derived from four archaebacteria *Archaeglobus fulgidus, Methanococcus jannaschii, Pyrococcus furiosus* and *Pyrococcus horikoshii*. cDNA clones encoding FEN-1 enzymes have been isolated from human (GenBank Accession Nos.: NM 004111 and L37374), mouse (GenBank Accession No.: L26320), rat (GenBank Accession No.: AA819793), *Xenopus laevis* (GenBank Accession Nos.: U68141 and U64563), and *P. furiosus* (GenBank Accession No.: AF013497). The complete nucleotide sequence for *P. horikoshii* flap endonuclease has also been determined (GenBank Accession No.: AB005215). The FEN-1 family also includes the *Saccharomyces cerevisiae* RAD27 gene (GenBank Accession No.: Z28113 Y13137) and the *Saccharomyces pombe* RAD2 gene (GenBank Accession No.: X77041). The archaeal genome of *Methanobacterium thermautotrophiculum* has also been sequenced. Although the sequence similarity between FEN-1 and prokaryotic and viral 5'3' exonucleases is low, FEN-1s within the eukaryotic kingdom are highly conserved at the amino acid level, with the human and *S. cerevisiae* proteins being 60% identical and 78% similar. The three archaebacterial FEN-1 proteins are also, highly homologous to the eukaryotic FEN-1 enzymes (Reviewed in Matsui et al., 1999., *J. Biol. Chem.*, 274:18297, Hosfield et al., 1998b, *J. Biol. Chem.*, 273:27154 and Lieber, 1997, *BioEssays*, 19:233).

The sequence similarities in the two conserved nuclease domains (N-terminal or N and intermediate or I domains) between human and other FEN-1 family members are 92% (murine), 79% (*S. cerevisiae*), 77% (*S. pombe*), 72% (*A. fulgidus*), 76% (*M. jannaschii*), and 74% (*P. furiosus*).

FEN-1 specifically recognizes the backbone of a 5' single-stranded flap strand and migrates down this flap arm to the cleavage site located at the junction between the two strands of duplex DNA and the single-stranded arm. If the strand upstream of the flap (sometimes called the flap adjacent strand or primer strand) is removed, the resulting structure is termed a pseudo-Y (see FIG. 1). This structure is cleaved by FEN-1, but at 20- to 100-fold lower efficiency. FEN-1 does not cleave 3' single-stranded flaps. However, FEN-1 acting as an exonuclease will hydrolyze dsDNA substrates containing a gap or nick (Reviewed in Hosfield et al., 1998a, supra, Hosfield et al., 1999b, supra and Lieber 1997, supra).

Exonucleolytically, FEN-1 acts at a nick and, with lower efficiency, at a gap or a recessed 5' end on dsDNA. At gapped structures, the efficiency of FEN-1 binding and cutting decreases with increasing gap size up to approximately five nucleotides and then stabilizes at a level of cleavage that is equivalent to activity on a recessed 5' end within dsDNA. Blunt dsDNA, recessed 3' ends and ssDNA are not cleaved (Reviewed in Lieber 1997, supra).

FEN nucleases that are useful according to the invention have been isolated from a variety of organisms including human (GenBank Accession Nos.: NM 004111 and L37374), mouse (GenBank Accession No.: L26320), rat (GenBank Accession No.: AA819793), yeast (GenBank Accession No.: Z28113 Y13137 and GenBank Accession No.: X77041) and *Xenopus laevis* (GenBank Accession Nos.: U68141 and U64563). Such enzymes can be cloned and overexpressed using conventional techniques well known in the art.

A FEN nuclease according to the invention is preferably thermostable. Thermostable FEN nucleases have been isolated and characterized from a variety of thermostable organisms including four archaebacteria. The cDNA sequence (GenBank Accession No.: AF013497) and the amino acid sequence (Hosfield et al., 1998a, supra and Hosfield et al., 1998b) for *P. furiosus* flap endonuclease have been determined. The complete nucleotide sequence (GenBank Accession No.: AB005215) and the amino acid sequence (Matsui et al., supra) for *P. horikoshii* flap endonuclease have also been determined. The amino acid sequence for *M. jannaschii* (Hosfield et al., 1998b and Matsui et al., 1999 supra) and *A. fulgidus* (Hosfield et al., 1998b) flap endonuclease have also been determined.

Thermostable FEN-1 enzymes can be cloned and overexpressed using techniques well known in the art and described in Hosfield et al., 1998a, supra, Hosfield et al., 1998b, Kaiser et al., 1999, J. Biol. Chem., 274: 21387 and Matusi et al., supra and herein in Example 2 entitled "Cloning Pfu FEN-1".

The endonuclease activity of a FEN enzyme can be measured by a variety of methods including the following.

A. Fen Endonuclease Activity Assay

Figure 2:
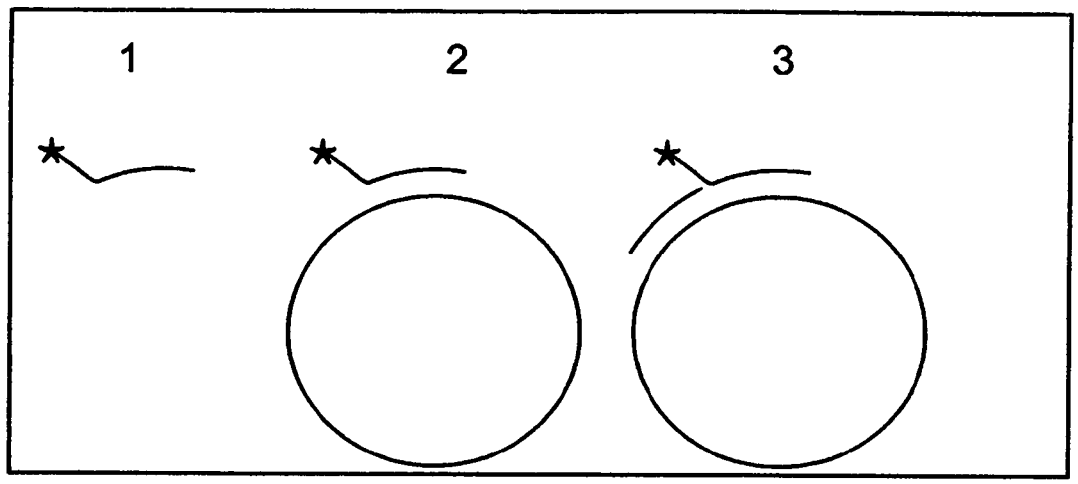
FIG. 2 demonstrates three templates (labeled 1, 2, and 3) that may be used to detect FEN nuclease activity.

1. Templates (for example as shown in FIG. 2) are used to evaluate the activity of a FEN nuclease according to the invention.

Template 1 is a 5' $^{33}$P labeled oligonucleotide (Heltest4) with the following sequence: 5'AAAATAAATAAAAAAAAT ACTGTTGGGAAGGGCGATCGGTGCG 3' (SEQ ID NO: 1). The underlined section of Heltest4 represents the region complementary to M13mp18+. The cleavage product is an 18 nucleotide fragment with the sequence AAAATAAATAAAAAAAAT (SEQ ID NO: 2).

Heltest4 binds to M13 to produce a complementary double stranded domain as well as a non-complementary 5' overhang. This duplex forms template 2 (FIG. 2) which is also used for helicase assays. Template 3 (FIG. 2) has an additional primer (FENAS) bound to M13 and is directly adjacent to Heltest4. The sequence of FENAS is:

5' CCATTCGCCATTCAGGCTGCGCA 3' (SEQ ID NO: 3).

In the presence of template 3, FEN binds the free 5' terminus of Heltest4, migrates to the junction and cleaves Heltest4 to produce an 18 nucleotide fragment. Templates 1 and 2 serve as controls, although template 2 can also serve as a template.

Templates are prepared as described below:

|          | Template 1 | Template 2 | Template 3 |
|----------|------------|------------|------------|
| Heltest4 | 14 μl      | 14 μl      | 14 μl      |
| M13      | **         | 14 μl      | 14 μl      |
| FENAS    | **         | **         | 14 μl      |
| H₂O      | 28 μl      | 14 μl      | **         |
| 10x Pfu Buff. | 4.6 μl | 4.6 μl    | 4.6 μl     |

10× Pfu buffer is available from Stratagene (Catalog # 200536). According to the method of the invention, 10× Pfu buffer is diluted such that a reaction is carried out in the presence of 1× buffer.

M13 is M13mp18+strand and is at a concentration of 200 ng/μL, $^{33}$P labeled Heltest4 is at an approximate concentration of 0.7 ng/μl, and FENAS is at a concentration of 4.3 ng/μl. Based on these concentrations, the Heltest4 and M13 are at approximately equal molar amounts ($5 \times 10^{-14}$) and FENAS is present in an approximately 10× molar excess ($6 \times 10^{-13}$).

The template mixture is heated at 95° C. for five minutes, cooled to room temperature for 45 minutes and stored at 4° C. overnight.

2 μl of FEN-1 or, as a control, H₂O are mixed with the three templates as follows:

| 3 μl    | template            |
|---------|---------------------|
| 0.7 μl  | 10x cloned Pfu buffer |
| 0.56 μl | 100 mM MgCl₂        |
| 2.00 μl | enzyme or H₂O       |
| 0.74 μl | H₂0                 |
| 7.00 μl | total volume        |

The reactions are allowed to proceed for 30 minutes at 50° C. and stopped by the addition of 2 μl formamide "Sequencing Stop" solution to each sample. Samples are heated at 95° C. for five minutes and loaded on a 6% acrylamide, 7M urea CastAway (Stratagene) gel.

Alternatively, FEN activity can be analyzed in the following buffer wherein a one hour incubation time is utilized.

10× FEN Buffer
500 mM Tris-HCl pH 8.0
100 mM MgCl₂

The reaction mixture below is mixed with 2 μl of FEN or, as a control, 2 μl of H₂O.

| 3 μl    | template       |
|---------|----------------|
| 0.7 μl  | 10x FEN buffer |
| 2.00 μl | enzyme or H₂O  |
| 1.3 μl  | H₂O            |
| 7.00 μl | total volume   |

Samples are incubated for one hour at 50° C. in a Robocyler 96 hot top thermal cycler. Following the addition of 2 μl of Sequencing Stop dye solution, samples are heated at 99° C. for five minutes. Samples are loaded on an eleven-inch long, hand-poured, 20% acrylamide/bis acrylamide, 7M urea gel. The gel is run at 20 watts until the bromophenol blue has migrated approximately ⅔ the total distance. The gel is removed from the glass plates and soaked for 10 minutes in fix (15% methanol, 5% acetic acid) and then for 10 minutes in water. The gel is placed on Whatmann 3 mm paper, covered with plastic wrap and dried for 2 hours in a heated vacuum gel dryer. The gel is exposed overnight to X-ray film.

2. FEN endonuclease activity can also be measured according to the method of Kaiser et al., supra). Briefly, reactions are carried out in a 1011 volume containing 10 mM MOPS, pH 7.5, 0.05% Tween 20, 0.05% Nonidet P-40, 10 lg/ml tRNA, and 200 mM KCl for TaqPol and TthPol or 50 mM KCl for all other enzymes. Reaction conditions can be varied depending on the cleavage structure being analyzed. Substrates (21M) and varying amounts of enzyme are mixed with the indicated (above) reaction buffer and overlaid with Chill-out (MJ Research) liquid wax. Substrates are heat denatured at 90° C. for 20 s and cooled to 50° C., then reactions are started by addition of MgCl₂ or MnCl₂ and incubated at 50° C. for the specified length of time. Reactions are stopped by the addition of 1011 of 95% formamide containing 10 mM EDTA and 0.02% methyl violet (Sigma). Samples are heated to 90° C. for 1 min immediately before electrophoresis on a 20% denaturing acrylamide gel (19:1 cross-linked), with 7M urea, and in a buffer of 45 mM Tris borate, pH 8.3, 1.4 mM EDTA. Unless otherwise indicated, 1⊠1 of each stopped reaction is loaded per lane. Gels are scanned on an FMBIO-100 fluorescent gel scanner (Hitachi) using a 505-nm filter. The fraction of cleaved product is determined from intensities of bands corresponding to uncut and cut substrate with FMBIO Analysis software (version 6.0, Hitachi). The fraction of cut product should not exceed 20% to ensure that measurements approximate initial cleavage rates. The cleavage rate is defined as the concentration of cut product divided by the enzyme concentration and the time of the reaction (in minutes). For each enzyme three data points are used to determine the rate and experimental error.

3. FEN endonuclease activity can also be measured according to the method of Hosfield et al., 1998a, supra. Briefly, in a final volume of 13 μl, varying amounts of FEN and 1.54 pmol of labeled cleavage substrate are incubated at different temperatures for 30 min before the reaction is quenched with an equal volume of stop solution (10 mM EDTA, 95% deionized formamide, and 0.008% bromophenol blue and xylene cyanol). Samples are electrophoresed through denaturing 15% polyacrylamide gels, and the relative amounts of starting material and product are quantitated using the IPLabGel system (Stratagene) running MacBAS image analysis software. Most reactions are performed in standard assay buffer (10 mM Tris-HCl (pH 8.0), 10 mM MgCl₂, and 50 μg/ml bovine serum albumin); however, in a series of experiments the effect of different divalent metals and pH levels are studied by varying the standard buffer. For divalent metals, MgCl₂ is omitted, and different metal ions are used at a final concentration of 10 mM. To study the influence of pH, buffers containing different amounts of Tris-HCl, glycine, and sodium acetate are used at a final concentration of 10 mM to obtain a wide range of pH levels at 25° C.

4. FEN endonuclease activity can also be measured according to the method of Matusi et al., 1999, supra. Briefly, the enzyme are performed in a 15-μl reaction mixture containing 50 mM Tris-HCl (pH 7.4), 1.5 mM MgCl₂, 0.5 mM β-mercaptoethanol, 100 lg/ml bovine serum albumin, and 0.6 pmol of a labeled cleavage structure. After incubation for 30 min at 600 C, the reaction is terminated by adding 15 μl of 95% formamide containing 10 mM EDTA and 1 mg/ml bromophenol blue. The samples are heated at 95° C. for 10 min, loaded onto a 15% polyacrylamide gel (35 cm×42.5 cm) containing 7M urea and 10× TBE (89 mM Tris-HCl, 89 mM boric acid, 2 mM EDTA (pH 8.0)), and then electrophoresed for 2 h at 2000 V. Reaction products are visualized and quantified using a PhosphorImager (Bio-Rad). Size marker, oligonucleotides are 5' end-labeled with [α-$^{32}$P]ATP and T4 polynucleotide kinase.

To determine the optimum pH, the reaction is performed in an assay mixture (15 μl) containing 1.5 mM $MgCl_2$, 0.5 mM β-mercaptoethanol, 100 μg/ml bovine serum albumin, and 0.6 pmol of 5' end-labeled cleavage structure in 50 mM of one of the following buffers at 600 C for 30 min. Three different 50 mM buffers are used to obtain a wide pH range as follows: sodium acetate buffer (pH 4.0-5.5), phosphate buffer (pH 5.5-8.0), and borate buffer (pH 8.0-9.4).

B. Fen Exonuclease Activity Assay

The exonuclease activity of a FEN nuclease according to the invention can be measured by the method of measuring FEN-1 endonuclease activity described in Matsui et al., 1999, supra and summarized above.

Alternatively, the exonuclease activity of a FEN enzyme can be analyzed by the method described in Hosfield et al., 1998b, supra. Briefly, exonuclease activities are assayed using a nicked substrate of FEN under conditions identical to those described for the endonuclease assays (described above).

The precise positions of DNA cleavage in both the exonuclease and endonuclease experiments can be obtained by partial digestion of a 5' $^{32}$P-labeled template strand using the 3'-5' exonuclease activity of Klenow fragment.

Figure 3:
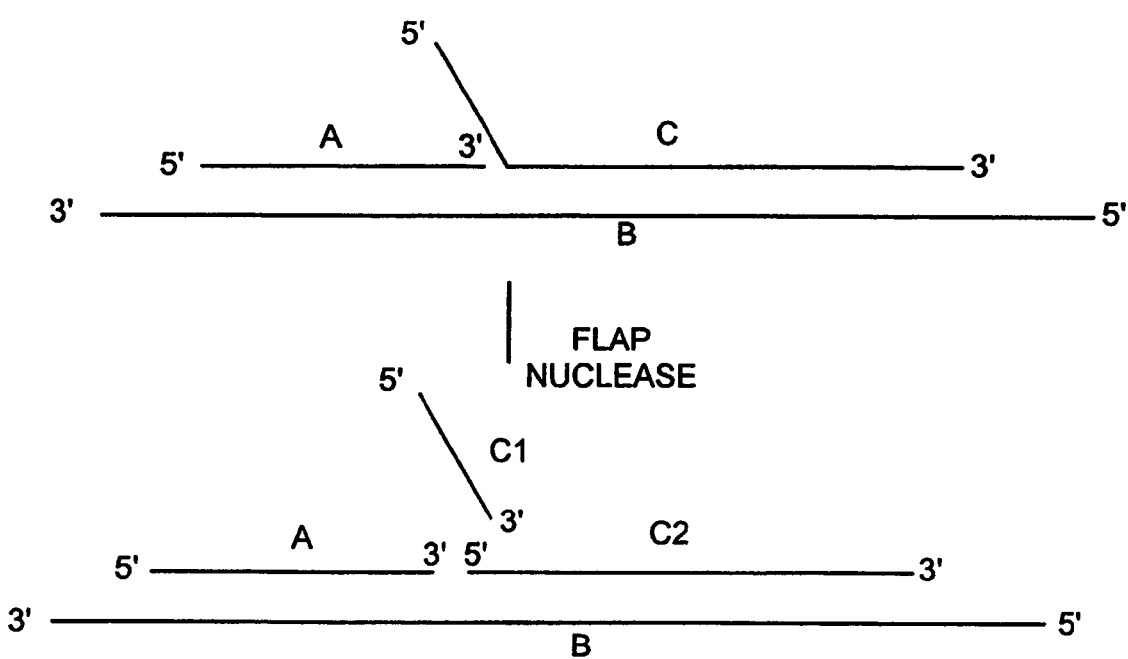
FIG. 3 is a diagram illustrating a synthesis and cleavage reaction to generate a signal according to the invention.

A cleavage structure according to the invention comprises a partially displaced 5' end of an oligonucleotide annealed to a target nucleic acid sequence. Another cleavage structure according to the invention comprises a target nucleic acid sequence (for example B in FIG. 3), an upstream oligonucleotide that is complementary to the target sequence (for example A in FIG. 3), and a downstream oligonucleotide that is complementary to the target sequence (for example C in FIG. 3). A cleavage structure according to the invention can be formed by overlap between the upstream oligonucleotide and the downstream probe, or by extension of the upstream oligonucleotide by the synthetic activity of a nucleic acid polymerase, and subsequent partial displacement of the 5' end of the downstream oligonucleotide. A cleavage structure of this type is formed according to the method described in the section entitled "Cleavage Structure".

Alternatively, a cleavage structure according to the invention is formed by annealing a target nucleic acid sequence to an oligonucleotide wherein the oligonucleotide comprises a complementary region that anneals to the target nucleic acid sequence, and a non-complementary region that does not anneal to the target nucleic acid sequence and forms a 5' flap. According to this embodiment, a cleavage structure comprises a 5' flap formed by a non-complementary region of the oligonucleotide.

A cleavage structure according to the invention also comprises an overlapping flap wherein the 3' end of an upstream oligonucleotide capable of annealing to a target nucleic acid sequence (for example A in FIG. 3) is complementary to 1 (or more) base pair of the downstream oligonucleotide (for example C in FIG. 3) that is annealed to a target nucleic acid sequence and wherein the 1 (or more) base pair overlap is directly downstream of the point of extension of the single stranded flap and is formed according to method described in the section entitled "Cleavage Structure".

II. Nucleic Acid Polymerases

The invention provides for nucleic acid polymerases. Preferably, the nucleic acid polymerase according to the invention is thermostable.

Known DNA polymerases include, for example, *E. coli* DNA polymerase I, *Thermus thermophilus* (Tth) DNA polymerase, *Bacillus stearothermophilus* DNA polymerase, *Thermococcus litoralis* DNA polymerase, *Thermus aquaticus* (Taq) DNA polymerase and *Pyrococcus furiosus* (Pfu) DNA polymerase.

Nucleic acid polymerases substantially lacking 5' to 3' exonuclease activity useful according to the invention include but are not limited to Klenow and Klenow exo-, and T7 DNA polymerase (Sequenase).

Thermostable nucleic acid polymerases substantially lacking 5' to 3' exonuclease activity useful according to the invention include but are not limited to Pfu, exo-Pfu (a mutant form of Pfu that lacks 3' to 5' exonuclease activity), the Stoffel fragment of Taq, N-truncated Bst, N-truncated Bca, Genta, JdF3 exo-, Vent, Vent exo- (a mutant form of Vent that lacks 3' to 5' exonuclease activity), Deep Vent, Deep Vent exo- (a mutant form of Deep Vent that lacks 3' to 5' exonuclease activity), U1Tma, and ThermoSequenase.

Nucleic acid polymerases useful according to the invention include both native polymerases as well as polymerase mutants, which lack 5' to 3' exonuclease activity. Nucleic acid polymerases useful according to the invention can possess different degrees of thermostability. Preferably, a nucleic acid polymerase according to the invention exhibits strand displacement activity at the temperature at which it can extend a nucleic acid primer. In a preferred embodiment of the invention, a nucleic acid polymerase lacks both 5' to 3' and 3' to 5' exonuclease activity.

Additional nucleic acid polymerases substantially lacking 5' to 3' exonuclease activity with different degrees of thermostability useful according to the invention are listed below.

A. Bacteriophage DNA Polymerases (Useful for 37° C. Assays):

Bacteriophage DNA polymerases are devoid of 5' to 3' exonuclease activity, as this activity is encoded by a separate polypeptide. Examples of suitable DNA polymerases are T4, T7, and φ29 DNA polymerase. The enzymes available commercially are: T4 (available from many sources e.g., Epicentre) and T7 (available from many sources, e.g. Epicentre for unmodified and USB for 3' to 5' exo⁻T7 "Sequenase" DNA polymerase).

B. Archaeal DNA Polymerases:

There are 2 different classes of DNA polymerases which have been identified in archaea: 1. Family B/pol α type (homologs of Pfu from *Pyrococcus furiosus*) and 2. pol II type (homologs of *P. furiosus* DP1/DP2 2-subunit polymerase). DNA polymerases from both classes have been shown to naturally lack an associated 5' to 3' exonuclease activity and to possess 3' to 5' exonuclease (proofreading) activity. Suitable DNA polymerases (pol α or pol II) can be derived from archaea with optimal growth temperatures that are similar to the desired assay temperatures. Examples of suitable archaea include, but are not limited to:

1. Thermolabile (useful for 37° C. assays)-e.g., *Methanococcus voltae*
2. Thermostable (useful for non-PCR assays)-e.g., *Sulfolobus solfataricus, Sulfolobus acidocaldarium, Methanococcus jannaschi, Thermoplasma acidophilum*. It is estimated that suitable archaea exhibit maximal growth temperatures of $\leq 80\text{-}85°$ C. or optimal growth temperatures of $\leq 70\text{-}80°$ C.
3. Thermostable (useful for PCR assays)-e.g., *Pyrococcus* species (*furiosus*, species GB-D, species strain KOD1, *woesii, abysii, horikoshii*), *Thermococcus* species (*litoralis*, species 90 North-7, species JDF-3, *gorgonarius*), *Pyrodictium occultum*, and *Archaeoglobus fulgidus*. It is estimated that suitable archaea would exhibit maximal growth temperatures of $\geq 80\text{-}85°$ C. or optimal growth temperatures of $\geq 70\text{-}80°$ C. Appropriate PCR enzymes from the archaeal pol $\alpha$ DNA polymerase group are commercially available, including KOD (Toyobo), Pfx (Life Technologies, Inc.), Vent (New England BioLabs), Deep Vent (New England BioLabs), and Pwo (Boehringer-Mannheim).

Additional archaea related to those listed above are described in the following references: *Archaea: A Laboratory Manual* (Robb, F. T. and Place, A. R., eds.), Cold Spring Harbor Laboratory Press, Cold Spring Harbor, N.Y., 1995 and *Thermophilic Bacteria* (Kristjansson, J. K.,ed.) CRC Press, Inc., Boca Raton, Fla., 1992.

C. Eubacterial DNA Polymerases:

There are 3 classes of eubacterial DNA polymerases, pol I, II, and III. Enzymes in the Pol I DNA polymerase family possess 5' to 3' exonuclease activity, and certain members also exhibit 3' to 5' exonuclease activity. Pol II DNA polymerases naturally lack 5' to 3' exonuclease activity, but do exhibit 3' to 5' exonuclease activity. Pol III DNA polymerases represent the major replicative DNA polymerase of the cell and are composed of multiple subunits. The pol III catalytic subunit lacks 5' to 3' exonuclease activity, but in some cases 3' to 5' exonuclease activity is located in the same polypeptide.

There are a variety of commercially available Pol I DNA polymerases, some of which have been modified to reduce or abolish 5' to 3' exonuclease activity. Methods used to eliminate 5' to 3' exonuclease activity of pol I DNA polymerases include:

mutagenesis (as described in Xu et al., 1997, *J. Mol. Biol.*, 268:284 and Kim et al., 1997, *Mol. Cells*, 7:468).

N-truncation by proteolytic digestion (as described in Klenow et al., 1971, *Eur. J. Biochem.*, 22: 371), or N-truncation by cloning and expressing as C-terminal fragments (as described in Lawyer et al., 1993, *PCR Methods Appl.*, 2:275).

As for archaeal sources, the assay-temperature requirements determine which eubacteria should be used as a source of a DNA polymerase useful according to the invention (e.g., mesophiles, thermophiles, hyperthermophiles).

1. Mesophilic/thermolabile (Useful for 370C Assays)
   i. DNA polymerases naturally substantially lacking 5' to 3' exonuclease activity: pol II or the pol III catalytic subunit from mesophilic eubacteria, such as *Escherichia coli, Streptococcus pneumoniae, Haemophilus influenza, Mycobacterium* species (*tuberculosis, leprae*)
   ii. DNA polymerase mutants substantially lacking 5' to 3' exonuclease activity: Pol I DNA polymerases for N-truncation or mutagenesis can be isolated from the mesophilic eubacteria listed above (Ci). A commercially-available eubacterial DNA polymerase pol I fragment is the Klenow fragment (N-truncated *E. coli* pol I; Stratagene).

2. Thermostable (Useful for non PCR Assays)
   i. DNA polymerases naturally substantially lacking 5' to 3' exonuclease activity: Pol II or the pol III catalytic subunit from thermophilic eubacteria, such as *Bacillus* species (e.g., *stearothermophilus, caldotenax, caldovelox*)
   ii. DNA polymerase mutants substantially lacking 5' to 3' exonuclease activity: Suitable pol I DNA polymerases for N-truncation or mutagenesis can be isolated from thermophilic eubacteria such as the *Bacillus* species listed above. Thermostable N-truncated fragments of *B. stearothermophilus* DNA polymerase pol I are commercially available and sold under the trade names Bst DNA polymerase I large fragment (Bio-Rad and Isotherm DNA polymerase (Epicentre)). A C-terminal fragment of *Bacillus caldotenax* pol I is available from Panvera (sold under the tradename Ladderman).

3. Thermostable (Useful for PCR Assays)
   i. DNA polymerases naturally substantially lacking 5' to 3' exonuclease activity: Pol II or pol III catalytic subunit from *Thermus* species (*aquaticus, thermophilus, flavus, ruber, caldophilus, filiformis, brokianus*) or from *Thermotoga maritima*. The catalytic pol III subunits from *Thermus thermophilus* and *Thermus aquaticus* are described in Yi-Ping et al., 1999, J. Mol. Evol., 48:756 and McHenry et al., 1997, J. Mol. Biol., 272:178.
   ii. DNA polymerase mutants substantially lacking 5' to 3' exonuclease activity: Suitable pol I DNA polymerases for N-truncation or mutagenesis can be isolated from a variety of thermophilic eubacteria, including *Thermus* species and *Thermotoga maritima* (see above). Thermostable fragments of *Thermus aquaticus* DNA polymerase pol I (Taq) are commercially available and sold under the trade names KlenTaq1 (Ab Peptides), Stoffel fragment (Perkin-Elmer), and *ThermoSequenase* (Amersham). In addition to C-terminal fragments, 5' to 3' exonuclease⁻ Taq mutants are also commercially available, such as TaqFS (Hoffman-LaRoche). In addition to 5'-3' exonuclease⁻ versions of Taq, an N-truncated version of *Thermotoga maritima* DNA polymerase I is also commercially available (tradename U1Tma, Perkin-Elmer).

Additional eubacteria related to those listed above are described in *Thermophilic Bacteria* (Kristjansson, J. K., ed.) CRC Press, Inc., Boca Raton, Fla., 1992.

D. Eukaryotic 5' to 3' Exonuclease⁻ DNA polymerases (Useful for 37° C. Assays)

There are several DNA polymerases that have been identified in eukaryotes, including DNA pol $\alpha$ (replication/repair), $\delta$ (replication), $\epsilon$ (replication), $\beta$ (repair) and $\gamma$ (mitochondrial replication). Eukaryotic DNA polymerases are devoid of 5' to 3' exonuclease activity, as this activity is encoded by a separate polypeptide (e.g., mammalian FEN-1 or yeast RAD2). Suitable thermolabile DNA polymerases may be isolated from a variety of eukaryotes (including but not limited to yeast, mammalian cells, insect cells, *Drosophila*) and eukaryotic viruses (e.g., EBV, adenovirus).

It is possible that DNA polymerase mutants lacking 3'-5' exonuclease (proofreading) activity, in addition to lacking 5' to 3' exonuclease activity, could exhibit improved performance in FEN-based detection strategies. For example, reducing or abolishing inherent 3' to 5' exonuclease activity may lower background signals by diminishing non-specific exonucleolytic degradation of labeled probes. Three 3' to 5' exonuclease motifs have been identified, and mutations in these regions have been shown to abolish 3' to 5' exonuclease activity in Klenow, φ29, T4, T7, and Vent DNA polymerases, yeast Pol α, Pol β, and Pol γ, and *Bacillus subtilis* Pol III (reviewed in Derbeyshire et al., 1995, Methods. Enzymol. 262:363). Methods for preparing additional DNA polymerase mutants, with reduced or abolished 3' to 5' exonuclease activity, are well known in the art.

Commercially-available enzymes that lack both 5' to 3' and 3' to 5' exonuclease activities include Sequenase (exo⁻ T7; USB), Pfu exo⁻ (Stratagene), exo⁻ Vent (New England BioLabs), exo⁻ DeepVent (New England BioLabs), exo⁻ Klenow fragment (Stratagene), Bst (Bio-Rad), Isotherm (Epicentre), Ladderman (Panvera), KlenTaq1 (Ab Peptides), Stoffel fragment (Perkin-Elmer), ThermoSequenase (USB), and TaqFS (Hoffman-LaRoche).

If polymerases other than Pfu are used, buffers and extension temperatures are selected to allow for optimal activity by the particular polymerase useful according to the invention. Buffers and extension temperatures useful for polymerases according to the invention are know in the art and can also be determined from the Vendor's specifications.

III. Nucleic Acids

A. Nucleic Acid Sequences Useful in the Invention

The invention provides for methods of detecting or measuring a target nucleic acid sequence; and also utilizes oligonucleotides, primers and probes for forming a cleavage structure according to the invention and primers for amplifying a template nucleic acid sequence. As used herein, the terms "nucleic acid", "polynucleotide" and "oligonucleotide" refer to primers, probes, and oligomer fragments to be detected, and shall be generic to polydeoxyribonucleotides (containing 2-deoxy-D-ribose), to polyribonucleotides (containing D-ribose), and to any other type of polynucleotide which is an N-glycoside of a purine or pyrimidine base, or modified purine or pyrimidine bases (including abasic sites). There is no intended distinction in length between the term "nucleic acid", "polynucleotide" and "oligonucleotide", and these terms will be used interchangeably. These terms refer only to the primary structure of the molecule. Thus, these terms include double- and single-stranded DNA, as well as double- and single-stranded RNA.

The complement of a nucleic acid sequence as used herein refers to an oligonucleotide which, when aligned with the nucleic acid sequence such that the 5' end of one sequence is paired with the 3' end of the other, is in "antiparallel association."

The oligonucleotide is not necessarily physically derived from any existing or natural sequence but may be generated in any manner, including chemical synthesis, DNA replication, reverse transcription or a combination thereof. The terms "oligonucleotide" or "nucleic acid" intend a polynucleotide of genomic DNA or RNA, cDNA, semisynthetic, or synthetic origin which, by virtue of its synthetic origin or manipulation: (1) is not associated with all or a portion of the polynucleotide with which it is associated in nature; and/or (2) is linked to a polynucleotide other than that to which it is linked in nature.

Oligonucleotides, according to the present invention, additionally comprise nucleic acid sequences which function as probes and can have secondary structure such as hairpins and stem-loops. Such oligonucleotide probes include, but are not limited to the molecular beacons, safteypins, scorpions, and sunrise/amplifluor probes described herein.

Because mononucleotides are reacted to make oligonucleotides in a manner such that the 5' phosphate of one mononucleotide pentose ring is attached to the 3' oxygen of its neighbor in one direction via a phosphodiester linkage, an end of oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends.

When two different, non-overlapping oligonucleotides anneal to different regions of the same linear complementary nucleic acid sequence, and the 3' end of one oligonucleotide points toward the 5' end of the other, the former may be called the "upstream" oligonucleotide and the latter the "downstream" oligonucleotide.

Certain bases not commonly found in natural nucleic acids may be included in the nucleic acids of the present invention and include, for example, inosine and 7-deazaguanine. Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength, and incidence of mismatched base pairs.

Stability of a nucleic acid duplex is measured by the melting temperature, or "$T_m$". The $T_m$ of a particular nucleic acid duplex under specified conditions is the temperature at which half of the base pairs have disassociated.

B. Primers and Probes Useful According to the Invention

The invention provides for oligonucleotide primers and probes useful for detecting or measuring a nucleic acid, for amplifying a template nucleic acid sequence, and for forming a cleavage structure according to the invention.

The term "primer" may refer to more than one primer and refers to an oligonucleotide, whether occurring naturally, as in a purified restriction digest, or produced synthetically, which is capable of acting as a point of initiation of synthesis along a complementary strand when placed under conditions in which synthesis of a primer extension product which is complementary to a nucleic acid strand is catalyzed. Such conditions include the presence of four different deoxyribonucleoside triphosphates and a polymerization-inducing agent such as DNA polymerase or reverse transcriptase, in a suitable buffer ("buffer" includes substituents which are cofactors, or which affect pH, ionic strength, etc.), and at a suitable temperature. The primer is preferably single-stranded for maximum efficiency in amplification.

Oligonucleotide primers useful according to the invention are single-stranded DNA or RNA molecules that are hybridizable to a template nucleic acid sequence and prime enzymatic synthesis of a second nucleic acid strand. The primer is complementary to a portion of a target molecule present in a pool of nucleic acid molecules. It is contemplated that oligonucleotide primers according to the invention are prepared by synthetic methods, either chemical or enzymatic. Alternatively, such a molecule or a fragment thereof is naturally-occurring, and is isolated from its natural source or purchased from a commercial supplier. Oligonucleotide primers and probes are 5 to 100 nucleotides in length, ideally from 17 to 40 nucleotides, although primers and probes of different length are of use. Primers for amplification are preferably about 17-25 nucleotides. Primers for the production of a cleavage structure according to the invention are preferably about 17-45 nucleotides. Primers useful according to the invention are also designed to have a particular melting temperature (Tm) by the method of melting temperature estimation. Commercial programs, including Oligo™, Primer Design and programs available on the internet, including Primer3 and Oligo Calculator can be used to calculate a Tm of a nucleic acid sequence useful according to the invention. Preferably, the Tm of an amplification primer useful according to the invention, as calculated for example by Oligo Calculator, is preferably between about 45 and 65° C. and more preferably between about 50 and 60° C. Preferably, the Tm of a probe useful according to the invention is 7° C. higher than the Tm of the corresponding amplification primers.

As used herein, "probe" refers to a labeled oligonucleotide that can be a primer, useful for preparation of a cleavage structure according to the invention. Pairs of single-stranded DNA primers can be annealed to sequences within a target nucleic acid sequence or can be used to prime amplifying DNA synthesis of a target nucleic acid sequence.

Typically, selective hybridization occurs when two nucleic acid sequences are substantially complementary (at least about 65% complementary over a stretch of at least 14 to 25 nucleotides, preferably at least about 75%, more preferably at least about 90% complementary). See Kanehisa, M., 1984, Nucleic Acids Res. 12: 203, incorporated herein by reference. As a result, it is expected that a certain degree of mismatch at the priming site is tolerated. Such mismatch may be small, such as a mono-, di- or trinucleotide. Alternatively, a region of mismatch may encompass loops, which are defined as regions in which there exists a mismatch in an uninterrupted series of four or more nucleotides.

Numerous factors influence the efficiency and selectivity of hybridization of the primer to a second nucleic acid molecule. These factors, which include primer length, nucleotide sequence and/or composition, hybridization temperature, buffer composition and potential for steric hindrance in the region to which the primer is required to hybridize, will be considered when designing oligonucleotide primers according to the invention.

A positive correlation exists between primer length and both the efficiency and accuracy with which a primer will anneal to a target sequence. In particular, longer sequences have a higher melting temperature ($T_M$) than do shorter ones, and are less likely to be repeated within a given target sequence, thereby minimizing promiscuous hybridization. Primer sequences with a high G-C content or that comprise palindromic sequences tend to self-hybridize, as do their intended target sites, since unimolecular, rather than bimolecular, hybridization kinetics are generally favored in solution. However, it is also important to design a primer that contains sufficient numbers of G-C nucleotide pairings since each G-C pair is bound by three hydrogen bonds, rather than the two that are found when A and T bases pair to bind the target sequence, and therefore forms a tighter, stronger bond. Hybridization temperature varies inversely with primer annealing efficiency, as does the concentration of organic solvents, e.g. formamide, that might be included in a priming reaction or hybridization mixture, while increases in salt concentration facilitate binding. Under stringent annealing conditions, longer hybridization probes, or synthesis primers, hybridize more efficiently than do shorter ones, which are sufficient under more permissive conditions. Stringent hybridization conditions typically include salt concentrations of less than about 1M, more usually less than about 500 mM and preferably less than about 200 mM. Hybridization temperatures range from as low as 0° C. to greater than 22° C., greater than about 30° C., and (most often) in excess of about 37° C. Longer fragments may require higher hybridization temperatures for specific hybridization. As several factors affect the stringency of hybridization, the combination of parameters is more important than the absolute measure of a single factor.

Oligonucleotide primers can be designed with these considerations in mind and synthesized according to the following methods.

1. Oligonucleotide Primer Design Strategy

The design of a particular oligonucleotide primer for the purpose of sequencing, PCR or for the preparation of a cleavage structure according to the invention, involves selecting a sequence that is capable of recognizing the target sequence, but has a minimal predicted secondary structure. The oligonucleotide sequence binds only to a single site in the target nucleic acid sequence. Furthermore, the Tm of the oligonucleotide is optimized by analysis of the length and GC content of the oligonucleotide. Furthermore, when designing a PCR primer useful for the amplification of genomic DNA, the selected primer sequence does not demonstrate significant matches to sequences in the GenBank database (or other available databases).

The design of a primer is facilitated by the use of readily available computer programs, developed to assist in the evaluation of the several parameters described above and the optimization of primer sequences. Examples of such programs are "PrimerSelect" of the DNAStar™ software package (DNAStar, Inc.; Madison, Wis.), OLIGO 4.0 (National Biosciences, Inc.), PRIMER, Oligonucleotide Selection Program, PGEN and Amplify (described in Ausubel et al., 1995, Short Protocols in Molecular Biology, 3rd Edition, John Wiley & Sons). In one embodiment, primers are designed with sequences that serve as targets for other primers to produce a PCR product that has known sequences on the ends which serve as targets for further amplification (e.g. to sequence the PCR product). If many different target nucleic acid sequences are amplified with specific primers that share a common 'tail' sequence', the PCR products from these distinct genes can subsequently be sequenced with a single set of primers. Alternatively, in order to facilitate subsequent cloning of amplified sequences, primers are designed with restriction enzyme site sequences appended to their 5' ends. Thus, all nucleotides of the primers are derived from a target nucleic acid sequence or sequences adjacent to a target nucleic acid sequence, except for the few nucleotides necessary to form a restriction enzyme site. Such enzymes and sites are well known in the art. If the genomic sequence of a target nucleic acid sequence and the sequence of the open reading frame of a target nucleic acid sequence are known, design of particular primers is well within the skill of the art.

It is well known by those with skill in the art that oligonucleotides can be synthesized with certain chemical and/or capture moieties, such that they can be coupled to solid supports. Suitable capture moieties include, but are not limited to, biotin, a hapten, a protein, a nucleotide sequence, or a chemically reactive moiety. Such oligonucleotides may either be used first in solution, and then captured onto a solid support, or first attached to a solid support and then used in a detection reaction. An example of the latter would be to couple a downstream probe molecule to a solid support, such that the 5' end of the downstream probe molecule comprised a fluorescent quencher. The same downstream probe molecule would also comprise a fluorophore in a location such that a FEN nuclease cleavage would physically separate the quencher from the fluorophore. For example, the target nucleic acid could hybridize with the solid-phase downstream probe oligonucleotide, and a liquid phase upstream primer could also hybridize with the target molecule, such that a FEN cleavage reaction occurs on the solid support and liberates the 5' quencher moiety from the complex. This would cause the solid support-bound fluorophore to be detectable, and thus reveal the presence of a cleavage event upon a suitably labeled or identified solid support. Different downstream probe molecules could be bound to different locations on an array. The location on the array would identify the probe molecule, and indicate the presence of the template to which the probe molecule can hybridize.

2. Synthesis

The primers themselves are synthesized using techniques that are also well known in the art. Methods for preparing oligonucleotides of specific sequence are known in the art, and include, for example, cloning and restriction digest analysis of appropriate sequences and direct chemical synthesis. Once designed, oligonucleotides are prepared by a suitable chemical synthesis method, including, for example, the phosphotriester method described by Narang et al., 1979, Methods in Enzymology, 68:90, the phosphodiester method disclosed by Brown et al., 1979, Methods in Enzymology, 68:109, the diethylphosphoramidite method disclosed in Beaucage et al., 1981, Tetrahedron Letters, 22:1859, and the solid support method disclosed in U.S. Pat. No. 4,458,066, or by other chemical methods using either a commercial automated oligonucleotide synthesizer (which is commercially available) or VLSIPS™ technology.

C. Probes

The invention provides for probes useful for forming a labeled cleavage structure as defined herein. Methods of preparing a labeled cleavage structure according to the invention are provided in the section entitled "Cleavage Structure" below.

As used herein, the term "probe" refers to a labeled oligonucleotide which forms a duplex structure with a sequence in the target nucleic acid, due to complementarity of at least one sequence in the probe with a sequence in the target region. Probe lengths useful in the invention are preferably 10-50 nucleotides, and more preferably 16-25 nucleotides. The probe, preferably, does not contain a sequence complementary to sequence(s) used in the primer extension (s). Generally the 3' terminus of the probe will be "blocked" to prohibit incorporation of the probe into a primer extension product. "Blocking" can be achieved by using non-complementary bases or by adding a chemical moiety such as biotin or a phosphate group to the 3' hydroxyl of the last nucleotide, which may, depending upon the selected moiety, serve a dual purpose by also acting as a label for subsequent detection or capture of the nucleic acid attached to the label. Blocking can also be achieved by removing the 3'-OH or by using a nucleotide that lacks a 3'-OH such as dideoxynucleotide.

Additionally, according to the present invention, a probe can be an oligonucleotide with secondary structure such as a hairpin or a stem-loop, and includes, but is not limited to molecular beacons, safety pins, scorpions, and sunrise/amplifluor probes.

Molecular beacon probes comprise a hairpin, or stem-loop structure which possesses a pair of interactive signal generating labeled moieties (e.g., a fluorophore and a quencher) effectively positioned to quench the generation of a detectable signal. The loop comprises a region that is complementary to a target nucleic acid. The loop is flanked by 5' and 3' regions ("arms") that reversibly interact with one another by means of complementary nucleic acid sequences when the region of the probe that is complementary to a nucleic acid target sequence is not bound to the target nucleic acid. Alternatively, the loop is flanked by 5' and 3' regions ("arms") that reversibly interact with one another by means of attached members of an affinity pair to form a secondary structure when the region of the probe that is complementary to a nucleic acid target sequence is not bound to the target nucleic acid. As used herein, "arms" refers to regions of a probe that reversibly interact with one another by means of complementary nucleic acid sequences when the region of the probe that is complementary to a nucleic acid target sequence is not bound to the target nucleic acid or regions of a probe that reversibly interact with one another by means of attached members of an affinity pair to form a secondary structure when the region of the probe that is complementary to a nucleic acid target sequence is not bound to the target nucleic acid. When a molecular beacon probe is not hybridized to target, the arms hybridize with one another to form a stem hybrid, which is sometimes referred to as the "stem duplex". This is the closed conformation. When a molecular beacon probe hybridizes to its target the "arms" of the probe are separated. This is the open conformation. In the open conformation an arm may also hybridize to the target. Such probes may be free in solution, or they may be tethered to a solid surface. When the arms are hybridized (e.g., form a stem) the quencher is very close to the fluorophore and effectively quenches or suppresses its fluorescence, rendering the probe dark. Such probes are described in U.S. Pat. No. 5,925,517 and U.S. Pat. No. 6,037,130.

As used herein, a molecular beacon probe that is an "allele-discriminating" probe will not hybridize sufficiently to a target-like nucleic acid sequence that contains one or more internally located nucleotide mismatches as compared to the target nucleic acid complementary sequence and thus will not convert conformationally to an open conformation in the presence of a target-like nucleic acid sequence, and under conditions that would support hybridization of the allele discriminating probe to a target nucleic acid sequence. In other embodiments a molecular beacon probe will hybridize sufficiently to a target-like nucleic acid sequence that contains one or more internally located nucleotide mismatches as compared to the target nucleic acid complementary sequence and will convert conformationally to an open conformation in the presence of a target-like nucleic acid sequence, and under conditions that would support hybridization of the allele discriminating probe to a target nucleic acid sequence. Molecular beacon probes have a fluorophore attached to one arm and a quencher attached to the other arm. The fluorophore and quencher, for example, tetramethylrhodamine and DABCYL, need not be a FRET pair.

For stem loop probes useful in this invention, the length of the probe sequence that is complementary to the target, the length of the regions of a probe (e.g., stem hybrid) that reversibly interact with one another by means of complementary nucleic acid sequences when the region complementary to a nucleic acid target sequence is not bound to the target nucleic acid and the relation of the two is designed according to the assay conditions for which the probe is to be utilized. The lengths of the target-complementary sequences and the stem hybrid sequences for particular assay conditions can be estimated according to what is known in the art. The regions of a probe that reversibly interact with one another by means of complementary nucleic acid sequences when the region of the probe that is complementary to a nucleic acid target sequence is not bound to the target nucleic acid are in the range of 6 to 100, preferably 8 to 50 nucleotides and most preferably 8 to 25 nucleotides each. The length of the probe sequence that is complementary to the target is preferably 17-40 nucleotides, more preferably 17-30 nucleotides and most preferably 17-25 nucleotides long. The stability of the interaction between the regions of a probe that reversibly interact with one another by means of complementary nucleic acid sequences is determined by routine experimentation to achieve proper functioning.

The oligonucleotide sequences of molecular beacon probes modified according to this invention may be DNA, RNA, cDNA or combinations thereof. Modified nucleotides may be included, for example nitropyrole-based nucleotides or 2'-O-methylribonucleotides. Modified linkages also may be included, for example phosphorothioates. Modified nucleotides and modified linkages may also be incorporated in wavelength-shifting primers according to this invention.

Figure 10:
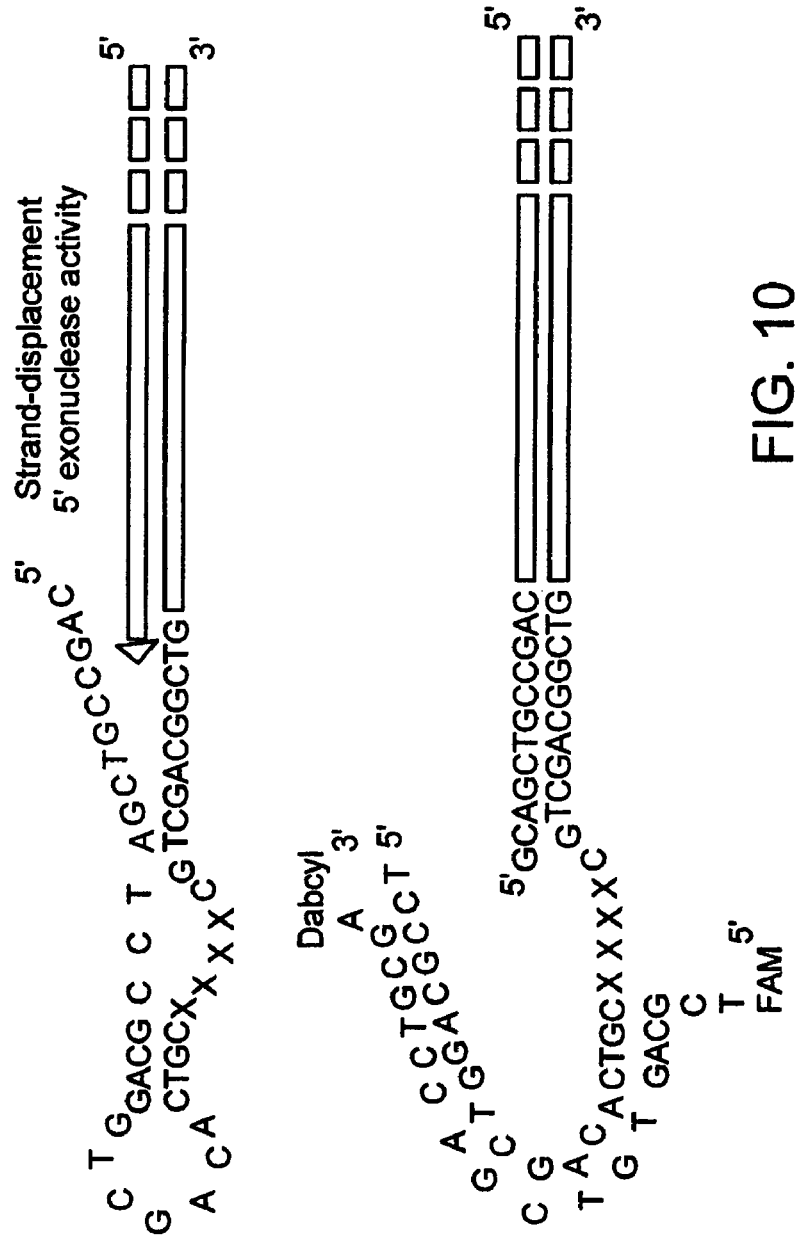
FIG. 10 is a representation of a safety pin probe.

A safety pin probe, as utilized in the present invention, requires a "universal" hairpin probe 1 (FIG. 10, b171), comprising a hairpin structure, with a fluorophore (FAM) on the 5' arm of the hairpin and a quencher (Dabcyl) on the 3' arm, and a probe 2 (FIG. 10, SP 170a) comprising a stem-loop comprising two domains: the 5' two thirds of probe 2 have a (universal) sequence complementary to the hairpin probe 1, and nucleotides that will stop the DNA polymerase, and the 3' one third of probe 2, which serves as the target specific primer. As the polymerase, primed from the reverse primer (that is, the 3' one third of probe 2) synthesizes the top strand, the 5' end of probe 2 will be displaced and degraded by the 5' exonucleolytic activity until the "stop nucleotides" are reached. At this time the remainder of probe 2 opens up or unfolds and serves as a target for hairpin probe 1, thereby separating the fluorophore from the quencher (FIG. 10).

Figure 11:
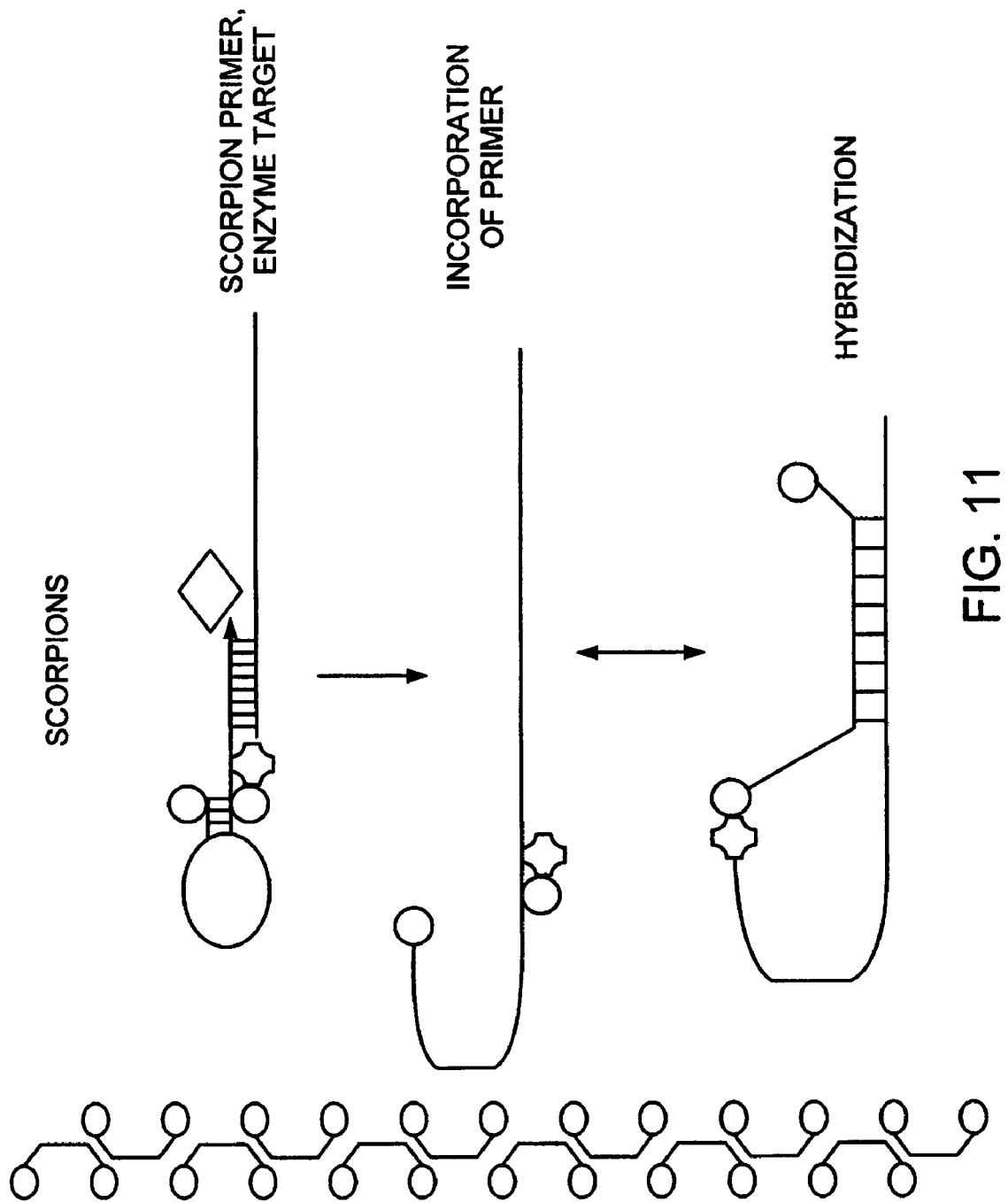
FIG. 11 is a representation of a scorpion probe.

Scorpion probes, as used in the present invention comprise a 3' primer with a 5' extended probe tail comprising a hairpin structure which possesses a fluorophore/quencher pair. The probe tail is "protected" from replication in the 5' to3' direction by the inclusion of hexethlyene glycol (HEG) which blocks the polymerase from replicating the probe. During the first round of amplification the 3' target-specific primer anneals to the target and is extended such that the scorpion is now incorporated into the newly synthesized strand, which possesses a newly synthesized target region for the 5' probe. During the next round of denaturation and annealing, the probe region of the scorpion hairpin loop will hybridize to the target, thus separating the fluorophore and quencher and creating a measurable signal. Such probes are described in Whitcombe et al., *Nature Biotechnology* 17: 804-807 (1999), and in FIG. 11.

Figure 12:
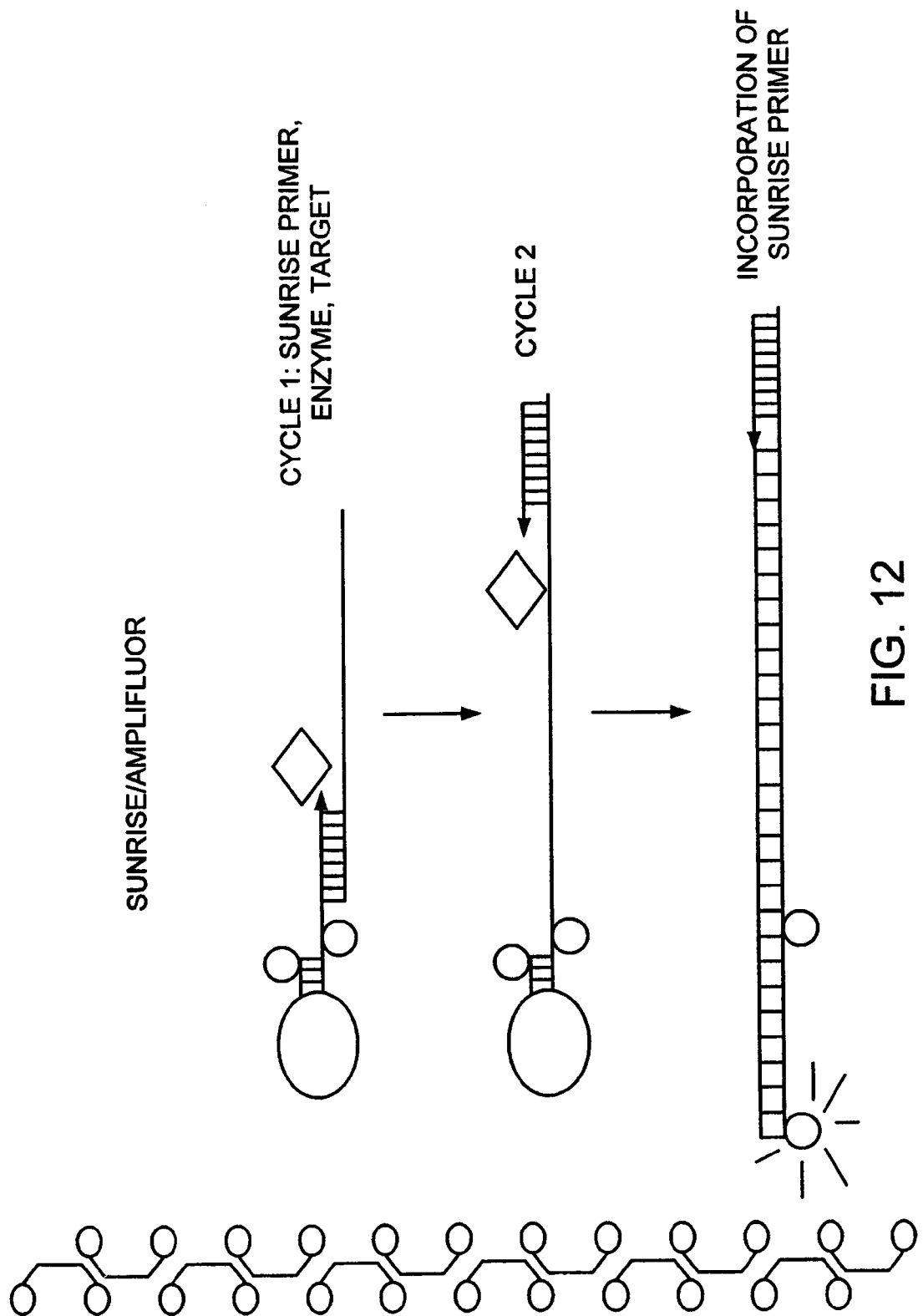
FIG. 12 is a representation of a sunrise/amplifluor probe

An additional oligonucleotide probe useful in the present invention is the sunrise/amplifluor probe. The sunrise/amplifluor probe is of similar construction as the scorpion probe with the exception that is lacks the HEG monomer to block the 5' to3' replication of the hairpin probe region. Thus, in the first round of amplification, the 3' target specific primer of the sunrise/amplifluor anneals to the target and is extended, thus incorporating the hairpin probe into the newly synthesized strand (sunrise strand). During the second round of amplification a second, non-labeled primer anneals to the 3' end of the sunrise strand (Cycle 2 in FIG. 12). However, as the polymerase reaches the 5' end of the hairpin, due to the lack of the HEG stop sequence, the polymerase will displace and replicate the hairpin, thus separating the fluorophore and quencher, and incorporating the linearized hairpin probe into the new strand. Probes of this type are described further in Nazarneko et al., *Nucleic Acid Res.* 25: 2516-2521 (1997), and in FIG. 12.

For probes useful in this invention, the length of the probe sequence that is complementary to the target, the length of the regions of a probe (e.g., stem hybrid) that reversibly interact with one another by means of complementary nucleic acid sequences when the region complementary to a nucleic acid target sequence is not bound to the target nucleic acid and the relation of the two is designed according to the assay conditions for which the probe is to be utilized. The lengths of the target-complementary sequences and the stem hybrid sequences for particular assay conditions can be estimated according to what is known in the art. The regions of a probe that reversibly interact with one another by means of complementary nucleic acid sequences when the region complementary to a nucleic acid target sequence is not bound to the target nucleic acid are in the range of 6 to 100, preferably 8 to 50 nucleotides and most preferably 8 to 25 nucleotides each. The length of the probe sequence that is complementary to the target is preferably 17-40 nucleotides, more preferably 17-30 nucleotides and most preferably 17-25 nucleotides long. The stability of the interaction between the regions of a probe that reversibly interact with one another by means of complementary nucleic acid sequences is determined by routine experimentation to achieve proper functioning. In addition to length, stability of the interaction the regions of a probe that reversibly interact with one another by means of complementary nucleic acid sequences between the regions of a probe that reversibly interact with one another by means of complementary nucleic acid sequences can be adjusted by altering the G-C content and inserting destabilizing mismatches. One of the regions of a probe that reversibly interact with one another by means of complementary nucleic acid sequences can be designed to be partially or completely complementary to the target. If the 3' arm is complementary to the target the probe can serve as a primer for a DNA polymerase. Also, wavelength-shifting molecular beacon probes can be immobilized to solid surfaces, as by tethering, or be free-floating.

A wide range of fluorophores may be used in probes and primers according to this invention. Available fluorophores include coumarin, fluorescein, tetrachlorofluorescein, hexachlorofluorescein, Lucifer yellow, rhodamine, BODIPY, tetramethylrhodamine, Cy3, Cy5, Cy7, eosine, Texas red and ROX. Combination fluorophores such as fluorescein-rhodamine dimers, described, for example, by Lee et al. (1997), Nucleic Acids Research 25:2816, are also suitable. Fluorophores may be chosen to absorb and emit in the visible spectrum or outside the visible spectrum, such as in the ultraviolet or infrared ranges.

A quencher is a moiety that, when placed very close to an excited fluorophore, causes there to be little or no fluorescence. Suitable quenchers described in the art include particularly DABCYL and variants thereof, such as DABSYL, DABMI and Methyl Red. Fluorophores can also be used as quenchers, because they tend to quench fluorescence when touching certain other fluorophores. Preferred quenchers are either chromophores such as DABCYL or malachite green, or fluorophores that do not fluoresce in the detection range when the probe is in the open conformation.

Methods of labeling a probe according to the invention and suitable labels are described below in the section entitled "Cleavage Structure".

D. Production of a Nucleic Acid

The invention provides nucleic acids to be detected and or measured, for amplification of a target nucleic acid sequence and for formation of a cleavage structure.

The present invention utilizes nucleic acids comprising RNA, cDNA, genomic DNA, synthetic forms, and mixed polymers. The invention includes both sense and antisense strands of a nucleic acid. According to the invention, the nucleic acid may be chemically or biochemically modified or may contain non-natural or derivatized nucleotide bases. Such modifications include, for example, labels, methylation, substitution of one or more of the naturally occurring nucleotides with an analog, internucleotide modifications such as uncharged linkages (e.g. methyl phosphonates, phosphorodithioates, etc.), pendent moieties (e.g., polypeptides), intercalators, (e.g. acridine, psoralen, etc.) chelators, alkylators, and modified linkages (e.g. alpha anomeric nucleic acids, etc.) Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

1. Nucleic Acids Comprising DNA a. Cloning

Nucleic acids comprising DNA can be isolated from cDNA or genomic libraries by cloning methods well known to those skilled in the art (Ausubel et al., supra). Briefly, isolation of a DNA clone comprising a particular nucleic acid sequence involves screening a recombinant DNA or cDNA library and identifying the clone containing the desired sequence. Cloning will involve the following steps. The clones of a particular library are spread onto plates, transferred to an appropriate substrate for screening, denatured, and probed for the presence of a particular nucleic acid. A description of hybridization conditions, and methods for producing labeled probes is included below.

The desired clone is preferably identified by hybridization to a nucleic acid probe or by expression of a protein that can be detected by an antibody. Alternatively, the desired clone is identified by polymerase chain amplification of a sequence defined by a particular set of primers according to the methods described below.

The selection of an appropriate library involves identifying tissues or cell lines that are an abundant source of the desired sequence. Furthermore, if a nucleic acid of interest contains regulatory sequence or intronic sequence a genomic library is screened (Ausubel et al., supra).

b. Genomic DNA

Nucleic acid sequences of the invention are amplified from genomic DNA. Genomic DNA is isolated from tissues or cells according to the following method.

To facilitate detection of a variant form of a gene from a particular tissue, the tissue is isolated free from surrounding normal tissues. To isolate genomic DNA from mammalian tissue, the tissue is minced and frozen in liquid nitrogen. Frozen tissue is ground into a fine powder with a prechilled mortar and pestle, and suspended in digestion buffer (100 mM NaCl, 10 mM Tris-HCl, pH 8.0, 25 mM EDTA, pH 8.0, 0.5% (w/v) SDS, 0.1 mg/ml proteinase K) at 1.2 ml digestion buffer per 100 mg of tissue. To isolate genomic DNA from mammalian tissue culture cells, cells are pelleted by centrifugation for 5 min at 500×g, resuspended in 1-10 ml ice-cold PBS, repelleted for 5 min at 500×g and resuspended in 1 volume of digestion buffer.

Samples in digestion buffer are incubated (with shaking) for 12-18 hours at 50° C., and then extracted with an equal volume of phenol/chloroform/isoamyl alcohol. If the phases are not resolved following a centrifugation step (10 min at 1700×g), another volume of digestion buffer (without proteinase K) is added and the centrifugation step is repeated.

If a thick white material is evident at the interface of the two phases, the organic extraction step is repeated. Following extraction the upper, aqueous layer is transferred to a new tube to which will be added ½ volume of 7.5M ammonium acetate and 2 volumes of 100% ethanol. The nucleic acid is pelleted by centrifugation for 2 min at 1700×g, washed with 70% ethanol, air dried and resuspended in TE buffer (10 mM Tris-HCl, pH 8.0, 1 mM EDTA, pH 8.0) at 1 mg/ml. Residual RNA is removed by incubating the sample for 1 hour at 370 C. in the presence of 0. 1% SDS and 1 µg/ml DNase-free RNase, and repeating the extraction and ethanol precipitation steps. The yield of genomic DNA, according to this method is expected to be approximately 2 mg DNA/1 g cells or tissue (Ausubel et al., supra). Genomic DNA isolated according to this method can be used for PCR analysis, according to the invention.

c. Restriction Digest (of cDNA or Genomic DNA)

Following the identification of a desired cDNA or genomic clone containing a particular target nucleic acid sequence, nucleic acids of the invention may be isolated from these clones by digestion with restriction enzymes.

The technique of restriction enzyme digestion is well known to those skilled in the art (Ausubel et al., supra). Reagents useful for restriction enzyme digestion are readily available from commercial vendors including Stratagene, as well as other sources.

d. PCR

Nucleic acids of the invention may be amplified from genomic DNA or other natural sources by the polymerase chain reaction (PCR). PCR methods are well-known to those skilled in the art.

PCR provides a method for rapidly amplifying a particular DNA sequence by using multiple cycles of DNA replication catalyzed by a thermostable, DNA-dependent DNA polymerase to amplify the target sequence of interest. PCR requires the presence of a target nucleic acid sequence to be amplified, two single stranded oligonucleotide primers flanking the sequence to be amplified, a DNA polymerase, deoxyribonucleoside triphosphates, a buffer and salts.

PCR, is performed as described in Mullis and Faloona, 1987, Methods Enzymol., 155: 335, herein incorporated by reference.

The polymerase chain reaction (PCR) technique, is disclosed in U.S. Pat. Nos. 4,683,202, 4,683,195 and 4,800, 159. In its simplest form, PCR is an in vitro method for the enzymatic synthesis of specific DNA sequences, using two oligonucleotide primers that hybridize to opposite strands and flank the region of interest in the target DNA. A repetitive series of reaction steps involving template denaturation, primer annealing and the extension of the annealed primers by DNA polymerase results in the exponential accumulation of a specific fragment whose termini are defined by the 5' ends of the primers. PCR is reported to be capable of producing a selective enrichment of a specific DNA sequence by a factor of $10^9$. The PCR method is also described in Saiki et al., 1985, Science 230:1350.

PCR is performed using template DNA (at least 1 fg; more usefully, 1-1000 ng) and at least 25 pmol of oligonucleotide primers. A typical reaction mixture includes: 2 µl of DNA, 25 pmol of oligonucleotide primer, 2.5 µl of a suitable buffer, 0.4 µl of 1.25 µM dNTP, 2.5 units of Taq DNA polymerase (Stratagene) and deionized water to a total volume of 25 µl. Mineral oil is overlaid and the PCR is performed using a programmable thermal cycler.

The length and temperature of each step of a PCR cycle, as well as the number of cycles, are adjusted according to the stringency requirements in effect. Annealing temperature and timing are determined both by the efficiency with which a primer is expected to anneal to a template and the degree of mismatch that is to be tolerated. The ability to optimize the stringency of primer annealing conditions is well within the knowledge of one of moderate skill in the art. An annealing temperature of between 30° C. and 72° C. is used. Initial denaturation of the template molecules normally occurs at between 92° C. and 99° C. for 4 minutes, followed by 20-40 cycles consisting of denaturation (94-99° C. for 15 seconds to 1 minute), annealing (temperature determined as discussed above; 1-2 minutes), and extension (72° C. for 1 minute). The final extension step is generally carried out for 4 minutes at 72° C., and may be followed by an indefinite (0-24 hour) step at 4° C.

Detection methods generally employed in standard PCR techniques use a labeled probe with the amplified DNA in a hybridization assay. Preferably, the probe is labeled, e.g., with $^{32}$P, biotin, horseradish peroxidase (HRP), etc., to allow for detection of hybridization.

Other means of detection include the use of fragment length polymorphism (PCR FLP), hybridization to allele-specific oligonucleotide (ASO) probes (Saiki et al., 1986, *Nature* 324:163), or direct sequencing via the dideoxy method (using amplified DNA rather than cloned DNA). The standard PCR technique operates (essentially) by replicating a DNA sequence positioned between two primers, providing as the major product of the reaction a DNA sequence of discrete length terminating with the primer at the 5' end of each strand. Thus, insertions and deletions between the primers result in product sequences of different lengths, which can be detected by sizing the product in PCR-FLP. In an example of ASO hybridization, the amplified DNA is fixed to a nylon filter (by, for example, UV irradiation) in a series of "dot blots", then allowed to hybridize with an oligonucleotide probe labeled with HRP under stringent conditions. After washing, terramethylbenzidine (TMB) and hydrogen peroxide are added: HRP oxidizes the hydrogen peroxide, which in turn oxidizes the TMB to a blue precipitate, indicating a hybridized probe.

A PCR assay for detecting or measuring a nucleic assay according to the invention is described in the section entitled "Methods of Use".

2. Nucleic Acids Comprising RNA

The present invention also provides a nucleic acid comprising RNA.

Nucleic acids comprising RNA can be purified according to methods well known in the art (Ausubel et al., supra). Total RNA can be isolated from cells and tissues according to methods well known in the art (Ausubel et al., supra) and described below.

RNA is purified from mammalian tissue according to the following method. Following removal of the tissue of interest, pieces of tissue of ≦2 g are cut and quick frozen in liquid nitrogen, to prevent degradation of RNA. Upon the addition of a suitable volume of guanidinium solution (for example 20 ml guanidinium solution per 2 g of tissue), tissue samples are ground in a tissuemizer with two or three 10-second bursts. To prepare tissue guanidinium solution (1 L) 590.8 g guanidinium isothiocyanate is dissolved in approximately 400 ml DEPC-treated H$_2$O. 25 ml of 2 M Tris-HCl, pH 7.5 (0.05 M final) and 20 ml Na$_2$EDTA (0.01 M final) is added, the solution is stirred overnight, the volume is adjusted to 950 ml, and 50 ml 2-ME is added.

Homogenized tissue samples are subjected to centrifugation for 10 min at 12,000×g at 12° C. The resulting supernatant is incubated for 2 min at 65° C. in the presence of 0.1 volume of 20% Sarkosyl, layered over 9 ml of a 5.7M CsCl solution (0.1 g CsCl/ml), and separated by centrifugation overnight at 113,000×g at 22° C. After careful removal of the supernatant, the tube is inverted and drained. The bottom of the tube (containing the RNA pellet) is placed in a 50 ml plastic tube and incubated overnight (or longer) at 4° C. in the presence of 3 ml tissue resuspension buffer (5 mM EDTA, 0.5% (v/v) Sarkosyl, 5% (v/v) 2-ME) to allow complete resuspension of the RNA pellet. The resulting RNA solution is extracted sequentially with 25:24:1 phenol/chloroform/isoamyl alcohol, followed by 24:1 chloroform/isoamyl alcohol, precipitated by the addition of 3 M sodium acetate, pH 5.2, and 2.5 volumes of 100% ethanol, and resuspended in DEPC water (Chirgwin et al., 1979, *Biochemistry*, 18: 5294).

Alternatively, RNA is isolated from mammalian tissue according to the following single step protocol. The tissue of interest is prepared by homogenization in a glass Teflon homogenizer in 1 ml denaturing solution (4M guanidinium thiosulfate, 25 mM sodium citrate, pH 7.0, 0.1M 2-ME, 0.5% (w/v) N-laurylsarkosine) per 100 mg tissue. Following transfer of the homogenate to a 5-ml polypropylene tube, 0.1 ml of 2 M sodium acetate, pH 4, 1 ml water-saturated phenol, and 0.2 ml of 49:1 chloroform/isoamyl alcohol are added sequentially. The sample is mixed after the addition of each component, and incubated for 15 min at 0-4° C. after all components have been added. The sample is separated by centrifugation for 20 min at 10,000×g, 4° C., precipitated by the addition of 1 ml of 100% isopropanol, incubated for 30 minutes at −20° C. and pelleted by centrifugation for 10 minutes at 10,000×g, 4° C. The resulting RNA pellet is dissolved in 0.3 ml denaturing solution, transferred to a microfuge tube, precipitated by the addition of 0.3 ml of 100% isopropanol for 30 minutes at −20° C., and centrifuged for 10 minutes at 10,000×g at 4° C. The RNA pellet is washed in 70% ethanol, dried, and resuspended in 100-200 μl DEPC-treated water or DEPC-treated 0.5% SDS (Chomczynski and Sacchi, 1987, *Anal. Biochem.*, 162: 156).

Nucleic acids comprising RNA can be produced according to the method of in vitro transcription.

The technique of in vitro transcription is well known to those of skill in the art. Briefly, the gene of interest is inserted into a vector containing an SP6, T3 or T7 promoter. The vector is linearized with an appropriate restriction enzyme that digests the vector at a single site located downstream of the coding sequence. Following a phenol/chloroform extraction, the DNA is ethanol precipitated, washed in 70% ethanol, dried and resuspended in sterile water. The in vitro transcription reaction is performed by incubating the linearized DNA with transcription buffer (200 mM Tris-HCl, pH 8.0, 40 mM MgCl$_2$, 10 mM spermidine, 250 NaCl [T7 or T3] or 200 mM Tris-HCl, pH 7.5, 30 mM MgCl$_2$, 10 mM spermidine [SP6]), dithiothreitol, RNase inhibitors, each of the four ribonucleoside triphosphates, and either SP6, T7 or T3 RNA polymerase for 30 min at 37° C. To prepare a radiolabeled polynucleotide comprising RNA, unlabeled UTP will be omitted and $^{35}$S-UTP will be included in the reaction mixture. The DNA template is then removed by incubation with DNaseI. Following ethanol precipitation, an aliquot of the radiolabeled RNA is counted in a scintillation counter to determine the cpm/μl (Ausubel et al., supra).

Alternatively, nucleic acids comprising RNA are prepared by chemical synthesis techniques such as solid phase phosphoramidite (described above).

3. Nucleic Acids Comprising Oligonucleotides

A nucleic acid comprising oligonucleotides can be made by using oligonucleotide synthesizing machines which are commercially available (described above).

IV. Cleavage Structure

The invention provides for a cleavage structure that can be cleaved by a FEN nuclease, and therefore teaches methods of preparing a cleavage structure. The invention also provides a labeled cleavage structure and methods of preparing a labeled cleavage structure.

A. Preparation of a Cleavage Structure

In one embodiment, a cleavage structure according to the invention is formed by incubating a) an upstream, preferably extendable 3' end, preferably an oligonucleotide primer, b) an oligonucleotide probe located not more than 5000 nucleotides downstream of the upstream primer and c) an appropriate target nucleic acid sequence wherein the target sequence is complementary to both primers and d) a suitable buffer (for example Sentinel Molecular Beacon PCR core buffer (Catalog #600500) or 10× Pfu buffer available from Stratagene (Catalog #200536), under conditions that allow the nucleic acid sequence to hybridize to the oligonucleotide primers (for example 95° C. for 2-5 minutes followed by cooling to between approximately 50-60° C.). The optimal temperature will vary depending on the specific probe(s), primers and polymerases. In preferred embodiments of the invention a cleavage structure comprises an overlapping flap wherein the 3' end of an upstream oligonucleotide capable of hybridizing to a target nucleic acid sequence (for example A in FIG. 3) is complementary to 1 or more base pair(s) of the downstream oligonucleotide (for example C in FIG. 3) that is annealed to a target nucleic acid sequence and wherein the 1 base pair overlap is directly downstream of the point of extension of the single stranded flap.

The 3' end of the upstream oligonucleotide primer is extended by the synthetic activity of a polymerase according to the invention such that the newly synthesized 3' end of the upstream oligonucleotide primer partially displaces the 5' end of the downstream oligonucleotide probe. Extension is preferably carried out in the presence of 1× Sentinel Molecular beacon core buffer or 1× Pfu buffer for 15 seconds at 72° C. In one embodiment of the invention, a cleavage structure according to the invention can be prepared by incubating a target nucleic acid sequence with a partially complementary oligonucleotide primer such that the 3' complementary region anneals to the target nucleic acid sequence and the non-complementary 5' region that does not anneal to the target nucleic acid sequence forms a 5' flap. Annealing is preferably carried out under conditions that allow the nucleic acid sequence to hybridize to the oligonucleotide primer (for example 95° C. for 2-5 minutes followed by cooling to between approximately 50-60° C.) in the presence a suitable buffer (for example 1× Sentinel Molecular beacon core buffer or 1× Pfu buffer.

In another embodiment, the cleavage structure according to the invention is formed by incubating a target nucleic acid, 3' blocked upstream oligonucleotide and downstream probe having a 5' flap. This embodiment is described throughout the specification, specifically in Examples 7-13 and their corresponding Figures.

It a further embodiment, the upstream primer having a 3' blocked end is complementary to the target such that there is a distance between the 3' end of the blocked primer and the 5' end of the probe of no nucleotides or a "nick". In other embodiments, the distance between the 3' end of the blocked primer and the 5' end of the probe is 1 nucleotide, 2 nucleotides, 5, 10 or 15 nucleotides or more.

According to this aspect of the invention, a non-overlapping, upstream oligonucleotide that is unable to be extended by a polymerase (a 3'-blocked oligonucleotide such as a 3' phosphate blocked oligonucleotide) is capable of facilitating cleavage of a 5' flap by a nuclease, e.g., FEN.

B. How to Prepare a Labeled Cleavage Structure

In the present invention, a label is attached to an oligonucleotide primer comprising the cleavage structure, thereby forming a probe. Thus, the cleaved mononucleotides or small oligonucleotides which are cleaved by the endonuclease activity of the flap-specific nuclease can be detected.

A labeled cleavage structure according to the invention is formed by incubating a) an upstream extendable 3' end, preferably an oligonucleotide primer, b) a labeled probe located not more than 500 nucleotides downstream of the upstream primer and c) an appropriate target nucleic acid sequence wherein the target sequence is complementary to the oligonucleotides and d) a suitable buffer (for example 1× Sentinel Molecular beacon core buffer or 1× Pfu buffer), under conditions that allow the nucleic acid sequence to hybridize to the oligonucleotide primers (for example 95° C. for 2-5 minutes followed by cooling to between approximately 50-60° C.). A cleavage structure according to the invention also comprises an overlapping flap wherein the 3' end of an upstream oligonucleotide capable of hybridizing to a target nucleic acid sequence (for example A in FIG. 3) is complementary to 1 base pair of the downstream oligonucleotide (for example C in FIG. 3) that is annealed to a target nucleic acid sequence and wherein the 1 base pair overlap is directly downstream of the point of extension of the single stranded flap. The 3' end of the upstream primer is extended by the synthetic activity of a polymerase such that the newly synthesized 3' end of the upstream primer partially displaces the labeled 5' end of the downstream probe. Extension is preferably carried out in the presence of 1× Sentinel Molecular beacon core buffer or 1× Pfu buffer for 15 seconds at 72° C. A cleavage structure according to the invention can be prepared by incubating a target nucleic acid sequence with a probe comprising a non-complementary, labeled, 5' region that does not anneal to the target nucleic acid sequence and forms a 5' flap, and a complementary 3' region that anneals to the target nucleic acid sequence. Annealing is preferably carried out under conditions that allow the nucleic acid sequence to hybridize to the oligonucleotide primer (for example 95° C. for 2-5 minutes followed by cooling to between approximately 50-60° C.) in the presence a suitable buffer (for example 1× Sentinel Molecular beacon core buffer or 1× Pfu buffer).

Subsequently, any of several strategies may be employed to distinguish the uncleaved labeled nucleic acid from the cleaved fragments thereof. In this manner, the present invention permits identification of those samples that contain a target nucleic acid sequence.

The oligonucleotide probe is labeled, as described below, by incorporating moieties detectable by spectroscopic, photochemical, biochemical, immunochemical, enzymatic or chemical means. The method of linking or conjugating the label to the oligonucleotide probe depends, of course, on the type of label(s) used and the position of the label on the probe. Preferably a probe is labeled at the 5' end although probes labeled at the 3' end or labeled throughout the length of the probe are also useful in particular embodiments of the invention.

A variety of labels that would be appropriate for use in the invention, as well as methods for their inclusion in the probe, are known in the art and include, but are not limited to, enzymes (e.g., alkaline phosphatase and horseradish peroxidase) and enzyme substrates, radioactive atoms, fluorescent dyes, chromophores, chemiluminescent labels, electro-chemiluminescent labels, such as Origen™ (Igen), that may interact with each other to enhance, alter, or diminish a signal. Of course, if a labeled molecule is used in a PCR based assay carried out using a thermal cycler instrument, the label must be able to survive the temperature cycling required in this automated process.

Among radioactive atoms, $^{33}$P or, $^{32}$P is preferred. Methods for introducing $^{33}$P or, $^{32}$P into nucleic acids are known in the art, and include, for example, 5' labeling with a kinase, or random insertion by nick translation. "Specific binding partner" refers to a protein capable of binding a ligand molecule with high specificity, as for example in the case of an antigen and a monoclonal antibody specific therefor. Other specific binding partners include biotin and avidin or streptavidin, IgG and protein A, and the numerous receptor-ligand couples known in the art. The above description is not meant to categorize the various labels into distinct classes, as the same label may serve in several different modes. For example, $^{125}$I may serve as a radioactive label or as an electron-dense reagent. HRP may serve as an enzyme or as antigen for a monoclonal antibody. Further, one may combine various labels for desired effect. For example, one might label a probe with biotin, and detect the presence of the probe with avidin labeled with $^{125}$I, or with an anti-biotin monoclonal antibody labeled with HRP. Other permutations and possibilities will be readily apparent to those of ordinary skill in the art and are considered as equivalents within the scope of the instant invention.

Fluorophores for use as labels in constructing labeled probes of the invention include rhodamine and derivatives (such as Texas Red), fluorescein and derivatives (such as 5-bromomethyl fluorescein), Lucifer Yellow, IAEDANS, 7-Me$_2$N-coumarin-4-acetate, 7-OH-4-CH$_3$-coumarin-3-acetate, 7-NH$_2$-4-CH$_3$-coumarin-3-acetate (AMCA), monobromobimane, pyrene trisulfonates, such as Cascade Blue, and monobromorimethyl-ammoniobimane. In general, fluorophores with wide Stokes shifts are preferred, to allow using fluorimeters with filters rather than a monochromometer and to increase the efficiency of detection.

Probes labeled with fluorophores can readily be used in FEN mediated cleavage of a cleavage structure comprising a labeled probe according to the invention. If the label is on the 5'-end of the probe, the FEN generated labeled fragment is separated from the intact, hybridized probe by procedures well known in the art. The fluorescence of the released label is then compared to the label remaining bound to the target. It is not necessary to separate the FEN generated fragment and the probe that remains bound to the target after cleavage in the presence of FEN if the probe is synthesized with a fluorophore, usually at the 5'-end, and a quencher, usually about 20 nucleotides downstream of the dye. Such a dual labeled probe will not fluoresce when intact because the light emitted from the dye is quenched by the quencher. Thus, any fluorescence emitted by an intact probe is considered to be background fluorescence. When a labeled probe is cleaved by a FEN nuclease, dye and quencher are separated and the released fragment will fluoresce. The amount of fluorescence is proportional to the amount of nucleic acid target sequence present in a sample.

In some situations, one can use two interactive labels on a single oligonucleotide with due consideration given for maintaining an appropriate spacing of the labels on the oligonucleotide to permit the separation of the labels during oligonucleotide hydrolysis. Preferred interactive labels useful according to the invention include, but are not limited to rhodamine and derivatives, fluorescein and derivatives, Texas Red, coumarin and derivatives, crystal violet and include, but are not limited to DABCYL, TAMRA and NTB (nitrothiazole blue).

In another embodiment of the invention, detection of the hydrolyzed, labeled probe can be accomplished using, for example, fluorescence polarization, a technique to differentiate between large and small molecules based on molecular tumbling. Large molecules (i.e., intact labeled probe) tumble in solution much more slowly than small molecules. Upon linkage of a fluorescent moiety to the molecule of interest (e.g., the 5' end of a labeled probe), this fluorescent moiety can be measured (and differentiated) based on molecular tumbling, thus differentiating between intact and digested probe.

In yet another embodiment, two labeled nucleic acids are used, each complementary to separate regions of separate strands of a double-stranded target sequence, but not to each other, so that a labeled nucleic acid anneals downstream of each primer. For example, the presence of two probes can potentially double the intensity of the signal generated from a single label and may further serve to reduce product strand reannealing, as often occurs during PCR amplification. The probes are selected so that the probes bind at positions adjacent (downstream) to the positions at which primers bind.

One can also use multiple probes in the present invention to achieve other benefits. For instance, one could test for any number of pathogens in a sample simply by putting as many probes as desired into the reaction mixture; the probes could each comprise a different label to facilitate detection.

One can also achieve allele-specific or species-specific discrimination using multiple probes in the present invention, for instance, by using probes that have different $T_m$s and conducting the annealing/cleavage reaction at a temperature specific for only one probe/allele duplex. One can also achieve allele specific discrimination by using only a single probe and examining the types of cleavage products generated. In this embodiment of the invention, the probe is designed to be exactly complementary, at least in the 5' terminal region, to one allele but not to the other allele(s). With respect to the other allele(s), the probe will be mismatched in the 5' terminal region of the probe so that a different cleavage product will be generated as compared to the cleavage product generated when the probe is hybridized to the exactly complementary allele.

Although probe sequence can be selected to achieve important benefits, one can also realize important advantages by selection of probe labels(s). The labels may be attached to the oligonucleotide directly or indirectly by a variety of techniques. Depending on the precise type of label used, the label can be located at the 5' or 3' end of the probe, located internally in the probe, or attached to spacer arms of various sizes and compositions to facilitate signal interactions. Using commercially available phosphoramidite reagents, one can produce oligomers containing functional groups (e.g., thiols or primary amines) at either the 5- or the 3-terminus via an appropriately protected phosphoramidite, and can label them using protocols described in, for example, PCR Protocols: A Guide to Methods and Applications, Innis et al., eds. Academic Press, Ind., 1990.

Methods for introducing oligonucleotide functionalizing reagents to introduce one or more sulfhydryl, amino or hydroxyl moieties into the oligonucleotide probe sequence, typically at the 5' terminus, are described in U.S. Pat. No.

4,914,210. A 5' phosphate group can be introduced as a radioisotope by using polynucleotide kinase and gamma-$^{32}$P-ATP or gamma-$^{33}$P-ATP to provide a reporter group. Biotin can be added to the 5' end by reacting an aminothymidine residue, or a 6-amino hexyl residue, introduced during synthesis, with an N-hydroxysuccinimide ester of biotin. Labels at the 3' terminus may employ polynucleotide terminal transferase to add the desired moiety, such as for example, cordycepin $^{35}$S-dATP, and biotinylated dUTP.

Oligonucleotide derivatives are also available labels. For example, etheno-dA and etheno-A are known fluorescent adenine nucleotides that can be incorporated into a nucleic acid probe. Similarly, etheno-dC or 2-amino purine deoxyriboside is another analog that could be used in probe synthesis. The probes containing such nucleotide derivatives may be hydrolyzed to release much more strongly fluorescent mononucleotides by flap-specific nuclease activity.

C. Cleaving a Cleavage Structure and Generating a Signal

A cleavage structure according to the invention can be cleaved by the methods described in the section above, entitled "FEN Nucleases".

D. Detection of Released Labeled Fragments

Detection or verification of the labeled fragments may be accomplished by a variety of methods well known in the art and may be dependent on the characteristics of the labeled moiety or moieties comprising a labeled cleavage structure.

In one embodiment of the invention, the reaction products, including the released labeled fragments, are subjected to size analysis. Methods for determining the size of a labeled fragment are known in the art and include, for example, gel electrophoresis, sedimentation in gradients, gel exclusion chromatography, mass spectroscopy, and homochromatography.

During or after amplification, separation of the released labeled fragments from, for example, a PCR mixture can be accomplished by, for example, contacting the PCR with a solid phase extractant (SPE). For example, materials having an ability to bind nucleic acids on the basis of size, charge, or interaction with the nucleic acid bases can be added to the PCR mixture, under conditions where labeled, uncleaved nucleic acids are bound and short, labeled fragments are not. Such SPE materials include ion exchange resins or beads, such as the commercially available binding particles Nensorb (DuPont Chemical Co.), Nucleogen (The Nest Group), PEI, BakerBond™ PEI, Amicon PAE 1,000, Selectacel™ PEI, Boronate SPE with a 3'-ribose probe, SPE containing sequences complementary to the 3'-end of the probe, and hydroxylapatite. In a specific embodiment, if a dual labeled oligonucleotide comprising a 3' biotin label separated from a 5' label by a nuclease susceptible cleavage site is employed as the signal means, the reaction mixture, for example a PCR amplified mixture can be contacted with materials containing a specific binding partner such as avidin or streptavidin, or an antibody or monoclonal antibody to biotin. Such materials can include beads and particles coated with specific binding partners and can also include magnetic particles.

Following the step in which a reaction mixture, for example a PCR mixture has been contacted with an SPE, the SPE material can be removed by filtration, sedimentation, or magnetic attraction, leaving the labeled fragments free of uncleaved labeled oligonucleotides and available for detection.

IV. Methods of Use

The invention provides for a method of generating a signal indicative of the presence of a target nucleic acid sequence in a sample comprising the steps of forming a labeled cleavage structure by incubating a target nucleic acid sequence with a nucleic acid polymerase, and cleaving the cleavage structure with a nuclease. The method of the invention can be used in a PCR based assay as described below.

A labeled cleavage structure comprising an upstream oligonucleotide primer (for example A, FIG. 3), a 5' end labeled downstream oligonucleotide probe (for example C in FIG. 3) and a target nucleic acid sequence (for example B in FIG. 3) is formed as described above in the section entitled "Cleavage Structure". Briefly, a cleavage structure is formed and cleaved in the presence of a target nucleic acid sequence, an upstream primer (for example A, FIG. 3), a labeled downstream probe (for example C, FIG. 3) amplification primers specific for the target nucleic acid sequence, a nucleic acid polymerase deficient in 5' to 3' exonuclease activity, a FEN nuclease and an appropriate buffer (for example 10× Pfu buffer, Stratagene, Catalog# 200536) in a PCR reaction with the following thermocycling parameters: 95° C. for 2 minutes and 40 cycles of 95° C. for 15 sec (denaturation step), 60° C. for 60 sec (annealing step)and 72° C. for 15 sec (extension step). During this reaction an upstream oligonucleotide (for example A, FIG. 3) is extended such that oligonucleotide A partially displaces the 5' labeled end of a downstream oligonucleotide that is annealed to a target nucleic acid sequence (for example oligonucleotide C, FIG. 3) and the resulting labeled structure is cleaved with a FEN nuclease according to the invention.

The methods of the invention can also be used in non-PCR based applications to detect a target nucleic acid sequence. In some embodiments, the may be immobilized on a solid support. Methods of immobilizing a nucleic acid sequence on a solid support are known in the art and are described in Ausubel FM et al. Current Protocols in Molecular Biology, John Wiley and Sons, Inc. and in protocols provided by the manufacturers, e.g. for membranes: Pall Corporation, Schleicher & Schuell, for magnetic beads: Dynal, for culture plates: Costar, Nalgenunc, and for other supports useful according to the invention, CPG, Inc. A solid support useful according to the invention includes but is not limited to silica based matrices, membrane based matrices and beads comprising surfaces including, but not limited to styrene, latex or silica based materials and other polymers. Magnetic beads are also useful according to the invention. Solid supports can be obtained from the above manufacturers and other known manufacturers.

The invention also provides for a non-PCR based assay for detecting a target nucleic acid sequence in solution. The method of the invention can be used to detect naturally occurring target nucleic acid sequences in solution including but not limited to RNA and DNA that is isolated and purified from cells, tissues, single cell organisms, bacteria or viruses. The method of the invention can also be used to detect synthetic targets in solution, including but not limited to RNA or DNA oligonucleotides, and peptide nucleic acids (PNAs). Non-PCR assays include but are not limited to detection assays involving isothermal linear or exponential amplification, where the amount of nucleic acid synthesized by the 3'-5' synthetic activity increases linearly or exponentially, and a FEN nuclease is used to cleave the displaced strand during synthesis. One such example utilizes rolling circle amplification.

Detection of a nucleic acid target sequence that is either immobilized or in solution can be performed by incubating an immobilized nucleic acid target sequence or a target nucleic acid sequence in solution with an upstream oligonucleotide primer that is complementary to the target nucleic acid sequence (for example A, FIG. 3) and a downstream oligonucleotide probe that is complementary to the target nucleic acid sequence (for example C, FIG. 3), a FEN nuclease and a nucleic acid polymerase lacking 5' to 3' exonuclease activity. The downstream probe is either end labeled at the 5' or 3' end, or is labeled internally. Detection of a released labeled fragment involves isotopic, enzymatic, or colorimetric methods appropriate for the specific label that has been incorporated into the probe. Labels useful according to the invention and methods for the detection of labels useful according to the invention are described in the section entitled "Cleavage Structure". Alternatively, the downstream probe comprises a pair of interactive signal generating labeled moieties (for example a dye and a quencher) that are positioned such that when the probe is intact, the generation of a detectable signal is quenched, and wherein the pair of interactive signal generating moieties are separated by a FEN nuclease cleavage site. Upon cleavage by a FEN nuclease, the two signal generating moieties are separated from each other and a detectable signal is produced. Nucleic acid polymerases that are useful for detecting an immobilized nucleic acid target sequence or a nucleic acid target sequence in solution according to the method of the invention include mesophilic, thermophilic or hyperthermophilic DNA polymerases lacking 5' to 3' exonucleolytic activity (described in the section entitled, "Nucleic Acid Polymerases)".

According to this non-PCR based method, the amount of a target nucleic acid sequence that can be detected is preferably about 1 pg to 1 µg, more preferably about 1 pg to 10 ng and most preferably about 1 pg to 10 pg. Alternatively, this non-PCR based method can measure or detect preferably about 1 molecule to $10^{20}$ molecules, more preferably about 100 molecules to $10^{17}$ molecules and most preferably about 1000 molecules to $10^{14}$ molecules.

The invention also provides a method for detecting a target nucleic acid using a 3' blocked upstream oligonucleotide. Such embodiments are described throughout the specification, specifically in Examples 7-13.

In further embodiment, the invention contemplates cleavage of a 5' non-complementary flap by Fen nuclease in the presence of a 3'-blocked, upstream oligonucleotide that does not overlap with the region where the 5'-flapped probe (e.g., a key probe, as described in co-pending patent application U.S. Ser. No. 60/688,798) is complementary to the target sequence. The data in FIG. 20 demonstrates that efficient cleavage of a 5' flap is produced in the absence of such overlap, where the 3' end of the probe is blocked.

It is preferred that the upstream primer having a 3' blocked end is complementary to the target such that there is a distance between the 3' end of the blocked primer and the 5' end of the probe of no nucleotides or a "nick". In other embodiments, the distance between the 3' end of the blocked primer and the 5' end of the probe is 1 nucleotide, 2 nucleotides, 5, 10 or 15 nucleotides or more.

According to this aspect of the invention, a non-overlapping, upstream oligonucleotide that is unable to be extended by a polymerase (a 3'-blocked oligonucleotide such as a 3' phosphate blocked oligonucleotide) is capable of facilitating cleavage of a 5' flap by a nuclease, e.g., FEN.

In one embodiment, the cleavage reaction is preferably carried out at a temperature above the melting temperature of the PCR primers, such that 5'-flapped probe cleavage occurs during the cooling phase of the PCR reaction prior to annealing of the PCR primers. Thus, as the PCR reaction is cooled from 95 degrees centigrade, annealing of the 5'-flapped probe and the blocked oligonucleotide to the target preferably occurs at a higher temperature than the temperature at which the PCR primers anneal to the target. The cleavage enzyme (FEN) is thus able to cleave the probe prior to extension of the PCR primers by the polymerase. After cleavage, the reaction may be allowed to cool further, allowing the PCR primers to anneal and be extended by the polymerase.

The invention also provides for a method of detecting a target nucleic acid sequence in a sample wherein a cleavage structure is formed as described in the section entitled, "Cleavage Structure", and the target nucleic acid sequence is amplified by a non-PCR based method including but not limited to an isothermal method, for example rolling circle, Self-sustained Sequence Replication Amplification (3SR), Transcription based amplification system (TAS), and Strand Displacement Amplification (SDA) and a non-isothermal method, for example Ligation chain reaction (LCR). A FEN nuclease useful for non-PCR amplification methods will be active at a temperature range that is appropriate for the particular amplification method that is employed.

In the amplification protocols described below, samples which need to be prepared in order to quantify the target include: samples, no-template controls, and reactions for preparation of a standard curve (containing dilutions over the range of six orders of magnitude of a solution with a defined quantity of target).

Strand Displacement Amplification (SDA) is based on the ability of a restriction enzyme to nick the unmodified strand of a hemiphosphorothioate form of its recognition site. The appropriate DNA polymerase will initiate replication at this nick and displace the downstream non-template strand (Walker, 1992, *Proc. Natl. Acad. Sci. USA*, 89: 392, and PCR Methods and Applications 3: 1-6, 1993). The polymerases (Bca and Bst) which are used according to the method of SDA can also be used in FEN directed cleavage according to the invention. According to the method of the invention, a molecular beacon is replaced by a FEN nuclease active at 420 C and a cleavable probe comprising a cleavage structure according to the invention.

A molecular beacon (Mb) is a fluorogenic probe which forms a stem-loop structure is solution. Typically: 5'-fluorescent dye (e.g. FAM), attached to the 5'-stem region (5-7 nt), the loop region (complementary to the target, 20 to 30 nt), the 3'-stem region (complementary to the 5'-stem region), and the quencher (e.g. DABCYL). If no target is present, the MB forms its stem, which brings dye and quencher into close proximity, and therefore no fluorescence is emitted. When an MB binds to its target, the stem is opened, dye is spatially separated from the quencher, and therefore the probe emits fluorescence (Tyagi S and Kramer F R, Nature Biotechnology 14: 303-308 (1996) and U.S. Pat. No. 5,925,517).

Strand Displacement Amplification (SDA) is essentially performed as described by Spargo et al., Molecular and Cellular Probes 10: 247-256 (1996). The enzymes used include restriction endonuclease BsoBI (New England Biolabs), DNA polymerase 5'-exo-Bca (PanVera Corporation). The target is an insertion-like element (IS6110) found in the Mycobacterium tuberculosis (Mtb) genome. The primers used are B1: cgatcgagcaagcca (SEQ ID NO: 4), B2: cgagccgctcgctg (SEQ ID NO: 5), S1: accgcatcgaatgcat-gtctcgggtaaggcgtactcgacc (SEQ ID NO: 6) and S2: cgattc-cgctccagacttctcgggtgtactgagatcccct (SEQ ID NO: 7). The Mycobacterium tuberculosis genomic DNA is serially diluted in human placental DNA. SDA is performed in 50 ul samples containing 0 to 1000 Mtb genome equivalents, 500 ng human placental DNA, 160 units BsoB1, 8 units of 5'-exo-Bca, 1.4 mM each dCTPalphaS, TTP, dGTP, dATP, 35 mM K$_2$PO$_4$, pH 7.6 0.1 mg/ml acetylated bovine serum albumin (BSA), 3 mM Tris-HCl, 10 mM MgCl$_2$, 11 mM NaCl, 0.3 mM DTT, 4 mM KCl, 4% glycerol, 0.008 mM EDTA, 500 nM primers S1 and S2 and 50 nM primers B1 and B2 (KCl, glycerol and EDTA are contributed by the BsoB1 storage solution). The samples (35 μl) were heated in a boiling water bath for 3 minutes before the addition of BsoB1 and 5'-exo Bca (10.7 units/μl BsoB1 and 0.53 units/μl 5'-exo Bca in 15 μl of New England Biolabs Buffer 2 (20 mM Tris-HCl pH 7.9, 10 mM MgCl$_2$, 50 mM NaCl, 1 mM DTT). Incubation is at 60° C. for 15 minutes, followed by 5 minutes in a boiling water bath.

Five μl of each sample in duplicate are removed for detection. Each reaction contains 1 × Cloned Pfu buffer, 3.0 mM MgCl$_2$, 200 uM of each dNTP, 5 units exo-Pfu, 23 ng Pfu FEN-1, 1 ng PEF, 300 nM each upstream primer: aaggcgtactcgacctgaaa (SEQ ID NO: 8) and fluorogenic probe (for example FAM-DABCYL): accatacggataggg-gatctc (SEQ ID NO: 9). The reactions are subjected to one cycle in a thermal cycler: 2 minutes at 95° C., 1 minute at 55° C., 1 minute at 72° C. The fluorescence is then determined in a fluorescence plate reader, such as Stratagene's FluorTracker or PE Biosystems' 7700 Sequence Detection System in Plate-Read Mode.

According to the method of nucleic acid sequence-based amplification (NASBA), molecular beacons are used for quantification of the NASBA RNA amplicon in real-time analysis (Leone, et al., 1998, *Nucleic Acids Res.* 26: 2150). According to the method of the invention, NASBA can be carried out wherein the molecular beacon probe is replaced by a FEN nuclease cleavable probe comprising a cleavage structure according to the invention and a FEN nuclease active at 41° C.

NASBA amplification is performed essentially as described by Leone G, et al., Nucleic Acids Res. 26: 2150-2155 (1998). Genomic RNA from the potato leafroll virus (PLRV) is amplified using the PD415 or PD416 (antisense) and the PD417 (sense) primers, which are described in detail in Leone G et al., J. Virol. Methods 66: 19-27 (1997). Each NASBA reaction contains a premix of 6 μl of sterile water, 4 μl of 5× NASBA buffer (5× NASBA buffer is 200 mM Tris-HCl, pH 8.5, 60 mM MgCl$_2$, 350 mM KCl, 2.5 mM DTT, 5 mM each of dNTP, 10 mM each of ATP, UTP and CTP, 7.5 mM GTP and 2.5 mM ITP), 4 μl of 5× primer mix (75% DMSO and 1 μM each of antisense and sense primers). The premix is divided into 14 μl aliquots, to which 1 μl of PLRV target is added. After incubation for 5 minutes at 65° C. and cooling to 41° C. for 5 minutes, 5 μl of enzyme mix is added (per reaction 375 mM sorbitol, 2.1 μg BSA, 0.08 units of RNase H (Pharmacia), 32 units of T7 RNA polymerase (Pharmacia) and 6.4 units of AMV-RT (Seigakaku)). Amplification is for 90 minutes at 41° C.

Five μl of each sample in duplicate are removed for detection. Each reaction contains 1× Cloned Pfu buffer, 3.0 mM MgCl$_2$, 200 uM of each dNTP, 5 units exo-Pfu, 23 ng Pfu FEN-1, 1 ng PEF, 300 nM each upstream primer PD415 or PD416 and the fluorogenic probe (for example FAM-DABCYL): gcaaagtatcatccctccag (SEQ ID NO: 10). The reactions are subjected to one cycle in a thermal cycler: 2 minutes at 95° C., 1 minute at 55° C., 1 minute at 72° C. The fluorescence in then determined in a fluorescence plate reader, such as Stratagene's FluorTracker or PE Biosystems' 7700 Sequence Detection System in Plate-Read Mode.

Generally, according to these methods wherein amplification occurs by a non-PCR based method, amplification may be carried out in the presence of a FEN nuclease, and amplification and cleavage by the FEN nuclease occur simultaneously. Detection of released labeled fragments is performed as described in the section entitled "Cleavage Structure" and may occur concurrently with (real time) or after (end-point) the amplification and cleavage process have been completed.

Endpoint assays can be used to quantify amplified target produced by non-PCR based methods wherein the amplification step is carried out in the presence of a FEN nuclease (described above).

Endpoint assays include, but are not limited to the following.

A. Ligation chain reaction (LCR), as described in Landegren, et al., 1988, *Science,* 241: 1077 and Barany, PCR Methods and Applications 1: 5-16 (1991). An LCR product useful according to the invention will be long enough such that the upstream primer and the labeled downstream probe are separated by a gap larger than 8 nucleotides to allow for efficient cleavage by a FEN nuclease.

B. Self-sustained sequence replication amplification (3SR) Fahy, et al. PCR Methods and Applications 1: 25-33 (1991). Self-Sustained Sequence Replication Amplification (3SR) is a technique which is similar to NASBA. Ehricht R, et al., Nucleic Acids Res. 25: 4697-4699 (1997) have evolved the 3SR procedure to a cooperatively coupled in vitro amplification system (CATCH). Thus, in CATCH, a molecular beacon probe is used for real-time analysis of an RNA amplicon. The synthetic target amplified has the sequence: cctctgcagactactattacataatac-gactcactatagggatctgcacgtatt-agcctatagtgagtcgtattaataggaaacaccaaagatga tatttcgtcacag-caagaattcagg (SEQ ID NO: 11). The 3SR reactions contain 40 mM Tris-HCl pH 8.0, 5 mM KCl, 30 mM MgCl$_2$, 1 mM of each dNTP, 1 nM of the double stranded target, 2 μM P1: cctctgcagactactattac (SEQ ID NO: 12) and P2:cctgaattct-tgctgtgacg (SEQ ID NO: 13), 5 mM DTT, 2 mM spermidine, 6 units/ul His tagged HIV-1 reverse transcriptase, 3 units/ul T7-RNA polymerase and 0.16 units/ul *Escherichia coli* RNase H. The 100 ul reactions are incubated for 30 minutes at 42° C.

Five μl of each sample in duplicate are removed for detection. Each reaction contains 1× Cloned Pfu buffer, 3.0 mM MgCl$_2$, 200 uM of each dNTP, 5 units exo-Pfu, 23 ng Pfu FEN-1, 1 ng PEF, 300 nM each upstream primer P1 and fluorogenic probe (for example FAM-DABCYL): taggaaa-caccaaagatgatattt (SEQ ID NO: 14). The reactions are subjected to one cycle in a thermal cycler: 2 minutes at 95° C., 1 minute at 55° C., 1 minute at 72° C. The fluorescence in then determined in a fluorescence plate reader, such as Stratagene's FluorTracker or PE Biosystems' 7700 Sequence Detection System in Plate-Read Mode.

C. Rolling circle amplification is described in U.S. Pat. No. 5,854,033 and the related Ramification-Extension Amplification Method (RAM) (U.S. Pat. No. 5,942,391). Rolling circle amplification adapted to the invention is described in Example 3 below.

Real-time assays can also be used to quantify amplified target produced by non-PCR based methods wherein the amplification step is carried out in the presence of a FEN nuclease (described above). The method of rolling circle amplification (U.S. Pat. No. 5,854,033) is adapted to include secondary primers for amplification and detection, in conjunction with a FEN nuclease and a cleavable probe comprising a cleavage structure according to the invention and is carried out at temperatures between 50-60° C.

The cleavage pattern of a FEN nuclease can be altered by the presence of a single mismatched base located anywhere between 1 and 15 nucleotides from the 5' end of the primer wherein the DNA primer is otherwise fully annealed. Typically, on a fully annealed substrate, a FEN nuclease will exonucleolytically cleave the 5' most nucleotide. However, a single nucleotide mismatch up to 15 nucleotides in from the 5' end promotes endonucleolytic cleavages. This constitutes a 5' proofreading process in which the mismatch promotes the nuclease action that leads to its removal. Thus, the mechanism of FEN nuclease cleavage is shifted from predominantly exonucleolytic cleavage to predominantly endonucleolytic cleavage simply by the presence of a single mismatched base pair. Presumably this occurs because a mismatch allows a short flap to be created (Rumbaugh et al., 1999, J. Biol. Chem., 274:14602).

The method of the invention can be used to generate a signal indicative of the presence of a sequence variation in a target nucleic acid sequence, wherein a labeled cleavage structure comprising a fully annealed DNA primer is formed by incubating a target nucleic acid sequence with a nucleic acid polymerase (as described in the section entitled, "Cleavage Structure") and cleaving the labeled cleavage structure with a FEN nuclease wherein the release of labeled fragments comprising endonucleolytic cleavage products is indicative of the presence of a sequence variation. Released labeled fragments are detected as described in the section entitled, "Cleavage Structure".

V. Samples

The invention provides for a method of detecting or measuring a target nucleic acid sequence in a sample, as defined herein. As used herein, "sample" refers to any substance containing or presumed to contain a nucleic acid of interest (a target nucleic acid sequence) or which is itself a target nucleic acid sequence, containing or presumed to contain a target nucleic acid sequence of interest. The term "sample" thus includes a sample of target nucleic acid sequence (genomic DNA, cDNA or RNA), cell, organism, tissue, fluid or substance including but not limited to, for example, plasma, serum, spinal fluid, lymph fluid, synovial fluid, urine, tears, stool, external secretions of the skin, respiratory, intestinal and genitourinary tracts, saliva, blood cells, tumors, organs, tissue, samples of in vitro cell culture constituents, natural isolates (such as drinking water, seawater, solid materials,) microbial specimens, and objects or specimens that have been "marked" with nucleic acid tracer molecules.

EXAMPLES

The invention is illustrated by the following nonlimiting examples wherein the following materials and methods are employed. The entire disclosure of each of the literature references cited hereinafter are incorporated by reference herein.

Example 1

A target nucleic acid sequence can be detected and/or measured by the following method. A labeled cleavage structure is formed prior to the addition of a FEN nuclease by heating at 95° C. for 5 minutes and then cooling to approximately 50-60° C. (a) a sample containing a target nucleic acid sequence (B in FIG. 3) with (b) an upstream oligonucleotide that specifically hybridizes to the target nucleic acid sequence, (A, in FIG. 3), and (c) a downstream, 5' end labeled oligonucleotide (C in FIG. 3) that specifically hybridizes to a region of the target nucleic acid sequence that is downstream of the hybridizing region of oligonucleotide A. A polymerase that lacks a 5' to 3' exonuclease activity but that possesses a 3' to 5' DNA synthetic activity, such as the enzyme a)Yaq exo-, (prepared by mutagenesis using the Stratagene QuikChange Site-Directed Mutagenesis kit, catalog number #200518, to modify Taq polymerase (Tabor and Richardson, 1985, Proc. Natl. Acad. Sci. USA, 82:1074)), a mutant form of Taq polymerase that lacks 5' to 3' exonuclease activity, b) Pfu, or c) a mutant form of Pfu polymerase that lacks 3' to 5' exonuclease activity (exo-Pfu) is added and incubated under conditions that permit the polymerase to extend oligonucleotide A such that it partially displaces the 5' end of oligonucleotide C (for example 72° C. in 1× Pfu buffer (Stratagene) for 5 minutes to 1 hour. The displaced region of oligonucleotide C forms a 5' flap that is cleaved upon the addition of a FEN nuclease.

A mutant form of Taq polymerase that lacks a 5' to 3' exonuclease activity but that possesses a 3' to 5' DNA synthetic activity comprises the following mutation: D144S/F667Y Taq wherein D144S eliminates 5' to 3' exonuclease activity and F667Y improves ddNTP incorporation.

Exo-mutants of PolI polymerase can be prepared according to the method of Xu et al., 1997, J. Mol. Biol., 268: 284.

A labeled cleavage structure according to the invention is cleaved with a preparation of PfuFEN-1 (i.e. cloned Pyrococcus furiosus FEN-1 that is prepared as described below in Example 2). Cleavage is carried out by adding 2 μl of PfuFEN-1 to a 7 μl reaction mixture containing the following:

| | |
|---|---|
| 3 μl | cleavage structure (10 ng-10 μg) |
| 0.7 μl | 10x FEN nuclease buffer (10X FEN nuclease buffer contains 500 mM Tris-HCl pH 8.0, 100 mM MgCl$_2$) |
| 2.00 μl | PfuFEN-1 enzyme or H$_2$O |
| 1.3 μl | H$_2$O |
| 7.00 μl | total volume |

Samples are incubated for one hour at 50° C. in a Robocyler 96 hot top thermal cycler. Following the addition of 2 μl of Sequencing Stop dye solution (included in the Stratagene Cyclist DNA sequencing kit, catalog #200326, and described in example 3), samples are heated at 99° C. for five minutes. Samples are loaded on an eleven inch long, hand-poured, 20% acrylamide/bis acrylamide, 7M urea gel. The gel is run at 20 watts until the bromophenol blue has migrated approximately ⅔ the total distance. The gel is removed from the glass plates and soaked for 10 minutes in fix solution (15% methanol, 5% acetic acid) and then for 10 minutes in water. The gel is placed on Whatmann 3 mm paper, covered with plastic wrap and dried for 2 hours in a heated vacuum gel dryer (~800 C). The gel is exposed overnight to X-ray film to detect the presence of a signal that is indicative of the presence of a target nucleic acid sequence.

Example 2

Cloning Pfu FEN-1

A thermostable FEN nuclease enzyme useful according to the invention can be prepared according to the following method.

The thermostable FEN nuclease gene can be isolated from genomic DNA derived from P. furiosus (ATCC#43587)

according to methods of PCR cloning well known in the art. The cloned PfuFEN-1 can be overexpressed in bacterial cells according to methods well known in the art and described below.

The following pCAL-n-EK cloning oligonucleotides were synthesized and purified:

a.
5'GACGACGACAAGATGGGTGTCCCAATTGGTGAGATTATACCAAGAAAA G 3' (SEQ ID NO:15)

and b.
5'GGAACAAGACCCGTTTATCTCTTGAACCAACTTTCAAGGGTTGATTGT TTTCCACT 3' (SEQ ID NO:16).

The Affinity® Protein Expression and Purification System was obtained from Stratagene and used according to the manufacturer's protocols.

Amplification

The insert DNA was prepared by PCR amplification with gene-specific primers (oligonucleotides a and b, described above) that include 12 and 13-nucleotide sequences at the 5' ends that are complementary to the pCAL-n-EK vector single-stranded tails, thus allowing for directional cloning. The FEN-1 sequence was amplified from genomic DNA derived from *P. furiosus* by preparing amplification reactions (five independent 100 μl reactions) containing:

| | |
|---|---|
| 50 μl | 10x cPfu Buffer (Stratagene) |
| 7.5 μl | Pfu Genomic DNA (approx. 100 ng/μl) |
| 7.5 μl | PfuTurbo (2.5 u/μl), (Stratagene, Catalog # 600250) |
| 15 μl | mixed primer pair (100 ng/μl each) (oligonucleotides a and b, described above) |
| 4 μl | 100 mM dNTP |
| 416 | 1 H$_2$O |
| 500 μl | total | and carrying out the amplification under the following conditions using a Stratagene Robocycler 96 hot top thermal cycler:

| | | | |
|---|---|---|---|
| Window 1 | 95° C. | 1 minute | 1 cycle |
| Window 2 | 95° C. | 1 minute | |
| | 50° C. | 1 minute | 30 cycles |
| | 72° C. | 3 minutes | |

The PCR products from each of the five reactions were combined into one tube, purified using StrataPrep PCR and eluted in 50 μl 1 mM Tris-HCl pH 8.6. The FEN-1 PCR product was analyzed on a gel and was determined to be approximately 1000 bp.

The PCR product comprising the fen-1 gene was cloned into the pCALnEK LIC vector (Stratagene) by creating ligation independent cloning termini (LIC), annealing the PCR product comprising the fen-1 gene to the pCALnEK LIC vector (Stratagene), and transforming cells with the annealing mixture according to the following method. Briefly, following PCR amplification, the PCR product is purified and treated with Pfu DNA polymerase in the presence of dATP (according to the manual included with the Affinity® Protein Expression and Purification System, Stratagene, catalog #200326). In the absence of dTTP, dGTP and dCTP, the 3' to 5'-exonuclease activity of Pfu DNA polymerase removes at least 12 and 13 nucleotides at the respective 3' ends of the PCR product. This activity continues until the first adenine is encountered, producing a DNA fragment with 5'-extended single-stranded tails that are complementary to the single-stranded tails of the pCAL-n-EK vector.

Creating LIC termini

LIC termini were created by preparing the following mixture:

45 μl purified PCR product (~0.5 μg/μl)
2.5 μl 10 mM dATP
5 μl 10× cPfu buffer
1 μl cPfu (2.5 u/μl)
0.5 μl H$_2$O cPfu and cPfu buffer can be obtained from Stratagene (cPfu, Stratagene Catalog #600153 and cPfu buffer, Stratagene Catalog #200532).

Samples were incubated at 72° C. for 20 minutes and products were cooled to room temperature. To each sample was added 40 ng prepared pCALnEK LIC vector (the prepared vector is available commercially from Stratagene in the Affinity LIC Cloning and Protein Purification Kit (214405)). The vector and insert DNA are combined, allowed to anneal at room temperature and transformed into highly competent bacterial host cells (Wyborski et al., 1997, *Strategies*, 10:1).

Preparing Cells for Production of FEN

Two liters of LB-AMP was inoculated with 20ml of an overnight culture of a FEN-1 clone (clone 3). Growth was allowed to proceed for approximately 11 hours at which point cells had reached an OD$_{600}$=0.974. Cells were induced overnight (about 12 hours) with 1 mM IPTG. Cells were collected by centrifugation and the resulting cell paste was stored at −20° C.

Purification of Tagged FEN-1

Cells were resuspended in 20 ml of Calcium binding buffer

CaCl$_2$ binding Buffer
50 mM Tris-HCl (pH 8.0)
150 mM NaCl
1.0 mM MgOAc
2 mM CaCl$_2$ The samples were sonicated with a Branson Sonicator using a microtip. The output setting was 5 and the duty cycle was 90%. Samples were sonicated three times and allowed to rest on ice during the intervals. The sonicate was centrifuged at 26,890×g. Cleared supernatants were mixed with 1 ml of washed (in CaCl$_2$ binding buffer) calmodulin agarose (CAM agarose) in a 50ml conical tube and incubated on a slowly rotating wheel in a cold room (4° C.) for 5 hours. The CAM agarose was collected by light centrifugation (5000 rpm in a table top centrifuge).

Following removal of the supernatant, the CAM agarose was washed with 50 ml CaCl$_2$ binding buffer and transferred to a disposable drip column. The original container and pipet were rinsed thoroughly to remove residual agarose. The column was rinsed with approximately 200 ml of CaCl$_2$ binding buffer.

Elution was carried out with 10 ml of 50 mM NaCl elution buffer (50 mM NaCl, 50 mM Tris-HCl pH 8.0, 2 mM EGTA). 0.5 ml fractions were collected. A second elution step was carried out with 1M NaCl elution buffer wherein 0.5 ml fractions were collected.

Evaluation of purified tagged FEN-1

Figure 4:
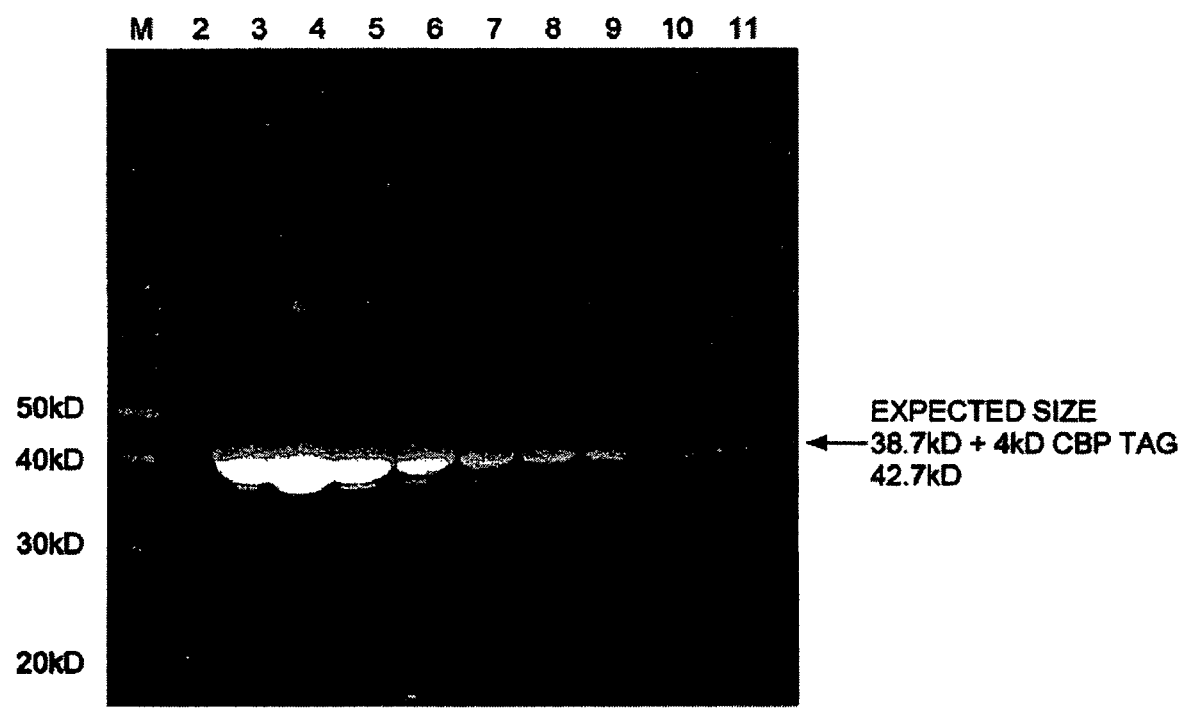
FIG. 4 is a Sypro Orange stained polyacrylamide gel demonstrating CBP-tagged Pfu FEN-1 protein.

Fractions containing CBP-tagged Pfu FEN-1 eluted in 1M NaCl were boiled in SDS and analyzed by SDS-PAGE on a 4-20% gel stained with Sypro Orange (FIG. 4).

The protein concentration of uncleaved FEN-1 was determined to be approximately 150 ng/microliter (below).

Enterokinase Protease (EK) Cleavage of the Purified FEN-1

Fractions 3-9 were dialyzed in 50 mM NaCl, 50 mM Tris-HCl pH 8.0 and 2 mM $CaCl_2$ overnight at 4° C.

An opaque, very fine precipitate appeared in the dialyzed FEN-1. When the sample was diluted 1/20 the precipitate was removed. When the sample was diluted 1/3 insoluble material was still detectable. The 1/3 diluted material was heated at 37° C. for 2 minutes and mixed with Tween 20 to a final concentration of 0.1%. Upon the addition of the Tween 20, there was an almost immediate formation of "strings" and much coarser solids in the solution which could not be reversed even after the solution was adjusted to 1M NaCl.

EK cleavage was carried out using as a substrate the sample that was diluted 1/20 as well as with a dilute sample prepared by rinsing the dialysis bag with 1× EK buffer.

EK cleavage was carried out by the addition of 1 µl EK (1 u/µl) overnight at room temperature (about 16 hours).

100 µl of STI agarose combined with 100 µl of CAM agarose were rinsed twice with 10 ml of 1× STI buffer (50 mM Tris-HCl pH 8.0, 200 mM NaCl, 2 mM $CaCl_2$, 0.1% Tween 20). NaCl was added to the two EK samples to bring the final concentration to 200 mM NaCl. The two samples were combined and added to the rinsed agarose. The samples were rotated slowly on a wheel at 4° C. for three hours and separated by light centrifugation in a table top centrifuge (as described). The supernatant was removed and the resin was rinsed twice with 500 µl 1× STI. The two rinses were combined and saved separately from the original supernatant. Samples were analyzed by SDS-PAGE on a 4-20% gel.

The concentration of digested product was approximately 23 ng/µl as determined by comparison to a Pfu standard at a concentration of approximately 50 ng/ml.

Example 3

Fen Nuclease Activity

The endonuclease activity of a FEN nuclease and the cleavage structure requirements of a FEN nuclease prepared as described in Example 2 can be determined according to the methods described either in the section entitled "FEN nucleases" or below.

Briefly, three templates (FIG. 2) are used to evaluate the activity of a FEN nuclease according to the invention. Template 1 is a $5'^{33}p$ labeled oligonucleotide (Heltest4) with the following sequence:

```
                                        (SEQ ID NO:1)
5'AAAATAAATAAAAAAATACTGTTGGGAAGGGCGATCGGTGCG3'.
```

The underlined section of Heltest4 represents the region complementary to M13mp18+. The cleavage product is an 18 nucleotide fragment with the sequence AAAATAAATAAAAAAAT (SEQ ID NO: 2). Heltest4 binds to M13 to produce a complementary double stranded domain as well as a non-complementary 5' overhang. This duplex forms template 2 (FIG. 2). Template 3 (FIG. 2) has an additional primer (FENAS) bound to M13 which is directly adjacent to Heltest 4. The sequence of FENAS is: 5' CCATTCGCCATTCAGGCTGCGCA 3' (SEQ ID NO: 3).

In the presence of template 3, a FEN nuclease binds the free 5' terminus of Heltest4, migrates to the junction and cleaves Heltest4 to produce an 18 nucleotide fragment. The resulting cleavage products are separated on a 6% acrylamide, 7M urea sequencing gel.

Templates are prepared as described below:

|  | Template 1 | Template 2 | Template 3 |
|---|---|---|---|
| Heltest4 | 14 µl | 14 µl | 14 µl |
| M13 | ** | 14 µl | 14 µl |
| FENAS | ** | ** | 14 µl |
| $H_2O$ | 28 µl | 14 µl | ** |
| 10x Pfu Buff. | 4.6 µl | 4.6 µl | 4.6 µl |

Pfu buffer can be obtained from Stratagene (Catalog #200536).

The template mixture is heated at 95° C. for five minutes, cooled to room temperature for 45 minutes and stored at 4° C. overnight.

The enzyme samples are as follows:

| | |
|---|---|
| A. | $H_2O$ (control) |
| B. | 2 µl undiluted uncleaved FEN-1 (~445 ng/µl) |
| C. | 2 µl 1/10 dilution of uncleaved FEN-1 (~44.5 ng/µl) |
| D. | 2 µl enterokinase protease (EK) cleaved FEN-1 (~23 ng/µl) |

The four reaction mixtures are mixed with the three templates as follows:

| | |
|---|---|
| 3 µl | template 1, template 2 or template 3 |
| 0.7 µl | 10x cloned Pfu buffer |
| 0.6 µl | 100 mM $MgCl_2$ |
| 2.00 µl | FEN-1 or $H_2O$ |
| 0.7 µl | $H_2O$ |
| 7.00 µl | total volume |

The reactions are allowed to proceed for 30 minutes at 50° C. and stopped by the addition of 2 µl formamide "Sequencing Stop" solution to each sample. Samples are heated at 95° C. for five minutes and loaded on a 6% acrylamide 7M urea CastAway gel (Stratagene).

Alternatively, FEN nuclease activity can be analyzed in the following buffer wherein a one hour incubation time is utilized.

10× FEN Nuclease Buffer
500 mM Tris-HCl pH 8.0
100 mM $MgCl_2$

The reaction mixture is as follows:

| | |
|---|---|
| 3 µl | template 1, template 2 or template 3 |
| 0.7 µl | 10x FEN nuclease buffer |
| 2.00 µl | FEN-1 or $H_2O$ (A-D, above) |
| 1.3 µl | $H_2O$ |
| 7.00 µl | total volume |

Samples are incubated for one hour at 50° C. in the Robocyler 96 hot top thermal cycler. Following the addition of 2 µl of Sequencing Stop (95% formamide, 20 mM EDTA, 0.05% bromophenol blue, 0.05% xylene cyanol, available from Stratagene) dye solution, samples are heated at 99° C. for five minutes. Samples are loaded on an eleven inch long, hand-poured, 20% acrylamide/bis acrylamide, 7M urea gel. The gel is run at 20 watts until the bromophenol blue has migrated approximately ⅔ the total distance. The gel is removed from the glass plates and soaked for 10 minutes in fix solution (15% methanol, 5% acetic acid) and then for 10 minutes in water. The gel is placed on Whatmann 3 mm paper, covered with plastic wrap and dried for 2 hours in a heated vacuum gel dryer (~800C). The gel is exposed overnight to X-ray film.

Figure 5:
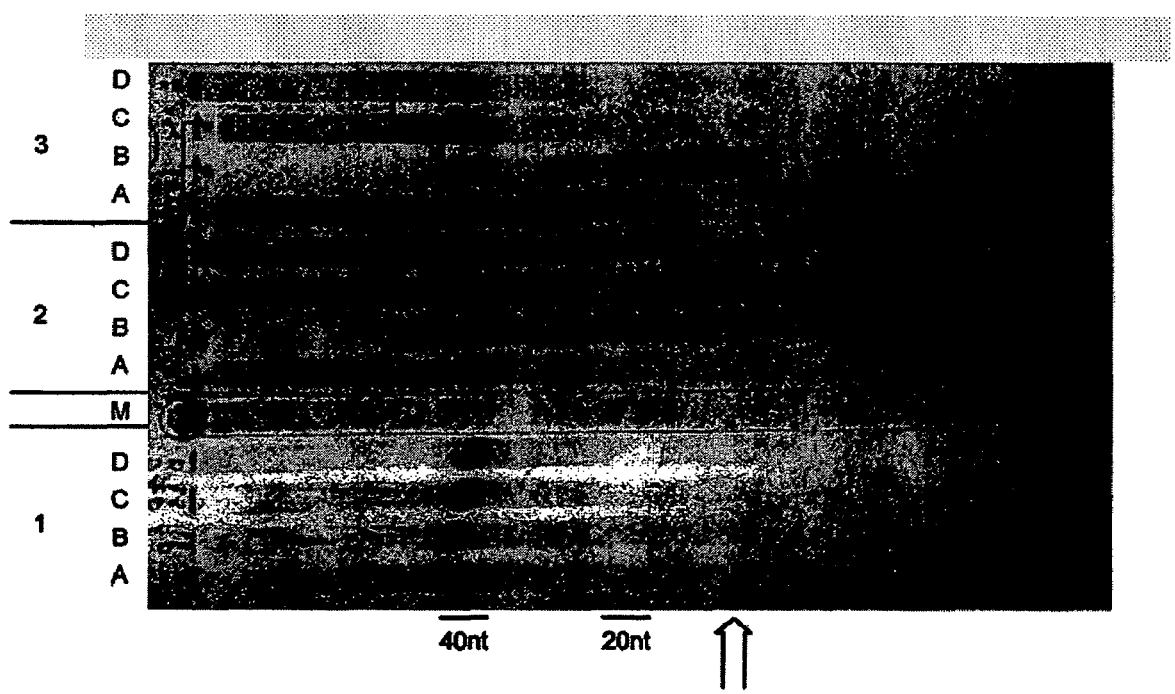
FIG. 5 is an autoradiograph of a FEN-1 nuclease assay.

An autoradiograph of a FEN-1 nuclease assay wherein templates 1, 2 and 3 (prepared as described above) are cleaved by the addition of:

| A. | $H_2O$ |
| B. | 2 µl of CBP-tagged Pfu FEN-1 |
| C. | 2 µl of CBP-tagged Pfu FEN-1 diluted (1:10) |
| D. | 2 µl of EK cleaved Pfu FEN-1 | is presented in FIG. 5.

The lanes are as follows. Lanes 1A, 1B, 1C and 1D represent template 1 cleaved with $H_2O$, undiluted CBP-tagged Pfu FEN-1, a 1:10 dilution of CBP-tagged Pfu FEN-1 and EK cleaved Pfu FEN-1, respectively. Lanes 2A, 2B, 2C and 2D represent template 2 cleaved with $H_2O$, undiluted CBP-tagged Pfu FEN-1, a 1:10 dilution of CBP-tagged Pfu FEN-1 and EK cleaved Pfu FEN-1, respectively. Lanes 3A, 3B, 3C and 3D represent template 3 cleaved with $H_2O$, undiluted CBP-tagged Pfu FEN-1, a 1:10 dilution of CBP-tagged Pfu FEN-1 and EK cleaved Pfu FEN-1, respectively.

Tagged Pfu FEN-1 contains the N-terminal CBP affinity purification tag. Any differences in activity between tagged and untagged versions of FEN-1 are due to differences in protein concentration (concentrations of enzyme samples are provided above) since the amounts of tagged versus untagged FEN-1 are not equivalent. Both tagged and untagged Pfu FEN-1 demonstrate cleavage activity.

FIG. 5 demonstrates the background level of cleavage in the absence of FEN-1 (lanes 1A, 2A and 3A). Further, this Figure demonstrates that tagged Pfu FEN-1 cleaves more of template 2 as compared to template 1. In particular, the greatest amount of template 2 is cleaved in the presence of undiluted, tagged Pfu FEN-1 (lane 2B). Analysis of template 3 demonstrates that the greatest amount of template 3 is cleaved by undiluted, tagged Pfu FEN-1 and the least amount of template 3 is cleaved by diluted tagged FEN-1. Labeled probe migrates as a 40-43 nucleotide band. FEN-1 preferentially cleaves template 3 (which comprises an upstream primer) as compared to template 2. The cleavage product bands are the major bands migrating at 16-20 nucleotides. Heterogeneity in the labeled cleavage products is the result of heterogeneity in the labeled substrate, which was not gel-purified prior to use.

Example 4

PCR Amplification and Detection of β-actin in the Presence of a FEN-1 Nuclease and a Taq Polymerase Deficient in 5' to 3' Exonuclease Activity A PCR assay is used to detect a target nucleic acid sequence. According to the method of this assay, a PCR reaction is carried out in the presence of a Taq polymerase deficient in 5' to 3' exonuclease activity (for example Yaq exo-), and a thermostable FEN-1 nuclease (e.g. Pfu FEN-1, prepared as described in Example 2). Detection of the release of fluorescently labeled fragments indicates the presence of the target nucleic acid sequence.

Duplicate PCR reactions containing 1× Sentinel Molecular beacon core buffer, 3.5 mM $MgCl_2$, 200 µM of each dNTP, a Taq polymerase deficient in 5' to 3' exonuclease activity (~1.45 U), Pfu FEN-1 (~23 ng), PE Biosystems β-Actin primers (300 nM each) (CATALOG #600500) and β-actin specific fluorogenic probe (200 nM; 5' FAM-3' TAMRA+PE Biosystems catalog # P/N 401846) were prepared. 10 ng of human genomic DNA (Promega) was used as the target nucleic acid sequence in each reaction. This reaction was performed in a 50 µl volume. Negative control reactions containing either Pfu FEN-1 alone, a Taq polymerase deficient in 5' to 3' exonuclease activity alone or reaction mixtures containing all components except a human genomic DNA template were prepared. Positive control reactions comprising 2.5 Units of Taq 2000 were also prepared. Reactions were assayed in a spectrofluorometric thermocycler (ABI 7700). Thermocycling parameters were 95° C. for 2 min and 40 cycles of 95° C. for 15 sec, 60° C. for 60 sec and 72° C. for 15 sec. Samples were interrogated during the annealing step.

Figure 6:
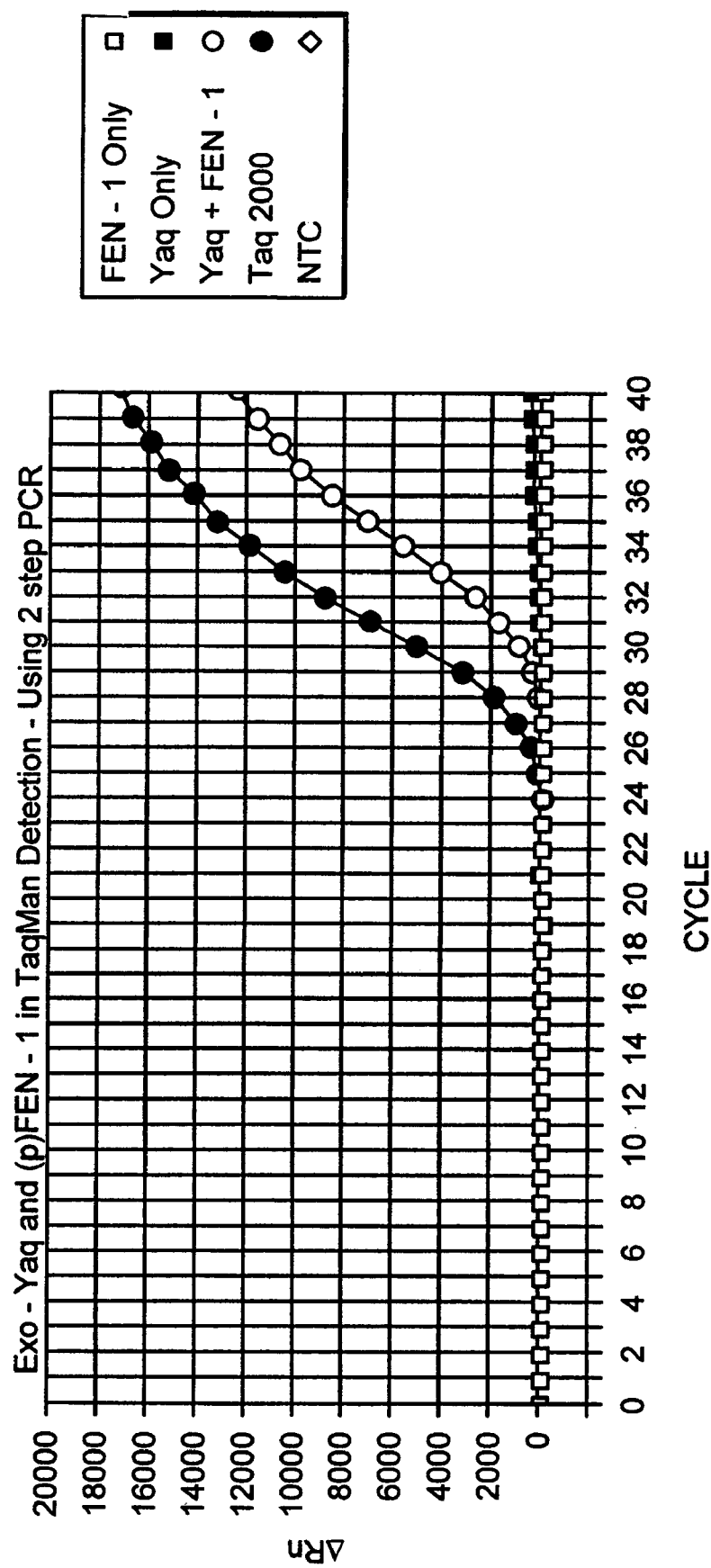
FIG. 6 is a graph representing detection of β-actin sequences in genomic DNA using fluorescently labeled β-actin probe in the presence of FEN-1 and a Taq polymerase deficient in 5' to 3' exonuclease activity.

As demonstrated in FIG. 6, no signal was generated in the presence of either Pfu FEN-1 alone or a Taq polymerase deficient in 5' to 3' exonuclease activity alone. In the presence of both a Taq polymerase deficient in 5' to 3' exonuclease activity and Pfu FEN-1 a signal was generated with a threshold cycle (Ct) of 26 and a final fluorescence intensity (FI) of 12,000 units. In the presence of Taq 2000 (a nucleic acid polymerase which has 5' to 3' exonuclease activity) (Taqman) a signal was generated with a Ct of 23 and a FI of 17,000 units.

These results demonstrate that P-actin DNA sequences can be detected by a PCR assay wherein a signal is generated in the presence of a Taq polymerase deficient in 5' to 3' exonuclease activity and a thermostable FEN-1 nuclease. Further, the 5' to 3' exonuclease activity that is absent in the Taq polymerase deficient in 5' to 3' exonuclease activity can be restored, in trans by the addition of Pfu FEN-1.

Example 5

PCR Amplification and Detection of β-actin in the Presence of a FEN-1 Nuclease and a Pfu Polymerase Deficient in 5' to 3' Exonuclease Activity A PCR assay is used to detect a target nucleic acid sequence. According to the method of this assay, a PCR reaction is carried out in the presence of a Pfu polymerase (naturally lacking 5' to 3' exonuclease activity) or, in addition, Pfu polymerase deficient in 3' to 5' exonuclease activity as well (for example exo-Pfu), and a thermostable FEN-1 nuclease (Pfu FEN-1). Detection of the release of fluorescently labeled fragments indicates the presence of the target nucleic acid sequence.

Duplicate PCR reactions containing 1× Cloned Pfu buffer (available from Stratagene, Catalog #200532), 3.0 mM $MgCl_2$, 200 µM of each dNTP, 5 units of a Pfu polymerase deficient in 3' to 5' exonuclease activity, tagged or untagged Pfu FEN-1 (~23 ng), PEF (1 ng) (described in WO 98/42860), PE Biosystems ᵦ-Actin primers (300 nM each)

(CATALOG #600500), and fluorogenic probe (200 nM; 5' FAM -3' TAMRA+PE Biosystems catalog # P/N 401846) were prepared. 10 ng of human genomic DNA (Promega) was used as the target nucleic acid sequence in each reaction. Reactions were performed in a 50 μl volume. Negative control reactions comprising a Pfu polymerase deficient in both 5' to 3' and 3' to 5' exonuclease activities alone or containing all of the components except the human genomic DNA template were also prepared. A reaction mixture containing 2.5 Units of Taq 2000 was prepared and used as a positive control. Reactions were analyzed in a spectrofluorometric thermocycler (ABI 7700). Thermocycling parameters were 95° C. for 2 min and 40 cycles of 95° C. for 15 sec, 60° C. for 60 sec and 72° C. for 15 sec.

Figure 7:
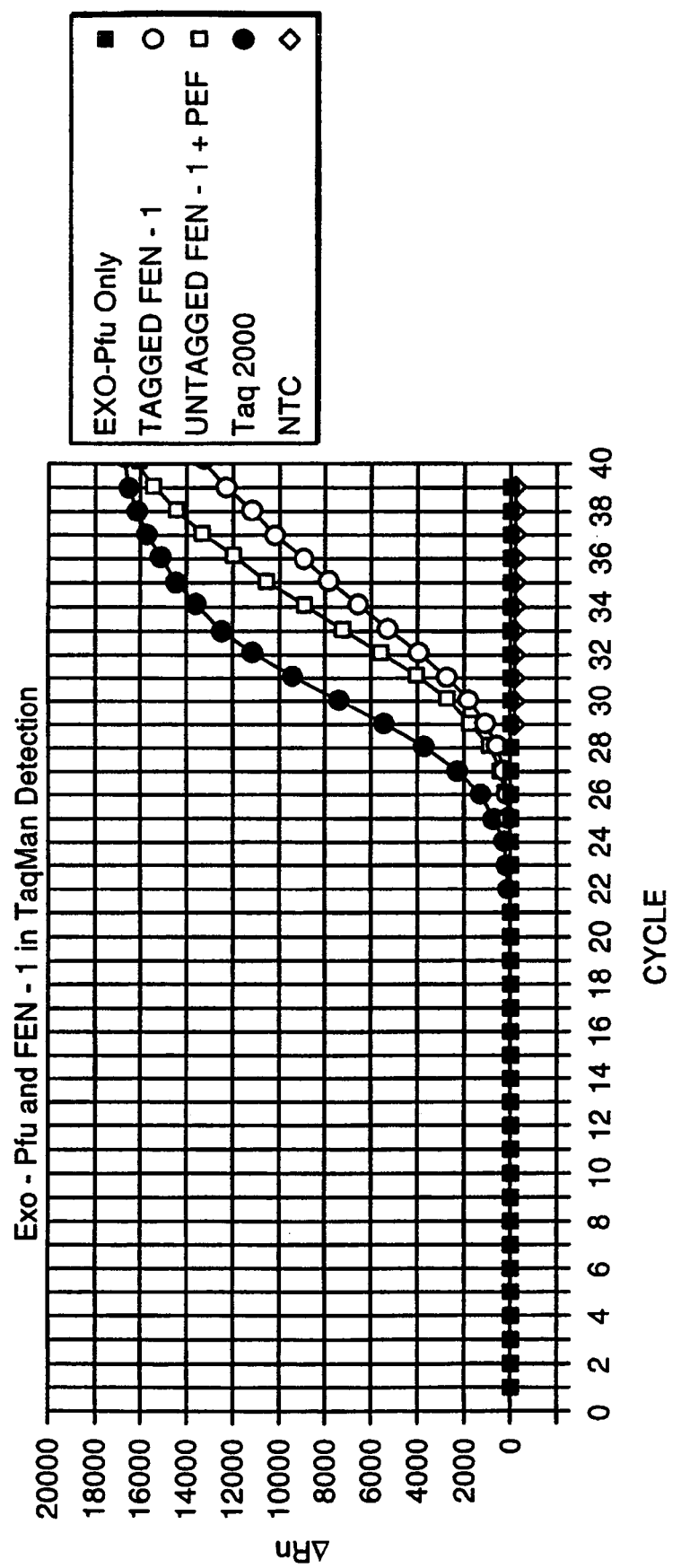
FIG. 7 is a graph representing detection of β-actin sequences in genomic DNA using fluorescently labeled β-actin probe in the presence of FEN-1 and a Pfu polymerase deficient in 3' to 5' exonuclease activity.

As demonstrated in FIG. 7, no signal was generated in the presence of a Pfu polymerase, naturally deficient in 5' to 3' exonuclease activity alone. In the presence of both a Pfu polymerase deficient in 5' to 3' exonuclease activity and tagged Pfu FEN-1 a signal was generated with a threshold cycle (Ct) of 23 and a final fluorescence intensity (FI) of 20,000 units. In the presence of a Pfu polymerase deficient in 5' to 3' exonuclease activity and untagged Pfu FEN-1 a signal was generated with a Ct of 21 and a final FI of 20,000 units. In the presence of Taq 2000, a signal was generated with a Ct of 21 and a FI of 19,000 units (TaqMan).

These results demonstrate that the presence of β-actin target can be detected by a PCR assay wherein a signal is generated in the presence of a Pfu polymerase deficient in 5' to 3' exonuclease activity and a thermostable FEN-1 nuclease. This signal is comparable to the signal generated in the presence of Taq 2000 in the absence of FEN-1. Further, the 5' to 3' exonuclease activity that is absent in a Pfu polymerase can be restored in trans by the addition of Pfu FEN-1.

Example 6

Figure 8A:
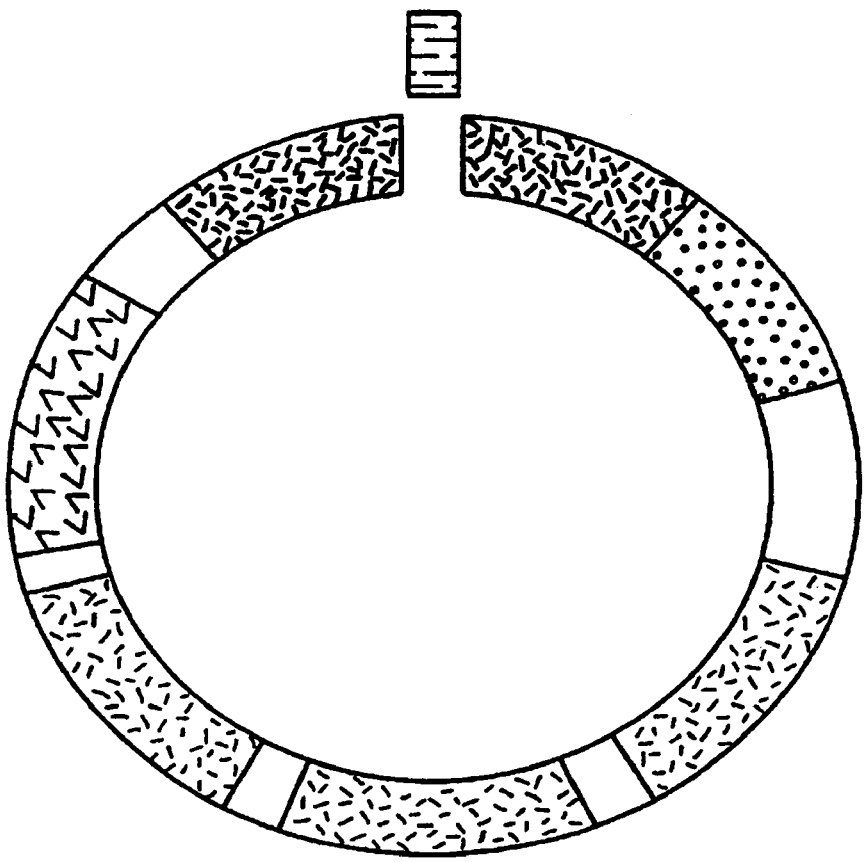
FIG. 8 is a representation of an open circle probe for rolling circle amplification.
Figure 8B:
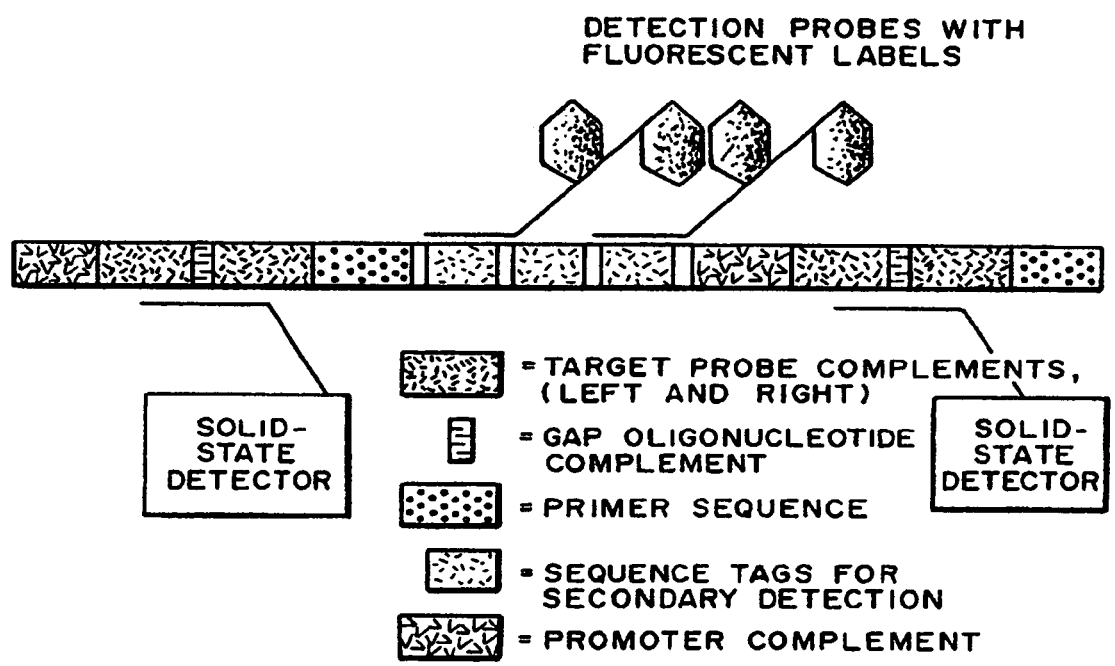
Figure 9B:
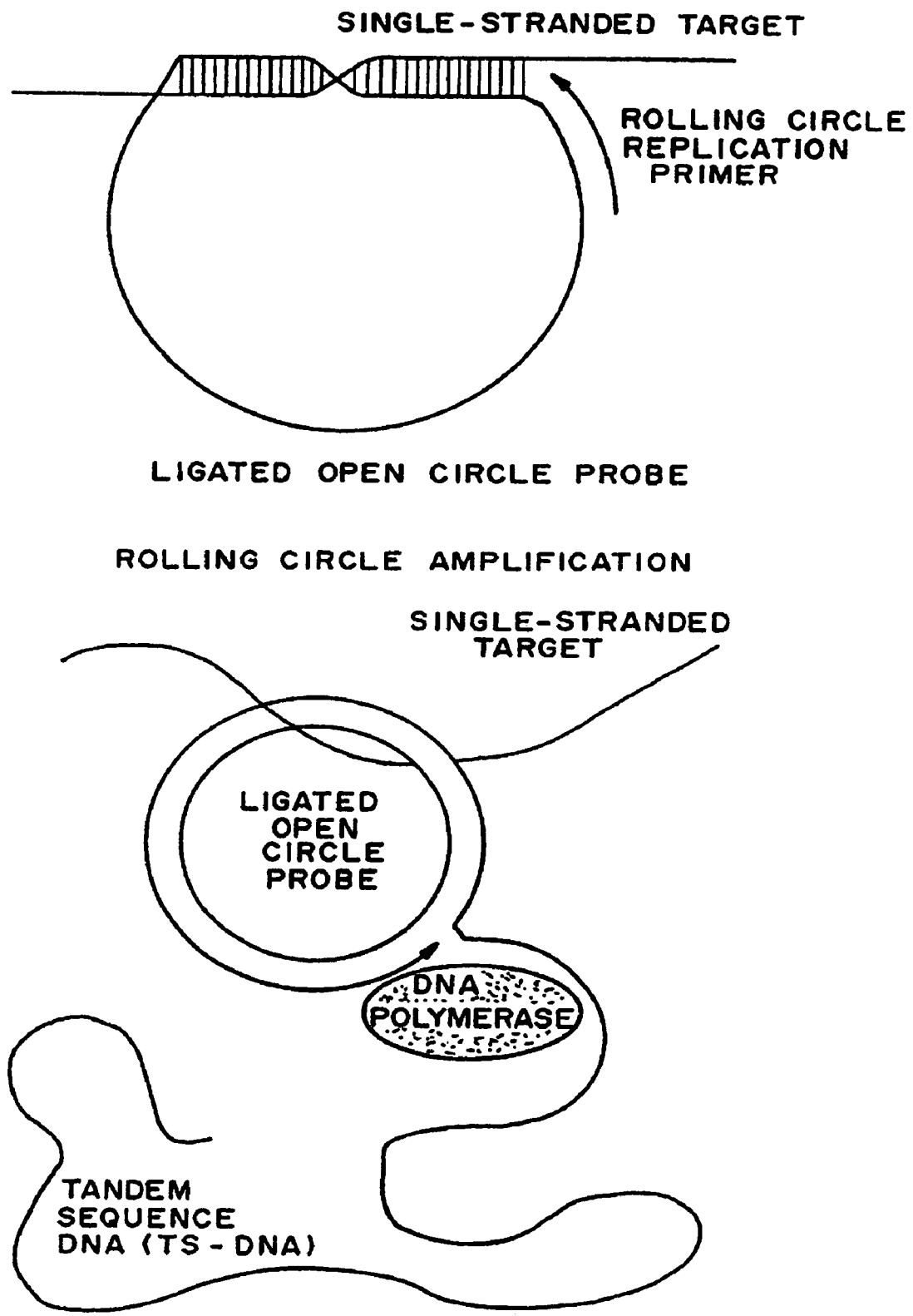
FIG. 9 is a representation of rolling circle amplification.

An assay according to the invention involving rolling circle amplification is performed using the human ornithine transcarbamylase gene as a target, which is detected in human DNA extracted from buffy coat by standard procedures. Target (400 ng) is heat-denatured for 4 minutes at 97° C., and incubated under ligation conditions in the presence of two 5'-phosphorylated oligonucleotides, an open circle probe and one gap oligonucleotide. The open circle probe has the sequence: gaggagaataaaagtttctca taagactcgtcatgtct-cagcagcttctaacggtcactaatacgactcactataggttctgcctctgggaacac (SEQ ID NO: 17), the gap nucleotide for the wild-type sequence is: tagtgatc. FIGS. 8 and 9 depict rolling circle probes and rolling circle amplification. The reaction buffer (40 ul) contains 5 units/⊠1 of T4 DNA ligase (New England Biolabs), 10 mM Tris-HCl, pH 7.5, 0.2 M NaCl, 10 mM MgCl$_2$, 4 mM ATP, 80 nM open circle probe and 100 nM gap oligonucleotide. After incubation for 25 minutes at 37° C., 25 ul are removed and added to 25 ul of a solution containing 50 mM Tris-HCl, pH 7.5, 10 mM MgCl$_2$, 1 mM DTT, 400 μM each of dTTP, dATP, dGTP, dCTP, 0.2⊠M rolling circle replication primer: gctgagacatgacgagtc (SEQ ID NO: 18), phi29 DNA polymerase (160 ng/50 ul). The sample is incubated for 30 minutes at 30° C.

RNA is produced from a T7 promoter present in the open circle probe, by the addition of a compensating buffer (a stock solution or concentrate) that is diluted to achieve the following concentration of reagents: 35 mM Tris-HCl, pH 8.2, 2 mM spermidine, 18 mm MgCl$_2$, 5 mM GMP, 1 mM of ATP, CTP, GTP, 333 uM UTP, 667 uM Biotin-16-UTP, 0.03% Tween 20, 2 units per ul of T7 RNA polymerase. RNA production is performed as described in U.S. Pat. No. 5,858,033. The incubation is allowed to proceed for 90 minutes at 37° C.

Five μl of each sample (the actual test sample, a (−) ligase control sample, a (−) phi29 DNA polymerase control and a (−)T7 RNA polymerase control) in duplicate are removed for detection. The reverse transcription process includes the steps of A) ligating the open circle, B) synthesizing rolling circle single stranded DNA, C) making RNA (from a T7 promoter present in the open circle probe), D) reverse transcribing the RNA to make cDNA, and E) performing PCR amplification of the cDNA using primers and probes for generation of an detection of FEN cleavage structures, according to the invention. For reverse transcription, the reagents and protocols supplied with the Stratagene Sentinel Single-Tube RT-PCR Core Reagent Kit (Cat#600505) are used, except for the substitution of equal amounts of Yaq DNA polymerase for the Taq 2000 DNA polymerase which is recommended by the manufacturer. Each reaction contains 1× Sentinel molecular beacon RT-PCR core buffer, 3.5 mM MgCl$_2$, 200 μM of each dNTP, 5 units exo-Pfu, 23 ng Pfu FEN-1, 1 ng PEF, 500 nM each of the upstream primer: aagttttctcataagactcgtcat (SEQ ID NO: 19), the reverse primer: aggcagaacctatagtgagtcgt (SEQ ID NO: 20), and the fluorogenic probe (for example FAM-DABCYL): agct-tctaacggtcactaatacg (SEQ ID NO: 21). The reactions are subjected to incubation for 30 minutes at 45° C., 3 minutes at 95° C., followed by one cycle in a thermal cycler: 2 minutes at 95° C., 1 minute at 50° C., 1 minute at 72° C. The fluorescence in then determined in a fluorescence plate reader, such as Stratagene's FluorTracker or PE Biosystems' 7700 Sequence Detection System in Plate-Read Mode.

A crosscheck for the efficiency of detection is possible because of the incorporation of Biotin-16-UTP in the rolling circle amplification RNA product. An aliquot of the reactions is captured on glass slides (or alternatively in microwell plates) using an immobilized capture probe. Detection of the captured RNA amplicon is described in detail in U.S. Pat. No. 5,854,033, hereby incorporated by reference.

Example 7

Figure 13:
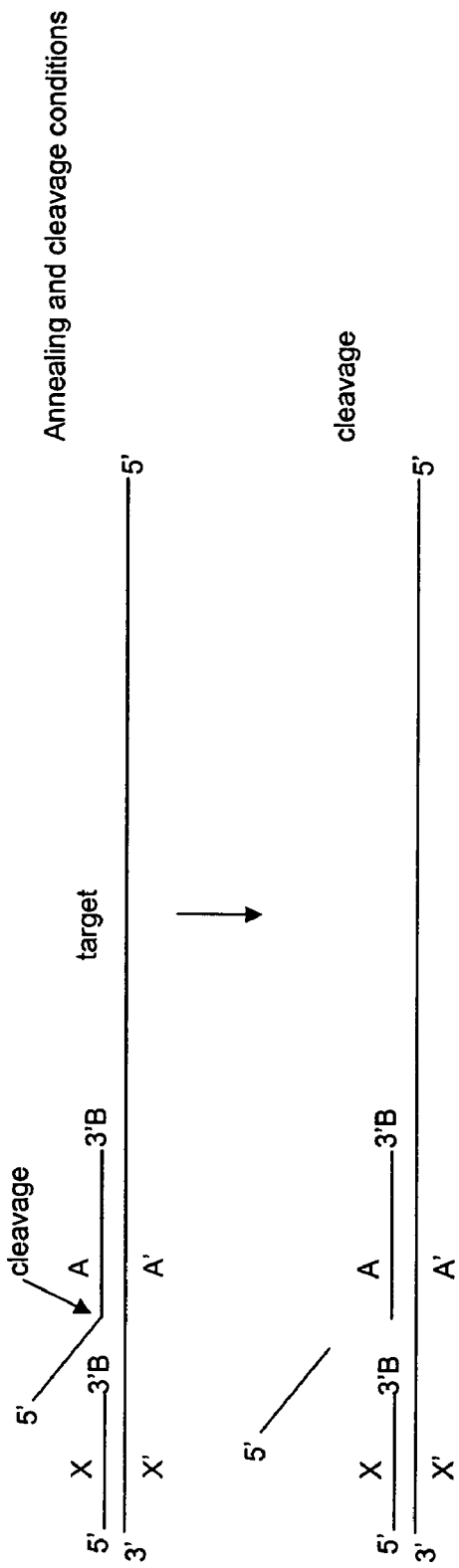
FIG. 13 is a schematic depicting an embodiment of the invention for detection of the target nucleic acid using a blocked upstream oligonucleotide and a blocked downstream probe.

FIG. 13 illustrates a structure where there is a 5' single stranded flap extending from a "downstream" oligonucleotide (marked A), and an upstream oligonucleotide (marked X), both hybridized to a target nucleic acid. The 5' single stranded flap can be one nucleotide or longer. In some embodiments a 5' flap is not present.

The embodiment shown in FIG. 13 does not require the use of a polymerase, although one may be used. FIG. 13 shows an upstream oligonucleotide with a "blocked 3' end", shown as "3'B". The blocked 3' end is a 3' end that an enzyme is incapable of adding nucleotide triphosphates to under normal enzymatic conditions. Extension can be inhibited by blocking the 3' end in many ways, including modification of the 3' hydroxyl group to comprise only a hydrogen (dideoxynucleotide), replacement of the hydrogen of the 3' hydroxyl group with a phosphate group, attachment of a reporter moiety, such as a biotin or a fluorescent group to the 3' carbon or to the 3' oxygen, and other changes to the 3' end that preclude the addition of nucleotide triphosphates to the 3' end.

In some embodiments, the base or bases at the 3' end of the upstream oligonucleotide may not form normal Watson-Crick base pairs with the target. For example, there may be mismatched bases at the 3' end of the upstream oligonucleotide. The mismatched base or bases may be sufficient to inhibit the extension of the 3' end by an enzyme, such as a polymerase, even if the 3' end has a normal 3' hydroxyl. The mismatches at the 3' end include one or more mismatches as long as the upstream oligonucleotide hybridizes to target at appropriate temperature.

The blocked 3' end of the upstream oligonucleotide can be from 0 to 10 bases, preferably 0-5 bases from the 5' terminal hybridized nucleotide of the downstream oligonucleotide. In some embodiments, a nick separates the upstream and downstream oligonucleotides.

5' flap nucleases can cleave the 5' extension of structures such as shown in FIG. 13. The blocked 3' end of the upstream oligonucleotide can either be upstream of, at, or downstream of the 5' terminal hybridized nucleotide of the downstream oligonucleotide.

The cleaved flap can be detected directly, e.g., fluorescent signal from a FRET pair, or indirectly, e.g., secondary cleavage or amplification reaction. See other related patents, the disclosures of which are incorporated herein by reference for direct detection (U.S. patent application Ser. No. 10/981,942, filed Nov. 5, 2004; U.S. Pat. No. 6,528,254 B1, filed Oct. 29, 1999; U.S. Pat. No. 6,548,250, filed Aug. 30, 2000) and indirect detection (U.S. Pat. No. 6,893,819, filed Nov. 21, 2000; U.S. Application 60/725,916, filed Oct. 11, 2005.)

Example 8

Figure 14:
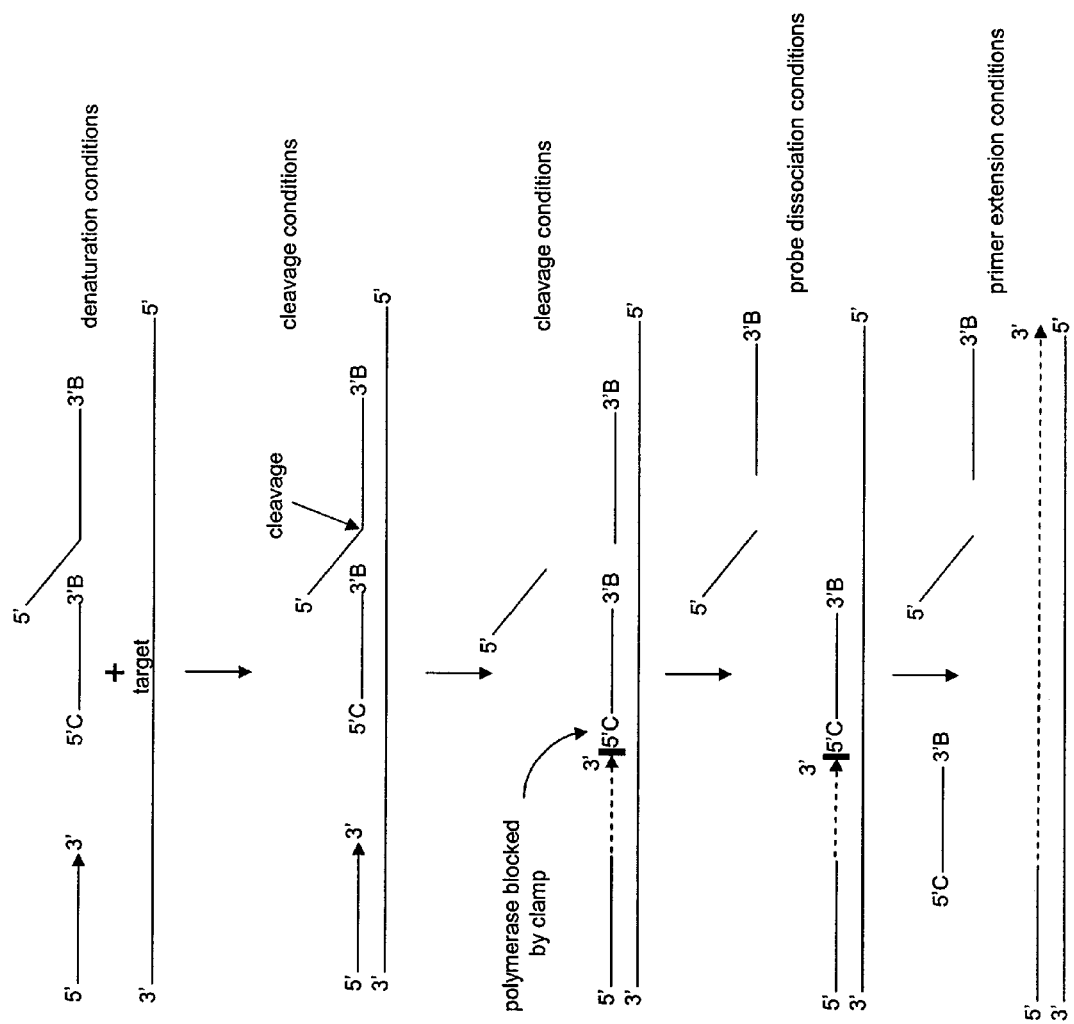
FIG. 14 is a schematic depicting an embodiment of the invention for simultaneous detection of the target and generation of a strand complementary to the target nucleic acid using a 3' blocked upstream oligonucleotide having a clamp.

Description of Probes:

FIG. 14 depicts the upstream and downstream probes of FIG. 13 in a cleavage reaction with nucleic amplification. In addition to the requirements of Example 7, the method also employs at least one extension primer which hybridizes 5' to the upstream oligonucleotide. The extension primer can be about 10-25 nucleotides (nts) long. It is important that the primer extension product does not form a cleavage structure with either the upstream oligonucleotide or downstream oligonucleotide probe. This is controlled by a clamp on the 5' end of the upstream oligonucleotide which prohibits its displacement by the polymerase. The clamp can be any modification that allows the upstream clamping oligonucleotide to bind to the target with such high affinity so as to prevent its displacement by the extending polymerase. Such modifications are known in the art and include minor groove binders, intercalating agents, GC rich regions, LNAs.

The upstream clamping oligonucleotide and downstream probe can melt at identical temperatures (as long as no cleavage structure is formed with the extension product) but preferably the upstream clamping oligonucleotide melts at a higher temperature.

Description of Method:

Anneal/Extension: In one embodiment, all three oligonucleotides are anneal to the target at about 55-65° C. Once annealed the polymerase extends the primer up to the clamp. The polymerase is unable to displace the clamped upstream clamping oligonucleotide and therefore stops. The cleavage structure formed by the upstream and downstream oligonucleotide probe is cleaved (See description in Example 7 for FIG. 13).

The temperature of the reaction is then increased, preferably to 65-75° C., allowing the downstream oligonucleotide probe (5-10 ° C. more than cleavage temp) and then the upstream clamping oligonucleotide (an additional 5 ° C. greater than cleavage temp) to dissociate. With the clamped upstream oligonucleotide dissociated, the polymerase is able to further extend the extension product through the target.

Example 9

Figure 15:
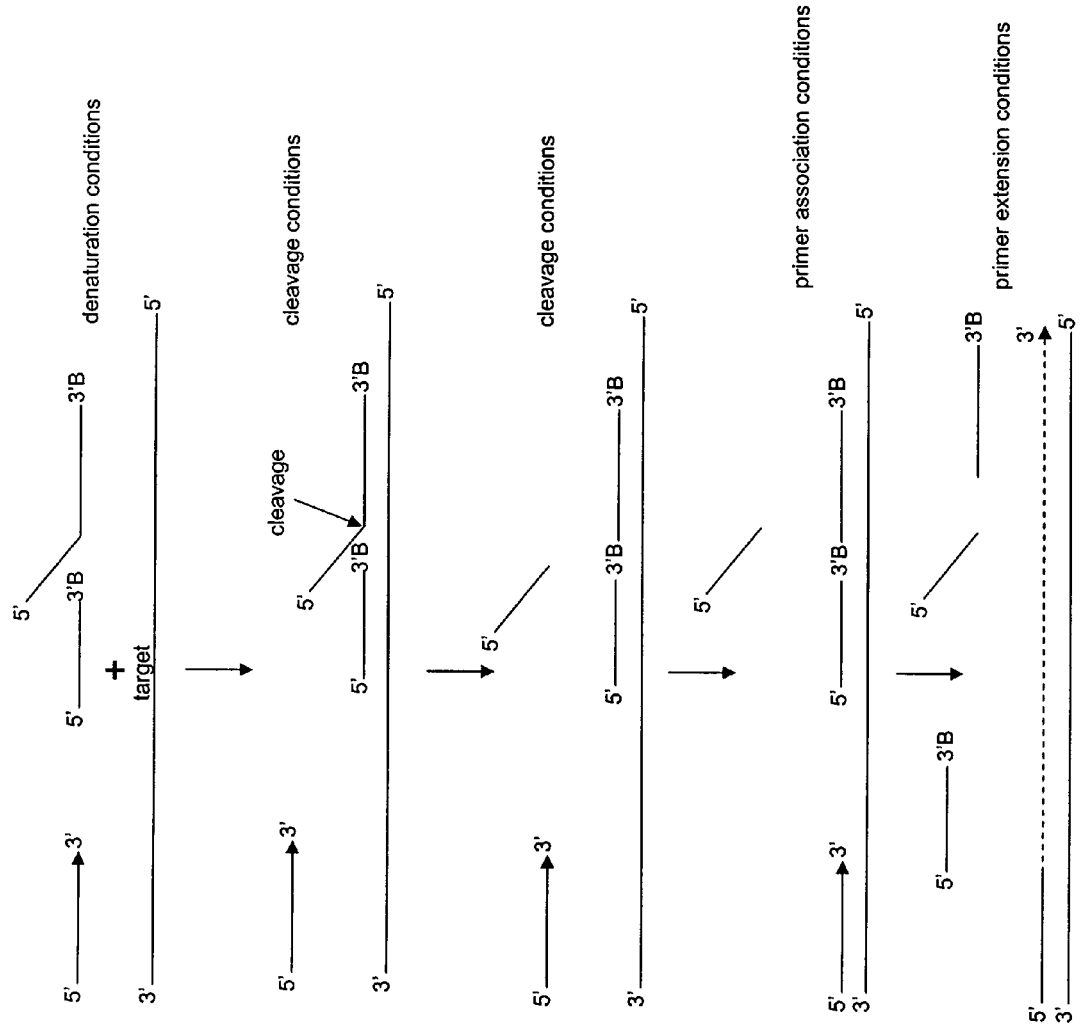
FIG. 15 is a schematic depicting another embodiment of the invention for simultaneous detection of the target and generation of a strand complementary to the target nucleic acid using a 3' blocked upstream oligonucleotide

Description of Probes:

FIG. 15 depicts the upstream and downstream probes of FIG. 13 in a cleavage reaction involving nucleic amplification. In addition to the requirements of FIG. 13, the method also employs at least one primer which hybridizes 5' to the upstream oligonucleotide. The primer hybridizes to the target at about 55-65 ° C. The upstream and downstream oligonucleotides are designed to anneal to the target at about 10° C. higher (or under higher stringency conditions (DMSO, pH, salt concentration)) than the primer.

Description of Method:

Anneal/Cleavage: In this embodiment, the upstream and downstream oligonucleotides anneal to the target (65-75 ° C.). When the upstream and downstream oligonucleotides are annealed to the target the downstream oligonucleotide probe is cleaved by FEN (as described in Example 7 with respect to FIG. 13).

Anneal/Extension: The reaction temperature is decreased allowing the primer to anneal to the target. The primer is then extended causing in the displacement of the upstream and downstream oligonucleotides.

Example 10

Figure 16:
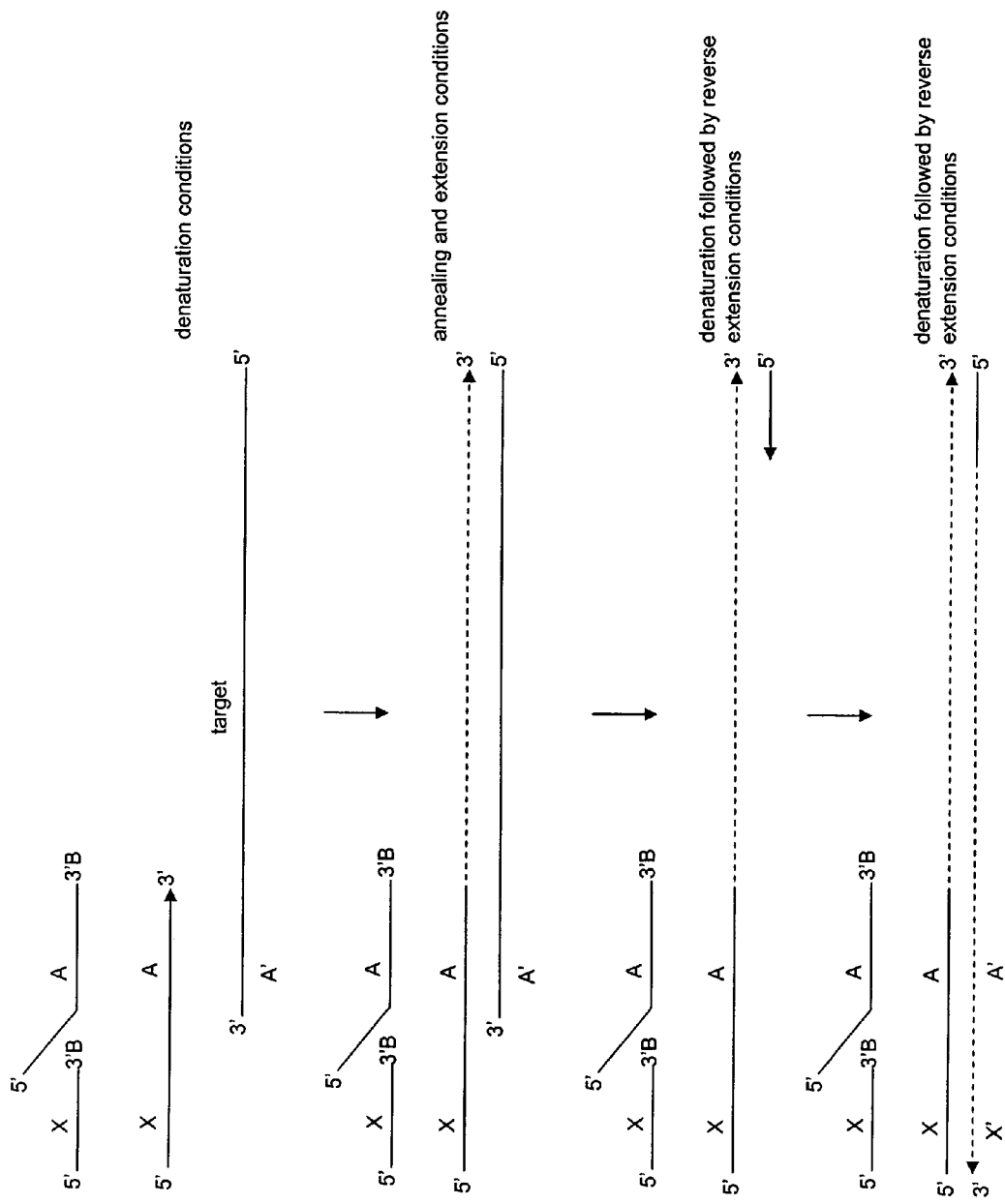
FIG. 16 is a schematic depicting another embodiment of the invention for simultaneous detection of the target nucleic acid and amplification thereof using a 3' blocked upstream oligonucleotide.
Figure 16B:
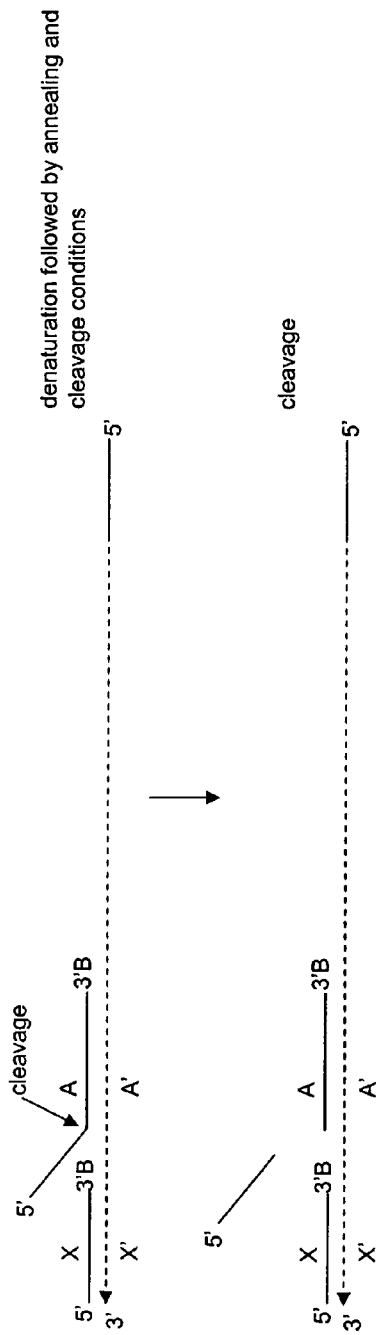

Description of Probes:

FIG. 16 shows the upstream oligonucleotide and downstream probe of FIG. 13 in a cleavage reaction with nucleic amplification. The amplification reaction incorporates a primer nucleic acid which is shared with the upstream oligonucleotide. This nucleic acid sequence is not present in the target prior to amplification.

The extension primer (XA) anneals to the target via the 3' A region. The 5' X region of the primer is not present in the target until the X region is incorporated into the amplicon. The X regions of both the upstream oligonucleotide and extension primer are about 20 nts long. Similarly, the A region of the downstream oligonucleotide and extension primer are also about 20 nts long. The downstream probe can further include a region downstream of A that is complementary to the target. This region enhances the downstream probe's specificity for the target. For example, this region can be 5-15 nucleotides long. The A sequence of the downstream probe can be shortened based on the number of corresponding nucleotides added downstream of A. The method may also use a reverse primer.

Description of Method

Anneal/Extension: In this embodiment, the extension primer anneals to the target via the A region of the primer. The primer is extended by the polymerase, thus incorporating the X region into the amplicon. Primer annealing and extension occurs under normal annealing/extension conditions. The nucleic acid is then denatured.

Anneal/Extension: During subsequent rounds of amplification, the reverse primer anneals to the synthesized strand and primes the synthesis of a complementary strand. The reverse primer extension reaction synthesizes a region complementary to the X region of the primer (and X region of upstream oligonucleotide). Thus the complementary nucleic acid strand has binding regions (X'A') for both the upstream and downstream oligonucleotides. The reaction is heated to denature the oligonucleotides.

Anneal/Extension/Cleavage: In the next annealing/extension reaction the upstream and downstream oligonucleotides anneal to the target creating the cleavage structure described in Example 7 with respect to FIG. 13. The cleavage reaction proceeds as described in Example 7.

Example 11

Figure 17:
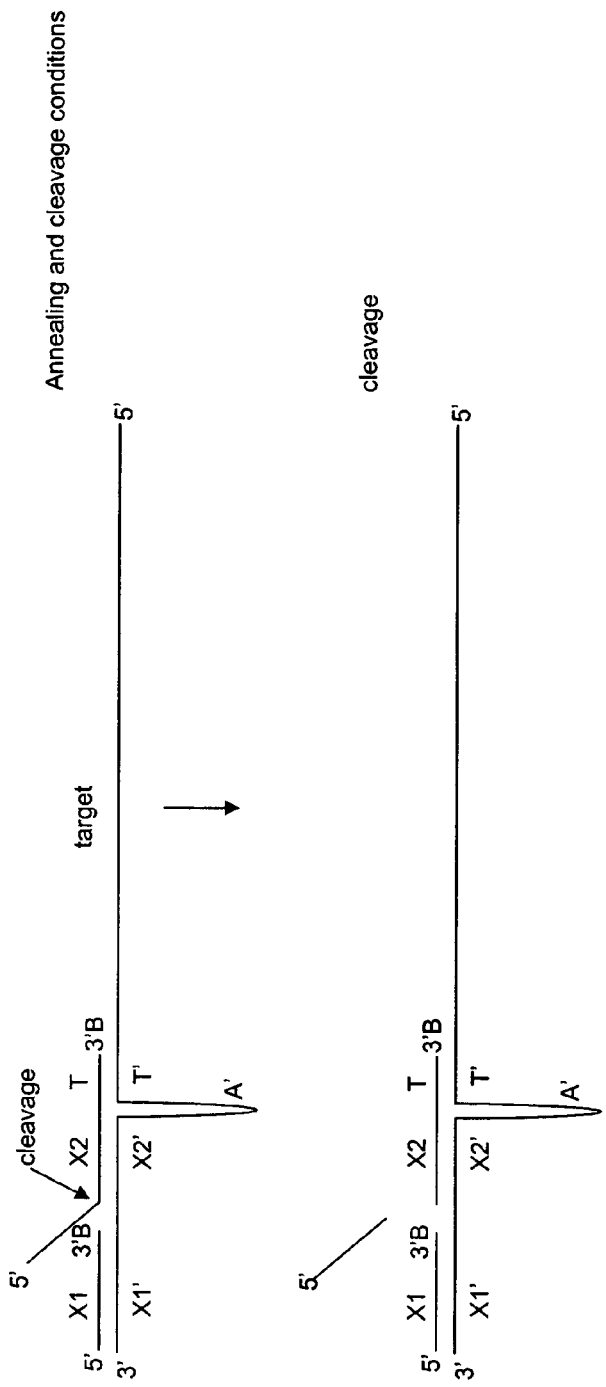
FIG. 17 is a schematic depicting yet another embodiment of the invention for detection of the target nucleic acid using a 3' blocked upstream oligonucleotide and a 3' blocked downstream probe which is complementary to non-contiguous regions of the target.

Description of Probes:

FIG. 17 shows a variation of the upstream and downstream probes of FIG. 13 in a cleavage reaction in which the downstream probe hybridizes to two non-contiguous regions of the target (X2'T'). Thus, a portion of the target (A') that is non-complementary to the target does not hybridize to the downstream probe. In some embodiments, region T is between 1-25 nts long. In some embodiments, A' is about 20 nts or less. Generally A' is a region that is sufficiently long so as to prevent a primer from binding to the target. Such methods reduce the competition between the downstream oligonucleotide probe and PCR primers for target binding (see also FIG. 18).

Example 12

Figure 18:
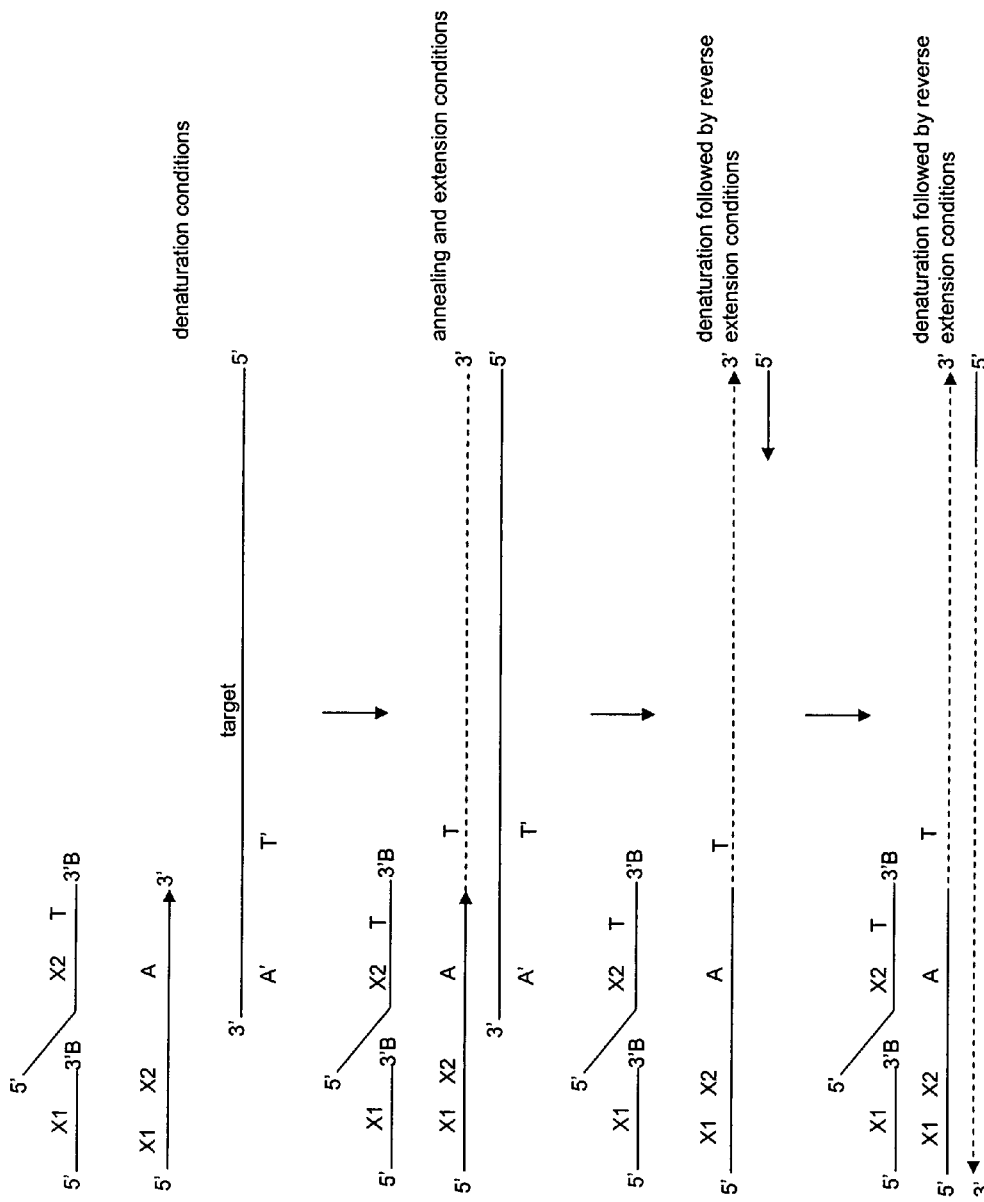
FIG. 18 is a schematic depicting an embodiment of the invention for simultaneous detection of the target nucleic acid and amplification thereof using a 3' blocked upstream oligonucleotide and a 3' blocked downstream probe which is complementary to non-contiguous regions of the target.
Figure 18B:
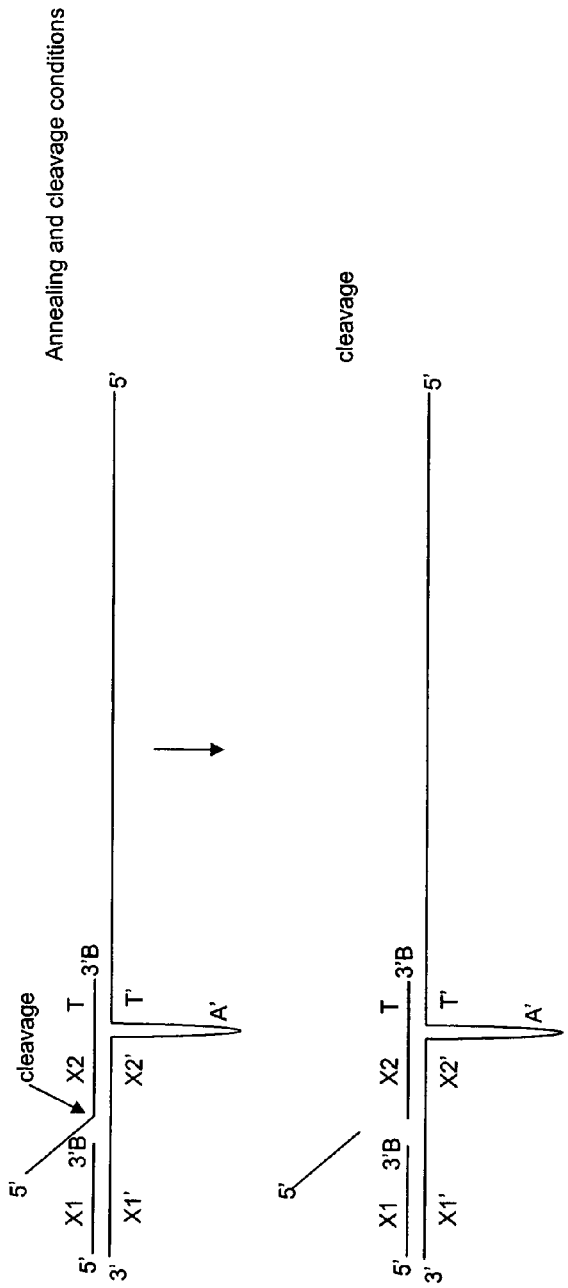

Description of Probes:

FIG. 18 shows a variation of the upstream and downstream probes of FIG. 13, FIG. 16 and FIG. 17 in a cleavage reaction which includes nucleic acid amplification. The method employs a upstream signal oligonucleotide (X1), a downstream oligonucleotide probe (X2, T), an extension primer (X1, X2, A) and a reverse primer. The 3' A region of the primer is complementary to and anneals with the A' region of the target. The X1 and X2 sequences are not present in the target until the primer is incorporated into the amplicon. The T region of the oligonucleotide is complementary to a portion of the target that is downstream of A'. The X1 region can be about 20 nts long. In some embodiments, the X2 and T regions can be 1-25 nts long, preferably 10-15, but together they should be about 20 nts or sufficiently long to anneal to the target at the appropriate temperature.

Description of Method

Anneal/Extension: The primer's A region anneals to the target's A' region and a polymerase extends the 3' end of the X1X2A primer thus incorporating the X1 and X2 regions into the amplicon. The reaction is denatured under normal denaturing conditions.

Anneal/Extension: Another round of annealing and extension is performed. In this annealing/extension reaction the reverse primer anneals to the target and is extended, thus synthesizing a complementary nucleic acid with X1'X2' portions that are complementary to the X1 and X2 portions of the incorporated primer. The reaction is heated and the oligonucleotides are denatured.

Anneal/Extension: During the next round of annealing and extension the X1X2T portions of the upstream and downstream oligonucleotides anneal to the amplified product. Annealing of the X1 and X2 and T portions loops out the intervening A portion (primer binding portion) of the target. The annealed upstream and downstream oligonucleotides form a cleavage structure like that described in Example 7 with respect to FIG. 13.

Example 13

A target nucleic acid can be detected and/or measured by the following method. A reaction mixture is prepared having:

150 nM of a 3' $PO_3$ blocked upstream oligonucleotide;
150 nM of a downstream oligonucleotide probe having a 5' flap;
150 nM of PCR template; and either
1X FullVelocity™ QPCR Master Mix (Stratagene Catalog No. 600561; 200 ng of Fen and 2.5 U of Pfu V93R, exo-, DNA polymerase) or
200 ng Fen in 1X no enzyme FullVelocity™ QPCR Master The experiments were conducted on an Mx3000p real-time PCR instrument (Stratagene) with the following cycling parameters 95° C. for 2 minutes; 95° C. for 10 seconds, 6° C. for 30s for 40 cycles with a fast cooling curve.

The upstream oligonucleotide hybridized to the PCR template just upstream of the downstream oligonucleotide probe. Thus, the upstream oligonucleotide and the complementary portion of the 5' flapped probe did not overlap. Control studies confirmed that the upstream oligonucleotides were completely blocked and did not allow primer extension.

Figure 19:
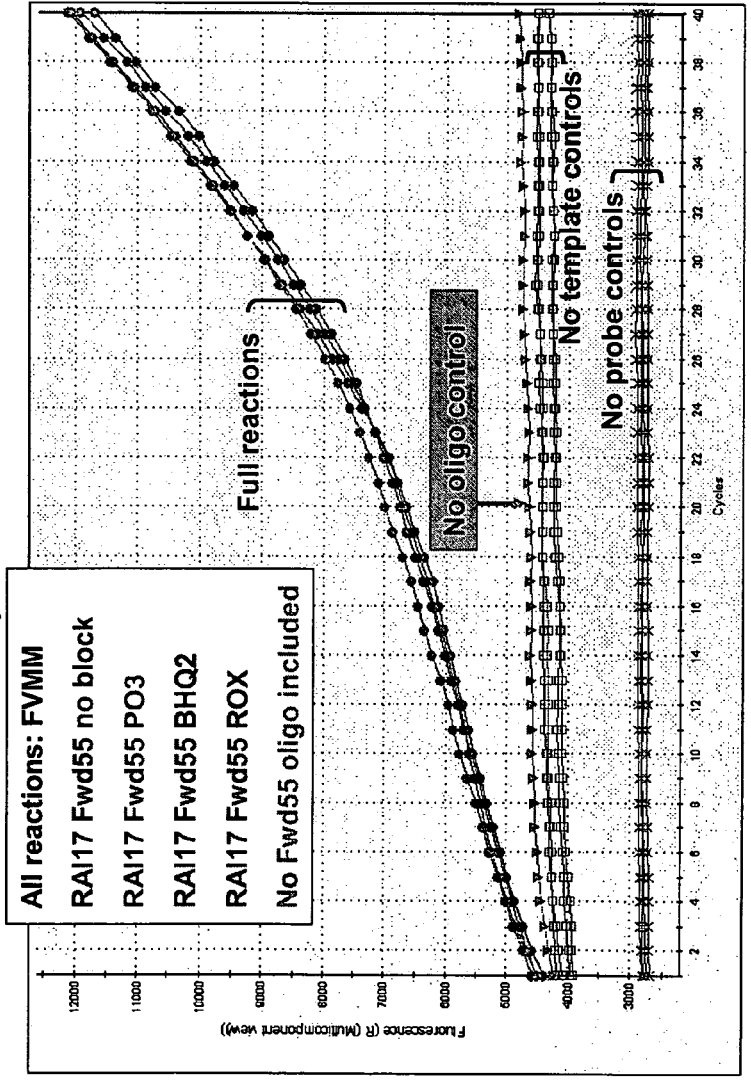
FIG. 19 is a graph depicting fluorescence v. cycles in a FullVelocity reaction utilizing a 3' blocked probe.
Figure 20:
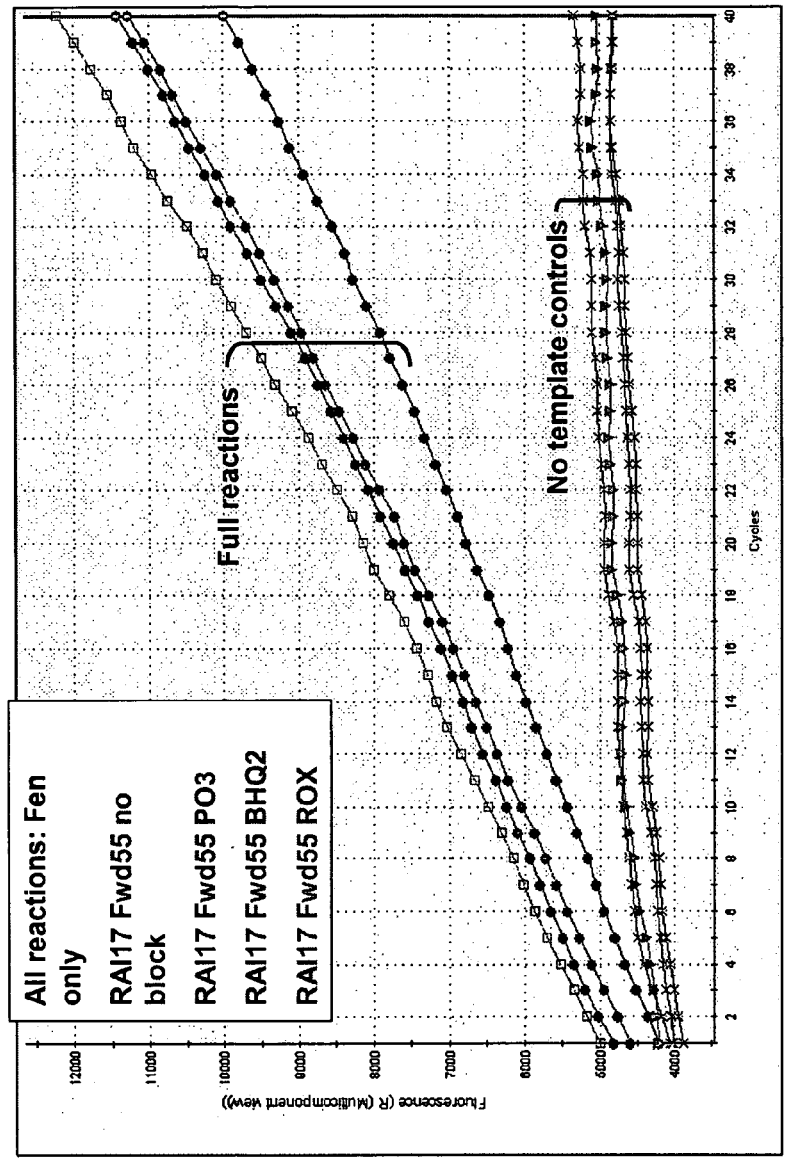
FIG. 20 is a graph depicting fluorescence v. cycles in a FEN reaction utilizing a 3' blocked probe.

Results are depicted in FIG. 19 and 20, which indicate that FEN is able to cleave a 5' non-complementary flap in the presence of a 3' blocked, upstream oligonucleotide that does not overlap with the region where the 5' flapped probe is complementary to the target.

Dissociation curve experiments were also performed for reactions containing FEN and the polymerase and reactions containing FEN only. The dissociation curve experiments were performed as described above, but fluorescence was measured from 95° C. to 25° C. with rapid cooling. Results indicated that fluorescence was elevated though out the temperature range for the 3' blocked primers when compared to no template and no probe controls.

Other Embodiments

Other embodiments will be evident to those of skill in the art. It should be understood that the foregoing detailed description is provided for clarity only and is merely exemplary. The spirit and scope of the present invention are not limited to the above examples, but are encompassed by the following claims.

What is claimed is:

1. A method for detecting the presence of a target nucleic acid, wherein the method comprises:
   a) providing:
      a target nucleic acid, which comprises in the 3' to 5' order a first hybridization site and a second hybridization site; an upstream oligonucleotide that is complementary to the first hybridization site and wherein the upstream oligonucleotide has a blocked 3' end, and
      a downstream probe comprising a 5' region and a 3' region, wherein the 3' region is complementary to the second hybridization site and the 5' region forms a non-complementary 5' flap when the downstream probe is annealed to the target;
   b) annealing the upstream oligonucleotide and the downstream probe to the target nucleic acid to form a cleavage structure;
   c) cleaving the cleavage structure with a nuclease to release the non-complementary 5' flap; and
   d) detecting the released non-complementary 5' flap, wherein the released non-complementary 5' flap is indicative of the presence of the target nucleic acid in the sample.

2. The method of claim 1, wherein the non-complementary 5' flap of the downstream probe consists of n nucleotides and the first hybridization site and the second hybridization site are separated by m-nucleotides, wherein n is an integer from 1 to 25 and m is an integer greater than n.

3. The method of claim 1, wherein a cleavage structure is formed comprising at least one labeled moiety capable of providing a signal.

4. The method of claim 1, wherein the nuclease comprises a FEN nuclease.

5. The method of claim 4, wherein the FEN nuclease is a flap-specific nuclease.

6. The method of claim 4, wherein the FEN nuclease is thermostable.

7. The method of claim 4, wherein the FEN nuclease is selected from the group consisting of FEN nuclease enzyme derived from *Archaeglobus fulgidus*, *Methanococcus jannaschii*, and *Pyrococcus furiosus*.

8. The method of claim 4, wherein the cleavage structure formed comprises a pair of interactive signal generating labeled moieties effectively positioned to quench the generation of a detectable signal, the labeled moieties being separated by a site susceptible to FEN nuclease cleavage, thereby allowing the nuclease activity of the FEN nuclease to separate the first interactive signal generating labeled moiety from the second interactive signal generating labeled moiety by cleaving at the site susceptible to FEN nuclease, thereby generating a detectable signal.

9. The method of claim 8, wherein the pair of interactive signal generating moieties comprises a quencher moiety and a fluorescent moiety.

10. The method of claim 1, further comprising the step of quantifying the released non-complementary 5' flap.

11. The method of claim 1, wherein the 3' end of the downstream probe is blocked to prevent 3' extension of the downstream probe.

12. The method of claim 1, wherein the 3' portion of the downstream probe is further complementary to a third hybridization site of the target nucleic acid, wherein the third hybridization site is 5' to the second hybridization site and the second hybridization site and third hybridization site are separated by an intervening region of the target nucleic acid.

13. The method of claim 12, wherein the 3' portion of the downstream probe hybridizes to the second and third hybridization sites and wherein the intervening region of the target nucleic acid comprises a non-complementary region.

14. The method of claim 12, wherein the 3' portion of the downstream probe is 1-25 nucleotides and the intervening region is 1-20 nucleotides.

15. The method of claim 11, wherein one or both of the blocked 3' ends comprises a base that is non-complementary to the target nucleic acid or a modification that inhibits addition of a nucleotide triphosphate under conditions which permit nucleic acid synthesis or extension.

16. The method of claim 15, wherein one or both of the blocked 3' end comprises:
   a) a dideoxynucleotide;
   b) a nucleotide wherein the 3' hydroxyl has been replaced with a phosphate group; or
   c) a nucleotide with a reporter moiety attached to the 3' carbon or to the 3' oxygen.

17. A method for forming a cleavage structure in a sample, cleaving the cleavage structure, and transcribing a nucleic acid complementary to the target nucleic acid, wherein the method comprises:
   a) providing:
      a target nucleic acid, which comprises in the 3' to 5' order a first hybridization site, a second hybridization site and a third hybridization site,
      an upstream extension primer that is complementary to the first hybridization site;
      a clamping oligonucleotide that is complementary to the second hybridization site and wherein the clamping oligonucleotide comprises a blocked 3' end and a 5' end with a clamp, wherein the clamp inhibits the displacement of the clamping oligonucleotide by a nucleic acid polymerase, and
      a downstream probe comprising a 5' region and a 3' region, wherein the 3' region is complementary to the third hybridization site and the 5' region forms a non-complementary 5' flap when the downstream probe is hybridized to the target nucleic acid;

b) annealing the upstream extension primer, the clamping oligonucleotide, and the downstream probe to the target nucleic acid, wherein the clamping oligonucleotide and downstream probe form a cleavage structure;

c) cleaving the cleavage structure with a nuclease to release the non-complementary 5' flap;

d) extending a complementary strand from the upstream extension primer to the clamp of the clamping oligonucleotide;

e) dissociating the clamping oligonucleotide and the downstream probe from the target nucleic acid to allow the nucleic acid polymerase access to the target nucleic acid previously covered by the clamping oligonucleotide and the downstream probe;

f) further extending the strand complementary to the target nucleic acid; and g) detecting the released non-complementary 5' flap, wherein the released non-complementary 5' flap is indicative of the presence of the target nucleic acid in the sample.

18. The method of claim 17, wherein the upstream extension primer anneals to the target nucleic acid under more stringent conditions than the clamping oligonucleotide, and the clamping oligonucleotide anneals to the target nucleic acid under more stringent conditions than the downstream labeled probe.

19. The method of claim 18, wherein:

a) annealing step b) takes place at a temperature below the annealing temperatures of the upstream extension primer, the clamping oligonucleotide, and the downstream probe; and b) dissociating step f) further comprises:

i) increasing the temperature so that the downstream probe is dissociated from the target nucleic acid while the upstream extension primer and the clamping oligonucleotide remain annealed; and ii) further increasing the temperature so that the clamping oligonucleotide is dissociated from the target nucleic acid while the upstream extension primer remains annealed.

20. A method for forming a cleavage structure in a sample, cleaving the cleavage structure, and transcribing a nucleic acid complementary to the target nucleic acid, wherein the method comprises:

a) providing: a target nucleic acid, which comprises in the 3' to 5' order a first hybridization site, a second hybridization site and a third hybridization site, an upstream oligonucleotide extension primer that is complementary to the first hybridization site, an upstream oligonucleotide that is complementary to the second hybridization site and wherein the upstream oligonucleotide comprises a blocked 3' end, and a downstream probe comprising a 5' region and a 3' region, wherein the 3' region is complementary to the third hybridization site and the 5' region forms a non-complementary 5' flap when the downstream probe is annealed to the target;

b) annealing the upstream oligonucleotide and the downstream probe to the target nucleic acid to form a cleavage structure;

c) cleaving the cleavage structure with a nuclease to release the non-complementary 5' flap;

d) annealing the upstream extension primer to the target nucleic acid;

e) extending the upstream oligonucleotide extension primer to synthesize a strand complementary to the target nucleic acid; and f) detecting the released non-complementary 5' flap, wherein the released non-complementary 5' flap is indicative of the presence of the target nucleic acid in the sample.

21. A method for forming a cleavage structure in a sample, cleaving the cleavage structure, transcribing a nucleic acid complementary to the target nucleic acid, and amplifying the target nucleic acid, wherein the method comprises:

a) providing:

a target nucleic acid, which comprises region A', a forward extension primer comprises a non-complementary 5' tag region (X) and a 3' priming region (A), wherein the 5' tag region is not complementary to the target prior to amplification and the 3' priming region (A) is complementary to region (A') in the target nucleic acid, an upstream oligonucleotide comprising at least a portion of region X and wherein the upstream oligonucleotide has a blocked 3' end, a downstream probe comprising a 5' region and a 3' region, wherein the 3' region comprises at least a portion of region A and the 5' region forms a non-complementary 5' flap when the downstream probe is annealed to the A' portion of the target nucleic acid, and a reverse extension primer that primes a second strand comprising at least a portion of the target nucleic acid;

b) annealing region A of the forward extension primer to the target nucleic acid;

c) extending the forward extension primer to produce a complementary strand of the target nucleic acid, wherein the complementary strand includes region A and region X;

d) denaturing the target nucleic acid and the complementary strand;

e) annealing the reverse extension primer to a region of the complementary strand downstream of region A;

f) extending the strand from the reverse extension primer to produce a second strand comprising at least a portion of the target nucleic acid sequence, region A', and a region (X') complementary to the 5' tag;

g) denaturing the complementary strand from the second strand;

h) annealing the upstream oligonucleotide and the downstream probe to the second strand to form a cleavage structure;

i) cleaving the cleavage structure with a nuclease to release the non-complementary 5' flap of the downstream oligonucleotide; and j) detecting the released non-complementary 5' flap, wherein the released non-complementary 5' flap is indicative of the presence of the target nucleic acid in the sample.

22. The method of claim 21, further comprising repeating the denaturation, extension, and cleavage cycles to amplify the target sequence, form the cleavage structure, and cleave the cleavage structure under conditions which are permissive for PCR cycling steps.

23. The method of claim 21, wherein the nucleic acid polymerase substantially lacks 5' to 3' exonuclease activity.

24. The method of claim 21, wherein the 5' flap of the downstream probe consists of n nucleotides and the hybridization sites of the upstream signal oligonucleotide and the downstream probe are separated by an m-nucleotides, wherein n is an integer from 1 to 25 and m is an integer greater than n.

25. The method of claim 21, wherein the nuclease comprises a FEN nuclease.

26. The method of claim 25, wherein the FEN nuclease is selected from the group consisting of FEN nuclease enzyme derived from *Archaeglobus fulgidus, Methanococcus jannaschii*, and *Pyrococcus furiosus*.

27. The method of claim 21, wherein a cleavage structure is formed comprising at least one labeled moiety capable of providing a signal.

28. The method of claim 21, wherein the cleavage structure formed comprises a pair of interactive signal generating labeled moieties effectively positioned to quench the generation of a detectable signal, the labeled moieties being separated by a site susceptible to FEN nuclease cleavage, thereby allowing the nuclease activity of the FEN nuclease to separate the first interactive signal generating labeled moiety from the second interactive signal generating labeled moiety by cleaving at the site susceptible to FEN nuclease, thereby generating a detectable signal.

29. The method of claim 28, wherein the pair of interactive signal generating moieties comprises a quencher moiety and a fluorescent moiety.

30. The method of claim 21, further comprising the step of quantifying the released non-complementary 5' flap.

31. The method of claim 21, wherein the 3' end of the downstream probe is blocked to prevent 3' extension of the downstream probe.

32. The method of claim 31, wherein one or both of the blocked 3' ends comprises a base that is non-complementary to the target nucleic acid or a modification that inhibits addition of a nucleotide triphosphate under conditions which permit nucleic acid synthesis or extension.

33. The method of claim 32, wherein one or both of the blocked 3' end comprises:
    a) a dideoxynucleotide;
    b) a nucleotide wherein the 3' hydroxyl has been replaced with a phosphate group; or
    c) a nucleotide with a reporter moiety attached to the 3' carbon or to the 3' oxygen.

34. A method for forming a cleavage structure in a sample, cleaving the cleavage structure, transcribing a nucleic acid complementary to the target nucleic acid, and amplifying the target nucleic acid, wherein the method comprises:
    a) providing:
        a target nucleic acid, which comprises from 3' to 5' an A' region and a T' region, wherein said A' and T' regions are non-contiguous,
        a forward extension primer comprises a 5' tag region comprising two subregions (X1 and X2), wherein X1 is upstream of X2 and a 3' priming region (A), wherein the 5' tag region is not complementary to the target prior to amplification and the 3' priming region (A) is complementary to region A' of the target nucleic acid,
        an upstream oligonucleotide comprising at least a portion of region X1 and wherein the upstream oligonucleotide has a blocked 3' end,
        a downstream probe comprising a 5' region and a 3' region, wherein the 3' region comprises at least a portion of region X2, and a region T which is downstream of region X2 and is complementary to T' of the target nucleic acid, and wherein the 5' region forms a non-complementary 5' flap when the downstream probe is annealed to the A' region of the target nucleic acid, and
        a reverse extension primer that primes a second strand comprising at least a portion of the target nucleic acid;
    b) annealing complementary region A of the forward extension primer to the A' region and T' region of the target nucleic acid;
    c) extending the forward extension primer to produce a complementary strand of the target nucleic acid, wherein the complementary strand includes region A and regions X1 and X2;
    d) denaturing the target nucleic acid and the complementary strand;
    e) annealing the reverse extension primer to a region of the complementary strand downstream of region T;
    f) extending the strand from the reverse extension primer to produce a second strand comprising at least a portion of the target nucleic acid sequence, region A', region T' and a region (X1', X2') complementary to the 5' tag;
    g) denaturing the complementary strand from the second strand;
    h) annealing the upstream oligonucleotide and the downstream probe to the second strand to form a cleavage structure
    i) cleaving the cleavage structure with a nuclease to release the non-complementary 5' flap of the downstream oligonucleotide; and
    j) detecting the released non-complementary 5' flap, wherein the released non-complementary 5' flap is indicative of the presence of the target nucleic acid in the sample.

* * * * *

SEQUENCE LISTING

<160> NUMBER OF SEQ ID NOS: 21

<210> SEQ ID NO 1
<211> LENGTH: 43
<212> TYPE: DNA
<213> ORGANISM: Artificial
<220> FEATURE:
<223> OTHER INFORMATION: Heltest 4 oligonucleotide for FEN -continued endonuclease activity assay

<400> SEQUENCE: 1
aaaataaata aaaaaaatac tgttgggaag ggcgatcggt gcg   43

<210> SEQ ID NO 2
<211> LENGTH: 18
<212> TYPE: DNA
<213> ORGANISM: Artificial
<220> FEATURE:
<223> OTHER INFORMATION: cleavage product of oligonucleotide Heltest4

<400> SEQUENCE: 2
aaaataaata aaaaaaat   18

<210> SEQ ID NO 3
<211> LENGTH: 23
<212> TYPE: DNA
<213> ORGANISM: Artificial
<220> FEATURE:
<223> OTHER INFORMATION: FENAS primer

<400> SEQUENCE: 3
ccattcgcca ttcaggctgc gca   23

<210> SEQ ID NO 4
<211> LENGTH: 15
<212> TYPE: DNA
<213> ORGANISM: Artificial
<220> FEATURE:
<223> OTHER INFORMATION: B1 primer

<400> SEQUENCE: 4
cgatcgagca agcca   15

<210> SEQ ID NO 5
<211> LENGTH: 14
<212> TYPE: DNA
<213> ORGANISM: Artificial
<220> FEATURE:
<223> OTHER INFORMATION: B2 primer

<400> SEQUENCE: 5
cgagccgctc gctg   14

<210> SEQ ID NO 6
<211> LENGTH: 40
<212> TYPE: DNA
<213> ORGANISM: Artificial
<220> FEATURE:
<223> OTHER INFORMATION: S1 primer

<400> SEQUENCE: 6
accgcatcga atgcatgtct cgggtaaggc gtactcgacc   40

<210> SEQ ID NO 7
<211> LENGTH: 40
<212> TYPE: DNA
<213> ORGANISM: Artificial
<220> FEATURE:
<223> OTHER INFORMATION: S2 primer

<400> SEQUENCE: 7
cgattccgct ccagacttct cgggtgtact gagatcccct   40

```
<210> SEQ ID NO 8
<211> LENGTH: 20
<212> TYPE: DNA
<213> ORGANISM: Artificial
<220> FEATURE:
<223> OTHER INFORMATION: Upstream primer

<400> SEQUENCE: 8
aaggcgtact cgacctgaaa                                             20

<210> SEQ ID NO 9
<211> LENGTH: 21
<212> TYPE: DNA
<213> ORGANISM: Artificial
<220> FEATURE:
<223> OTHER INFORMATION: fluorogenic probe

<400> SEQUENCE: 9
accatacgga tagggatct c                                            21

<210> SEQ ID NO 10
<211> LENGTH: 20
<212> TYPE: DNA
<213> ORGANISM: Artificial
<220> FEATURE:
<223> OTHER INFORMATION: Fluorogenic probe

<400> SEQUENCE: 10
gcaaagtatc atccctccag                                             20

<210> SEQ ID NO 11
<211> LENGTH: 120
<212> TYPE: DNA
<213> ORGANISM: Artificial
<220> FEATURE:
<223> OTHER INFORMATION: Synthetic target

<400> SEQUENCE: 11
cctctgcaga ctactattac ataatacgac tcactatagg gatctgcacg tattagccta    60
tagtgagtcg tattaatagg aaacaccaaa gatgatattt cgtcacagca agaattcagg   120

<210> SEQ ID NO 12
<211> LENGTH: 20
<212> TYPE: DNA
<213> ORGANISM: Artificial
<220> FEATURE:
<223> OTHER INFORMATION: Synthetic target

<400> SEQUENCE: 12
cctctgcaga ctactattac                                             20

<210> SEQ ID NO 13
<211> LENGTH: 20
<212> TYPE: DNA
<213> ORGANISM: Artificial
<220> FEATURE:
<223> OTHER INFORMATION: Synthetic target

<400> SEQUENCE: 13
cctgaattct tgctgtgacg                                             20

<210> SEQ ID NO 14
<211> LENGTH: 24
<212> TYPE: DNA
<213> ORGANISM: Artificial
<220> FEATURE:
```

```
<223> OTHER INFORMATION: Fluorogenic probe

<400> SEQUENCE: 14
taggaaacac caaagatgat attt                                        24

<210> SEQ ID NO 15
<211> LENGTH: 49
<212> TYPE: DNA
<213> ORGANISM: Artificial
<220> FEATURE:
<223> OTHER INFORMATION: pCAL-n-EK cloning oligonucleotide

<400> SEQUENCE: 15
gacgacgaca agatgggtgt cccaattggt gagattatac caagaaaag             49

<210> SEQ ID NO 16
<211> LENGTH: 56
<212> TYPE: DNA
<213> ORGANISM: Artificial
<220> FEATURE:
<223> OTHER INFORMATION: pCAL-n-EK cloning oligonucleotide

<400> SEQUENCE: 16
ggaacaagac ccgtttatct cttgaaccaa ctttcaaggg ttgattgttt tccact     56

<210> SEQ ID NO 17
<211> LENGTH: 95
<212> TYPE: DNA
<213> ORGANISM: Artificial
<220> FEATURE:
<223> OTHER INFORMATION: Open circle probe

<400> SEQUENCE: 17
gaggagaata aagtttctc ataagactcg tcatgtctca gcagcttcta acggtcacta  60
atacgactca ctataggttc tgcctctggg aacac                            95

<210> SEQ ID NO 18
<211> LENGTH: 18
<212> TYPE: DNA
<213> ORGANISM: Artificial
<220> FEATURE:
<223> OTHER INFORMATION: Rolling circle replication primer

<400> SEQUENCE: 18
gctgagacat gacgagtc                                               18

<210> SEQ ID NO 19
<211> LENGTH: 23
<212> TYPE: DNA
<213> ORGANISM: Artificial
<220> FEATURE:
<223> OTHER INFORMATION: Upstream primer

<400> SEQUENCE: 19
aagtttctca taagactcgt cat                                         23

<210> SEQ ID NO 20
<211> LENGTH: 23
<212> TYPE: DNA
<213> ORGANISM: Artificial
<220> FEATURE:
<223> OTHER INFORMATION: Reverse primer

<400> SEQUENCE: 20
aggcagaacc tatagtgagt cgt                                         23
```

```
<210> SEQ ID NO 21
<211> LENGTH: 23
<212> TYPE: DNA
<213> ORGANISM: Artificial
<220> FEATURE:
<223> OTHER INFORMATION: Fluorogenic probe

<400> SEQUENCE: 21
agcttctaac ggtcactaat acg                                              23
```